United States Patent
Posner et al.

(10) Patent No.: US 10,227,634 B2
(45) Date of Patent: Mar. 12, 2019

(54) ISOTACHOPHORESIS ENHANCED ISOTHERMAL NUCLEIC ACID AMPLIFICATION

(71) Applicant: UNIVERSITY OF WASHINGTON, Seattle, WA (US)

(72) Inventors: Jonathan D. Posner, Seattle, WA (US); Mark D. Borysiak, Seattle, WA (US); Kevin Kimura, Seattle, WA (US)

(73) Assignee: University of Washington, Seattle, WA (US)

(*) Notice: Subject to any disclaimer, the term of this patent is extended or adjusted under 35 U.S.C. 154(b) by 0 days.

(21) Appl. No.: 15/566,631

(22) PCT Filed: Apr. 14, 2016

(86) PCT No.: PCT/US2016/027579
§ 371 (c)(1),
(2) Date: Oct. 13, 2017

(87) PCT Pub. No.: WO2016/168490
PCT Pub. Date: Oct. 20, 2016

(65) Prior Publication Data
US 2018/0100183 A1    Apr. 12, 2018

Related U.S. Application Data

(60) Provisional application No. 62/148,093, filed on Apr. 15, 2015.

(51) Int. Cl.
*G01N 27/447* (2006.01)
*G01N 33/48* (2006.01)
(Continued)

(52) U.S. Cl.
CPC .......... *C12Q 1/6806* (2013.01); *B01D 57/02* (2013.01); *C12N 15/101* (2013.01);
(Continued)

(58) Field of Classification Search
CPC ....... G01N 27/44756; G01N 27/44721; G01N 27/44747; G01N 27/447; G01N 27/44717;
(Continued)

(56) References Cited

U.S. PATENT DOCUMENTS 6,685,813 B2   2/2004  Williams
6,780,584 B1*  8/2004  Edman ................ B01J 19/0046
                                                        422/50
(Continued)

FOREIGN PATENT DOCUMENTS

WO    2014/006561 A2   1/2014
WO    2014075016       5/2014

OTHER PUBLICATIONS

Borysiak, Mark D. et al. "NAIL: Nucleic Acid detection using Isotachophoresis and Loop-mediated isothermal amplification" Lab on a Chip (2015) vol. 15. No. 7, pp. 1698-1701.
(Continued)

*Primary Examiner* — Susan D Leong
(74) *Attorney, Agent, or Firm* — McDonnell Boehnen Hulbert & Berghoff LLP

(57) ABSTRACT

The present disclosure relates generally to the integration of isotachophoresis (ITP) and isothermal nucleic acid amplification methods such as recombinase polymerase amplification (RPA). One aspect of the disclosure relates to a method for concentrating and amplifying a nucleic acid, the method including an isotachophoresis device, the isotachophoresis device including a porous matrix, and first and second electrodes, having a leading electrolyte, a trailing electrolyte and a set of isothermal nucleic acid amplification reaction reagents disposed in the porous matrix as described herein, and applying a voltage across the first electrode and the second electrode for a time sufficient to provide a first isotachophoresis (ITP) plug comprising an amplification
(Continued)

product of the nucleic acid, wherein the concentration of the nucleic acid is substantially higher in the first FTP plug than in the first and/or second fluids outside of the first ITP plug.

20 Claims, 23 Drawing Sheets

(51) Int. Cl.
  *C12Q 1/6806* (2018.01)
  *C12Q 1/6844* (2018.01)
  *B01D 57/02* (2006.01)
  *C12N 15/10* (2006.01)
  *C12Q 1/70* (2006.01)

(52) U.S. Cl.
  CPC .............. *C12Q 1/6844* (2013.01); *C12Q 1/70* (2013.01); *G01N 27/44791* (2013.01); *G01N 27/44795* (2013.01)

(58) Field of Classification Search
  CPC .............. G01N 27/4473; G01N 33/561; G01N 2001/4038
  See application file for complete search history.

(56) References Cited

U.S. PATENT DOCUMENTS

| | | | |
|---|---|---|---|
| 7,951,278 B2 | 5/2011 | Santiago | |
| 8,394,251 B2 | 3/2013 | Santiago | |
| 8,524,061 B2 | 9/2013 | Utz | |
| 8,562,804 B2 | 10/2013 | Santiago | |
| 8,580,097 B2 | 11/2013 | Kursawa | |
| 8,585,883 B2 | 11/2013 | Schoch | |
| 8,614,059 B2 | 12/2013 | Young | |
| 8,702,948 B2 | 4/2014 | Ronaghi | |
| 8,721,858 B2 | 5/2014 | Chambers | |
| 8,821,704 B2 | 9/2014 | Santiago | |
| 8,846,314 B2 | 9/2014 | Chambers | |
| 8,865,401 B2 | 10/2014 | Young | |
| 9,151,732 B2 | 10/2015 | Santiago | |
| 2010/0084271 A1 | 4/2010 | Santiago et al. | |
| 2010/0151531 A1* | 6/2010 | Shikata ................ C12O 1/6846 435/91.2 |
| 2010/0224494 A1 | 9/2010 | Chambers et al. | |
| 2011/0220499 A1* | 9/2011 | Chambers ........ G01N 27/44726 204/451 |
| 2011/0297546 A1 | 12/2011 | Schoch | |
| 2015/0152481 A1* | 6/2015 | Battrell ................ C12O 1/6806 435/287.2 |

OTHER PUBLICATIONS

Chen, Lin et al. "Total nucleic acid analysis integrated on microfluidic devices" Lab on a Chip (2007) vol. 7. No. 11; pp. 1413-1423.
The International Search Report (ISR) with Written Opinion for PCT/US2016/27579 dated Jul. 15, 2016, pp. 1-9.
Borysiak, et al., "NAIL: Nucleic Acid detection using Isotachophoresis and Loop-mediated isothermal amplification," Lab Chip 2015, 15 (7), 1697-1707.
Kondratova et al., "Tube Gel Isotachophoresis: A Method for Quantitative Isolation of Nucleic Acids from Diluted Solutions", Analytical Biochemistry (2011) vol. 408, Issue 2, p. 304-308.
Piepenburg, et al., "DNA Detection Using Recombination Proteins," PLoS Biol. 2006, 4 (7), e204.
Rogacs, et al., "Purification of nucleic acids using isotachophoresis," J. Chromatogr. A 2014, 1335, 105-120.
Rogacs et al., "Bacterial RNA Extraction and Purification from Whole Human Blood Using Isotachophoresis", Analytical Chemistry (2012) vol. 84 / Issue 14 / p. 5858-5863.
Rohrman et al., "Inhibition of Recombinase Polymerase Amplification by Background DNA: A Lateral Flow-Based Method for Enriching Target DNA," Anal. Chem. 2015, 87, 1963-1967.
Shintaku et al., "On-Chip Separation and Analysis of RNA and DNA from Single Cells", Analytical Chemistry (2014) vol. 36, Issue 4, p. 1953-1957.

* cited by examiner

ISOTACHOPHORESIS ENHANCED ISOTHERMAL NUCLEIC ACID AMPLIFICATION

CROSS-REFERENCE TO RELATED APPLICATIONS

This application is a U.S. national phase of International Application No. PCT/US2016/027579, filed on Apr. 14, 2016, which claims priority to U.S. Provisional Application No. 62/148,093 filed Apr. 15, 2015, both of which are incorporated by reference herein in their entirety.

BACKGROUND OF THE DISCLOSURE

Field of the Disclosure

The present disclosure relates generally to the integration of isotachophoresis (ITP) and isothermal nucleic acid amplification methods such as recombinase polymerase amplification (RPA). More particularly, the present disclosure relates to devices and methods for performing isotachophoretic concentration of a nucleic acid and/or amplification reagents into an ITP plug, in which an ITP plug and an isothermal nucleic acid amplification method such as RPA can provide a nucleic acid amplification product.

Technical Background

Isotachophoresis (ITP) is a nonlinear electrophoretic technique used to preconcentrate and separate a variety of ionic compounds, ranging from small metallic ions to large biomolecules such as proteins and nucleic acids. ITP is an effective electrophoretic concentration technique, with the potential of up to a million-fold concentration. In ITP, sample ions focus between leading (LE) and trailing electrolytes (TE) which have co-ions with respectively higher and lower effective electrophoretic mobilities than the sample ions. When a constant voltage or current is applied across the channel, sample ions accumulate and preconcentrate by electrophoresis into a number of contiguous zones between LE and TE zones, arranged in the order of their relative electrophoretic mobilities. Each zone has uniform characteristic concentration governed by electrophoresis conservation laws, namely the Kohlrausch regulating function (for fully ionized species) or more generally the Jovin-Alberty function (for all analytes, including both weakly- and strongly-ionized analytes), which calculate the adjusted concentrations of species in each zone. The adjusted concentration is the concentration each species obtains by electromigration into the zones previously occupied by species with another composition.

Depending on the initial concentration of the target sample, it can be focused (concentrated) in plateau mode or peak mode ITP. High initial sample concentrations and sufficient focusing time result in plateau mode ITP, which is characterized by distinct analyte zones each at a locally uniform concentration. At trace level concentrations, sample ions rarely form a plateau zone and operate in peak mode ITP where sample ions accumulate in a concentrated sample zone between LE and TE, which is referred to as an ITP plug. Various articles have described physics of peak mode ITP using numerical, analytical and experimental methods. Khurana & Santiago theoretically and experimentally studied sample zone dynamics in peak mode ITP in a glass capillary. They varied experimental parameters governing the sample zone dynamic independently, e.g., electrolyte concentration and applied current, to validate their analytical models and to provide a guide to experimental design and optimization of practical ITP assays. They reported, that in contrast to plateau mode ITP, there is an optimum LE concentration in peak mode ITP at which the highest concentration can be reached. They also showed that higher current densities and lower TE concentrations result in higher concentration ratios. Schwarz et al developed theoretical and numerical models to account for sample dispersion in peak mode ITP and showed non-uniform axial counter electroosmotic flow (EOF) results in sample dispersion. In addition, samples with mobility values near those of the TE or LE show greater diffusion into the TE or LE, respectively. They showed that advective dispersion caused by the non-uniform counter EOF when coupled with other sources of dispersion, can drastically reduce the ITP concentration ratio. Their models allow for fast and accurate prediction of dispersed sample distributions in ITP based on known parameters including species mobilities, electroosmotic (EO) mobility, applied current density and channel dimensions.

Diagnostics impact healthcare and food safety decisions by providing professionals the information needed to improve care, safety, and decision making. Point-of-care (POC) diagnostics can provide faster results with minimal instrumentation and user interaction compared to lab-based diagnostics. The rapid results and simplified testing provided by POC tests can lead to improved clinical outcomes, while reducing the cost of testing and care. For example, POC diagnostic platforms offer benefits for quickly diagnosing and monitoring hospital infections, viral and bacterial diseases in developing nations, and the presence of pathogenic bacteria in the field or at food production facilities.

Nucleic acid amplification tests have become the gold standard for many infectious disease diagnoses due to their high sensitivity and specificity, rapid operation, and low limits of detection. As of June 2014, the Food and Drug Administration (FDA) has approved over 150 different nucleic acid diagnostic tests for detecting pathogens including influenza, *Mycobacterium tuberculosis*, and *Staphylococcus*, with many more under commercial development for applications including global health and food safety testing. Some nucleic acid tests also have benefits including quantitative detection, such as real-time quantitative polymerase chain reaction (qPCR), and the versatility to detect multiple targets using multiplexing strategies.

Despite the advantages of nucleic acid tests, the requirements of complex sample preparation and lab-scale instrumentation limits the use of PCR to centralized laboratories with skilled personnel. All current clinical diagnostic nucleic acid tests are considered "high complexity" by the United States Clinical Laboratory Improvement Amendments (CLIA), with the exception of a few systems, such as the Cepheid GEN EXPERT®, BD Diagnostics BD MAX™ System, and Biofire Diagnostics FILMARRAY® RP system, which are characterized as "medium complexity," and the ALERE™ i Influenza A&B test, the Roche Cobas® Liat and the Cepheid GeneXpert® Omni which have been be granted "waived" status. "High complexity" tests are limited to central laboratories, while "medium complexity" tests can be performed near patients at a hospital. CLIA waived status is necessary for POC applications. Extraction and purification for PCR tests typically involves procedures that include multiple binding, washing, centrifugation, and elution steps that are labor intensive and time consuming. Commercial PCR instruments have been developed to automate sample preparation, amplification, and detection, but these systems still require thermocyclers, complex fluidic systems, and/or fluorescent laser detection that increase the cost and infrastructure requirements for testing.

Isothermal amplification methods (e.g., NASBA, HDA, RPA, NEAR, SDA, LAMP) have been developed to replace thermocycling equipment with heating blocks, water baths, or other simple heating methods. These characteristics make isothermal amplification techniques advantageous for nucleic acid diagnostics, but integration with sample preparation and detection remains challenging. Further, many of these tests still require significant time for results (e.g., >1 hour). Work has been done to improve sample preparation and overall device integration for isothermal amplification diagnostics, but further improvements in regards to necessary user steps, required instrumentation, and overall complexity are still necessary for point-of-care application.

Recombinase polymerase amplification (RPA) is a process in which recombinase-mediated targeting of oligonucleotides to DNA targets is coupled to DNA synthesis by a polymerase to exponentially amplify target nucleic acid sequences at low temperature, e.g., 25-42° C., but more commonly at 36-38° C. RPA does not require temperature melting because recombinase proteins form recombinase-primer complexes before scanning double-stranded sequences to facilitate strand exchange of oligonucleotide primers into the double-stranded DNA. The displaced strand is stabilized by a single-stranded binding protein (SSB) to prevent ejection of the inserted primer. A strand-displacing polymerase then performs primer extensions; continuation of this process results in exponential amplification of the target.

Current RPA technology can achieve amplification in as little as 10 minutes under optimal conditions. However, this requires relatively high target DNA concentration, pure samples, heating to 36-38° C., and the presence of crowding agents, which require the solution to be mixed. Under non-optimal conditions, e.g. low target DNA load, presence of contaminants, temperatures less than 30° C., and/or non-mixing conditions, the amplification requires significantly longer, if the amplification proceeds at all. Additionally, separate or non-integrated DNA extraction and purification is required for clinical samples that contain amplification inhibitors or other interferents that prohibit amplification and/or detection.

Accordingly, there remains a need for integrated, portable devices and methods capable of rapidly extracting, purifying, amplifying, and detecting nucleic acids from complex background media.

SUMMARY OF THE DISCLOSURE

One aspect of the disclosure is a method for concentrating and amplifying a nucleic acid, the method comprising
providing an isotachophoresis device, the isotachophoresis device including
a porous matrix having a first end and a second end opposing the first end, the first end and the second end defining a first axis, the porous matrix having a first fluid pathway having a first end and extending to a second end,
a first electrode, and
a second electrode;
a first fluid comprising a trailing electrolyte, disposed in the porous matrix within the first fluid pathway, the trailing electrolyte comprising an ion and a counterion, the first fluid being disposed such that the first electrode is in conductive contact with the first end of the first fluid pathway,
a second fluid comprising a leading electrolyte, disposed in the porous matrix within the first fluid pathway, the leading electrolyte comprising an ion and a counterion, the ion of the trailing electrolyte having a lower effective electrophoretic mobility than the ion of the leading electrolyte,
a set of isothermal nucleic acid amplification (INAA) reaction reagents, disposed in the porous matrix within the first fluid pathway and
the nucleic acid disposed in the porous matrix within the first fluid pathway, the nucleic acid having a higher effective electrophoretic mobility than the ion of the trailing electrolyte and a lower effective electrophoretic mobility than the ion of the leading electrolyte; and
applying a voltage across the first electrode and the second electrode for a time sufficient to provide a first isotachophoresis (ITP) plug comprising an amplification product of the nucleic acid, wherein the concentration of the nucleic acid is substantially higher in the first ITP plug than in the first and/or second fluids outside of the first ITP plug.

Another aspect of the disclosure is a device comprising:
a porous matrix having a first end and a second end opposing the first end, the first end and the second end defining a first axis, the porous matrix having a first fluid pathway having a first end and extending to a second end;
a first electrode disposed adjacent the first end of the first pathway;
a second electrode disposed adjacent the second end of the first pathway; and
one or more reagents of a set of INAA reaction reagents, disposed in the porous matrix within the first fluid pathway.

The device can, for example, further include a trailing electrolyte, disposed in the porous matrix within the first fluid pathway, the trailing electrolyte comprising an ion and a counterion; and/or a leading electrolyte, disposed in the porous matrix within the first fluid pathway, the leading electrolyte comprising an ion and a counterion, the ion of the leading electrolyte having a higher effective electrophoretic mobility than the ion of the trailing electrolyte.

Another aspect of the disclosure is a device comprising:
a porous matrix having a first end and a second end opposing the first end, the first end and the second end defining a first axis, the porous matrix having a first fluid pathway having a first end and extending to a second end;
a first electrode disposed adjacent the first end of the first pathway; and
a second electrode disposed adjacent the second end of the first pathway;
wherein the dimensions of the porous matrix are such that the application of between 50-200 Volts across the first electrode and the second electrode results in Joule heating of the porous matrix to a temperature between 30° C.-45° C.

Figure 3:
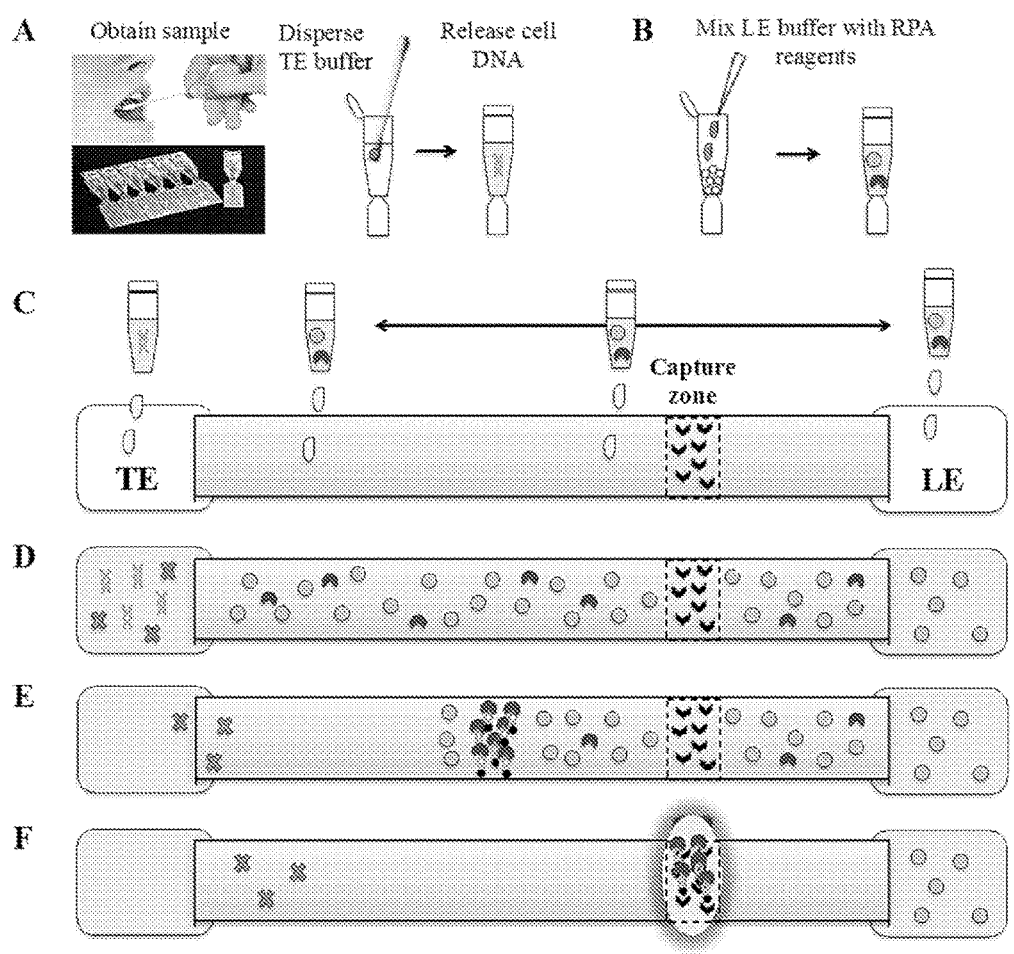
Figure 4:
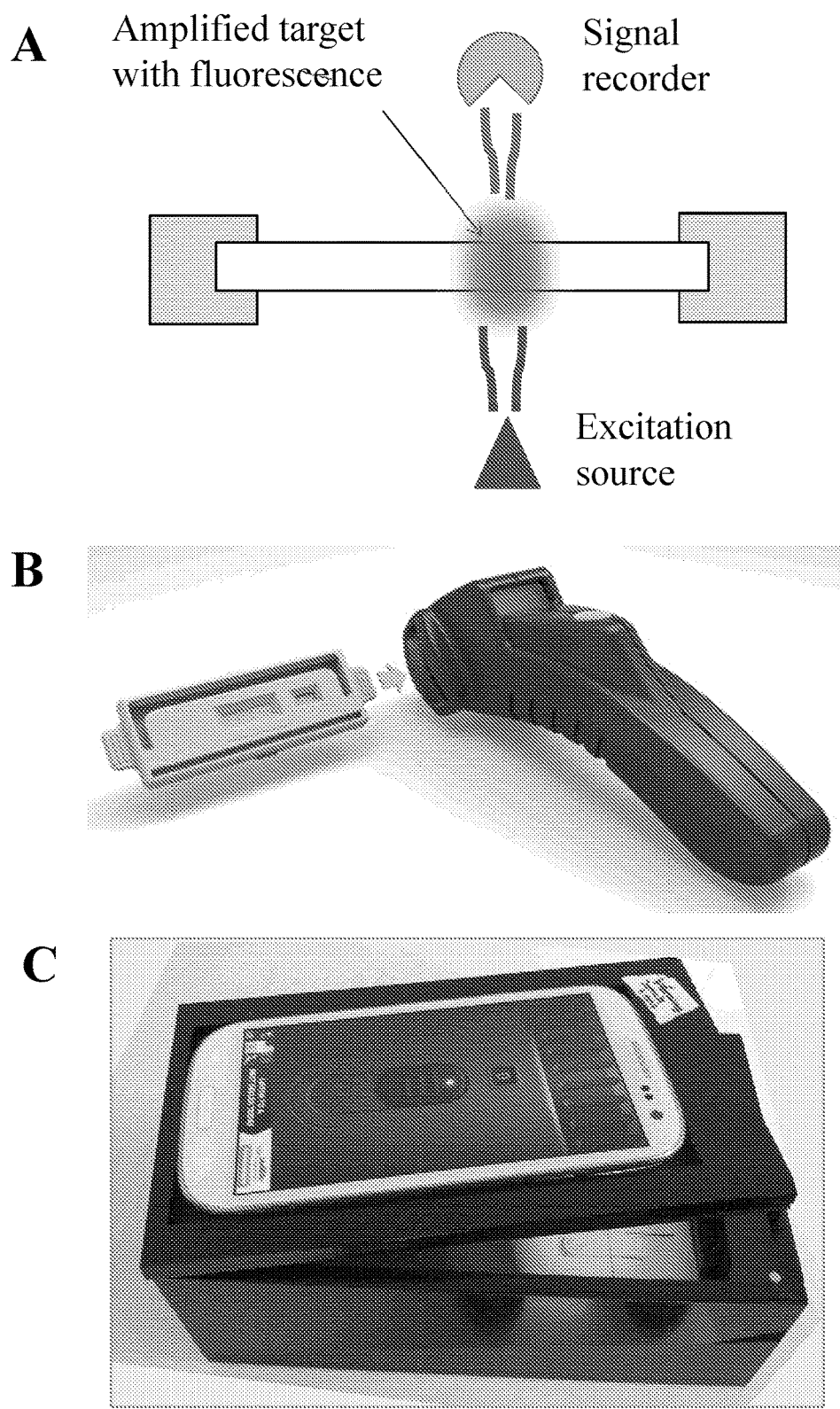
Figure 5:
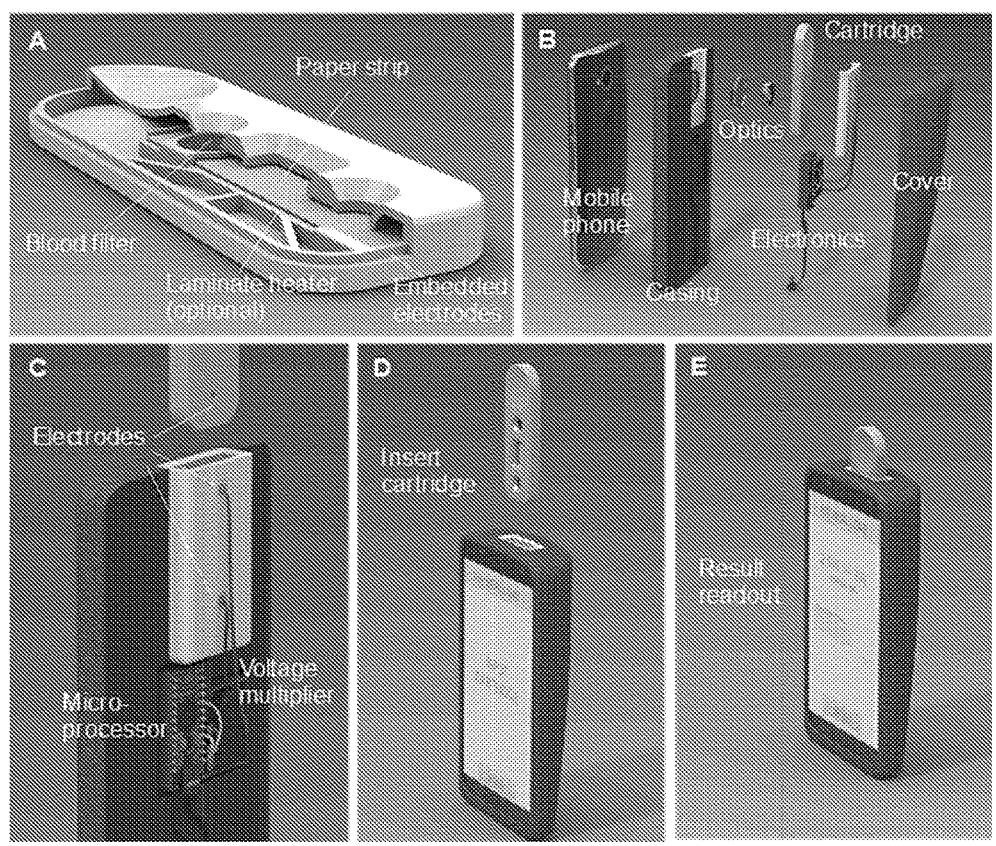
Figure 6:
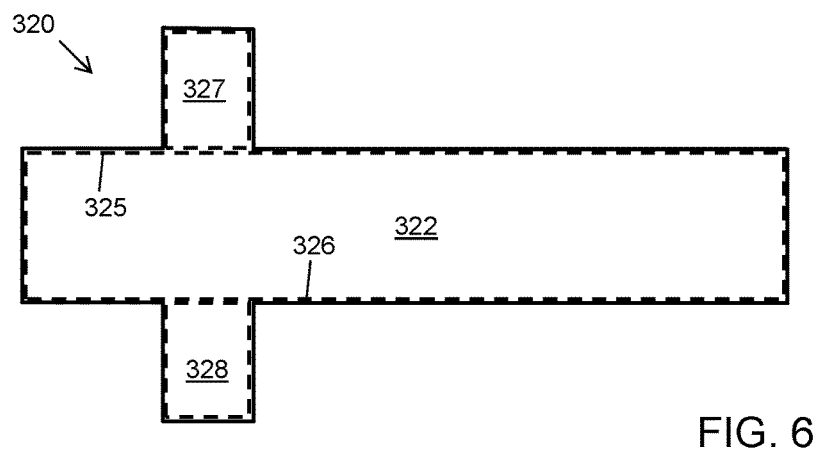
Figure 7A:
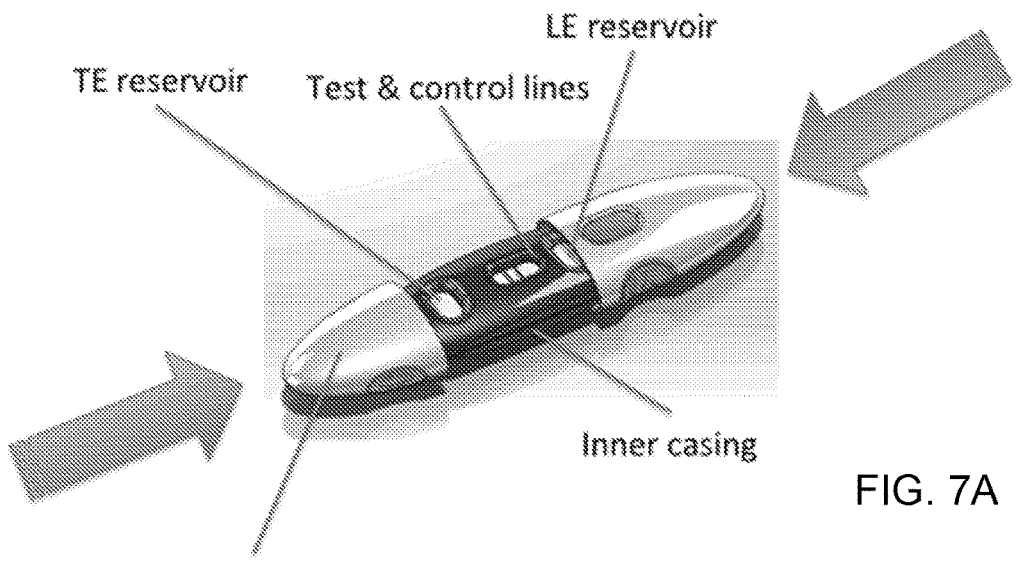
Figure 7B:
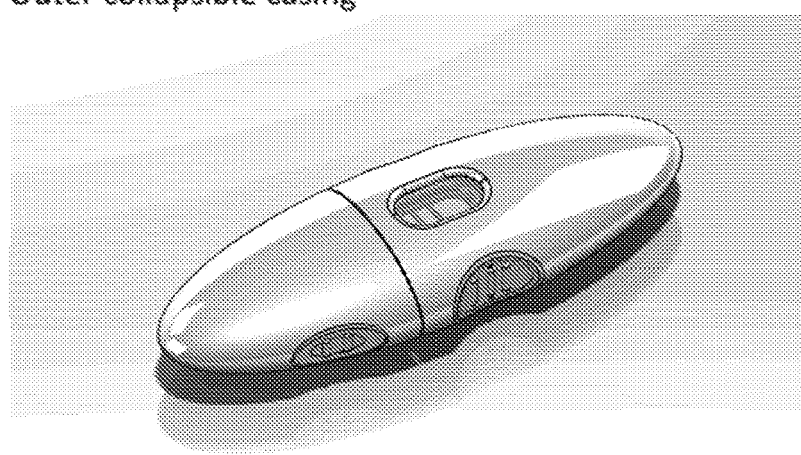
Figure 8:
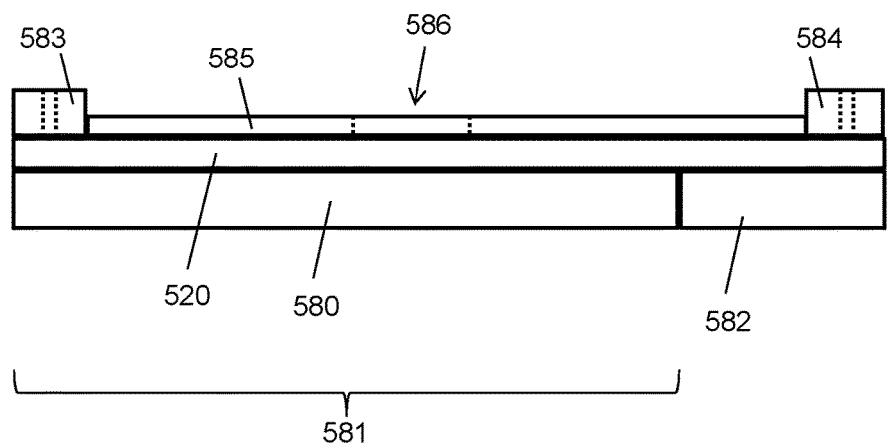
Figure 9:
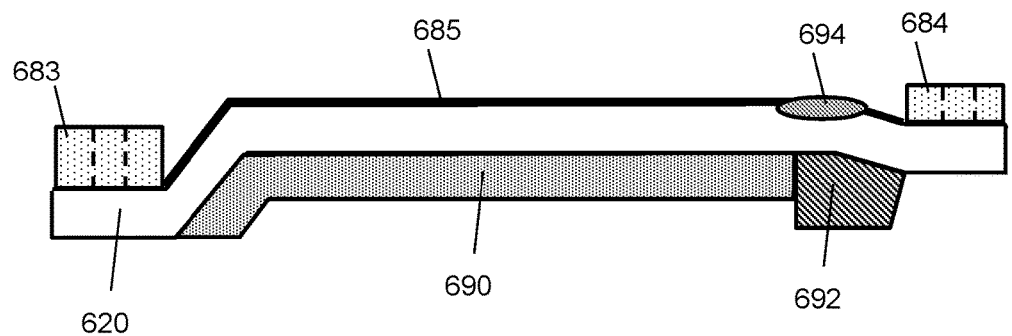
Figure 10:
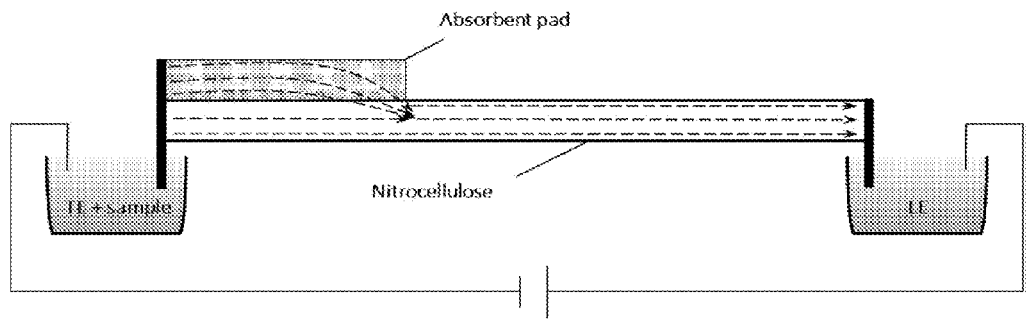
Figure 11A:
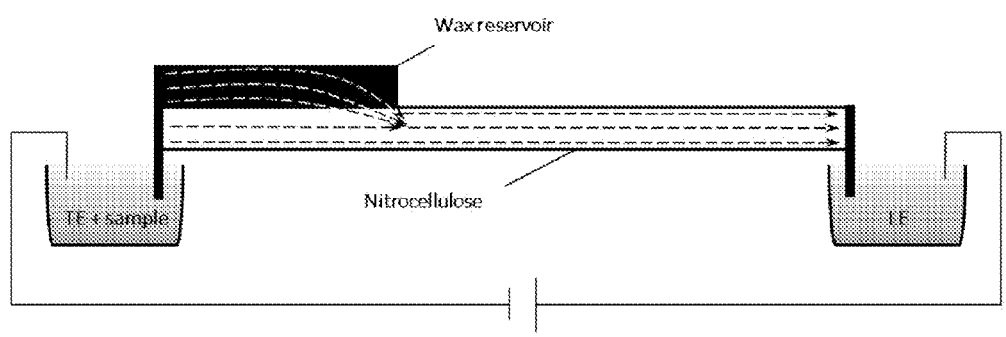
Figure 11B:
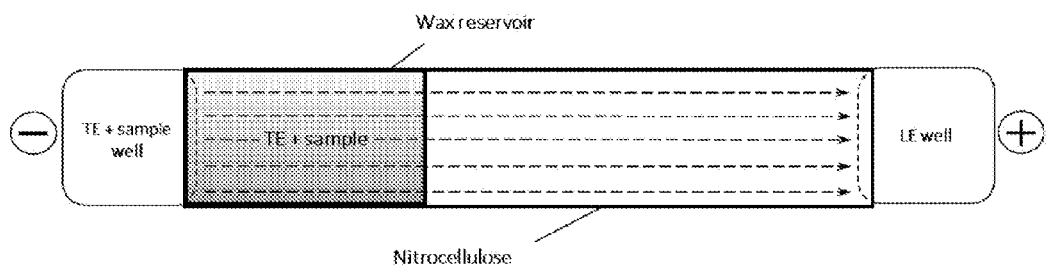
Figure 12:
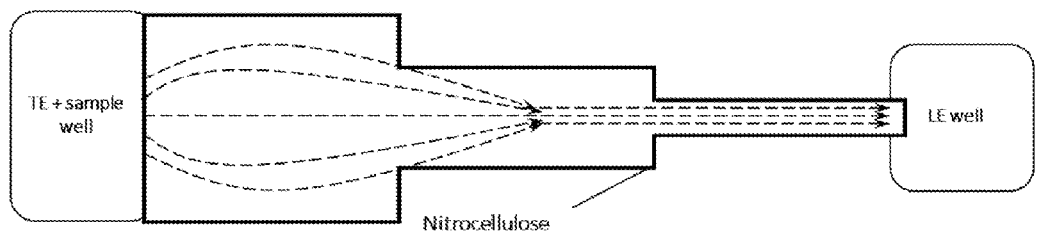
Figure 13:
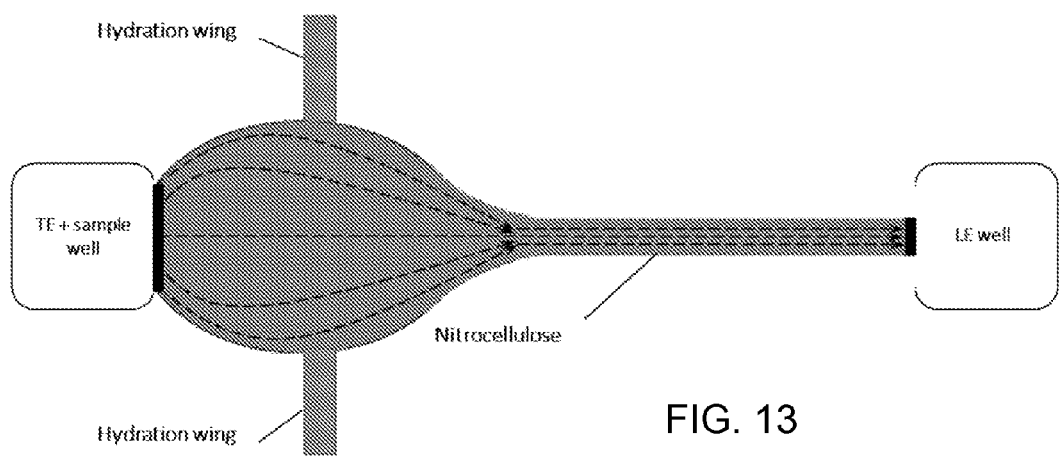
Figure 14:
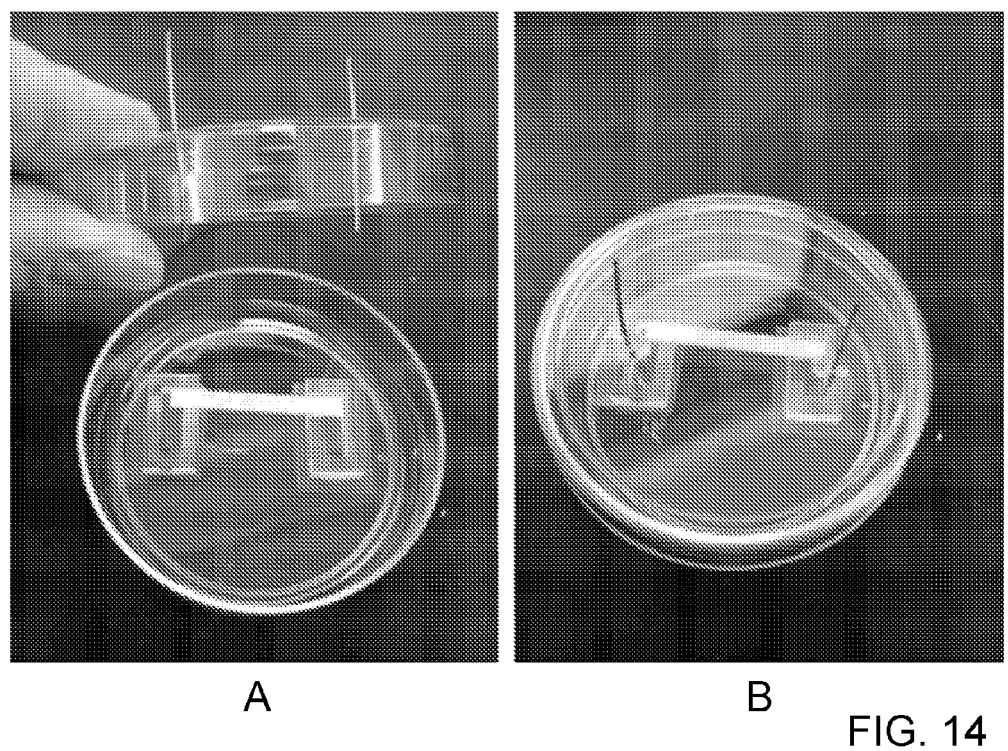
Figure 15:
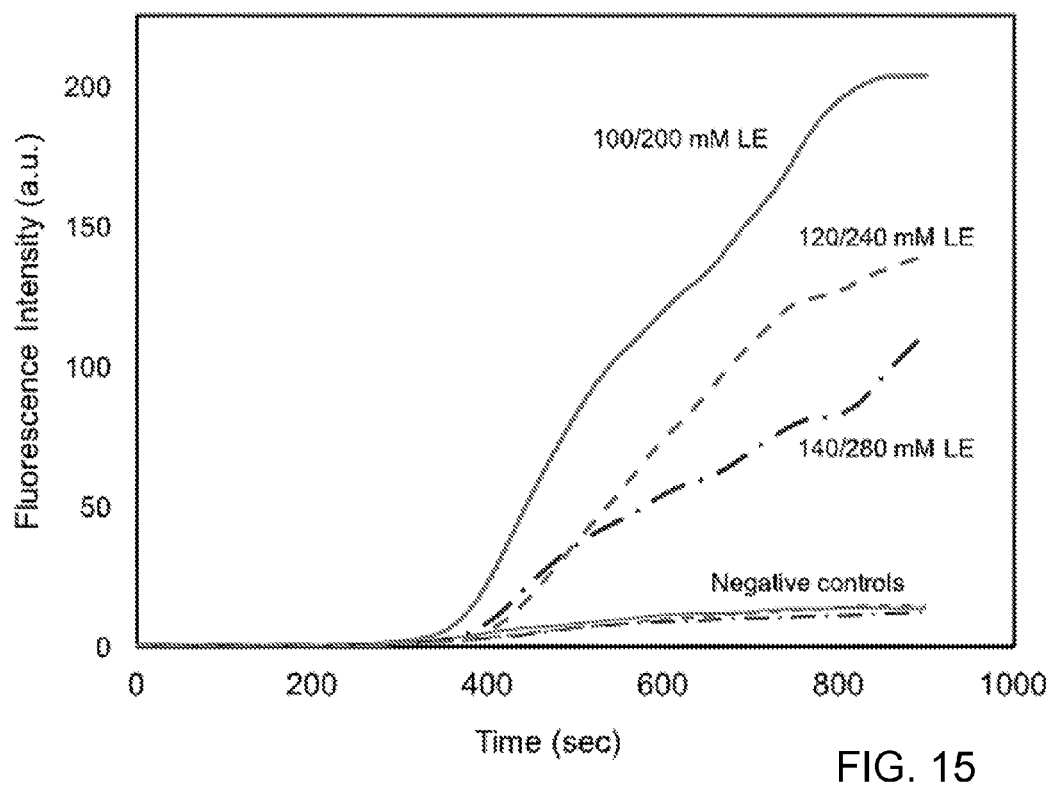
Figure 16:
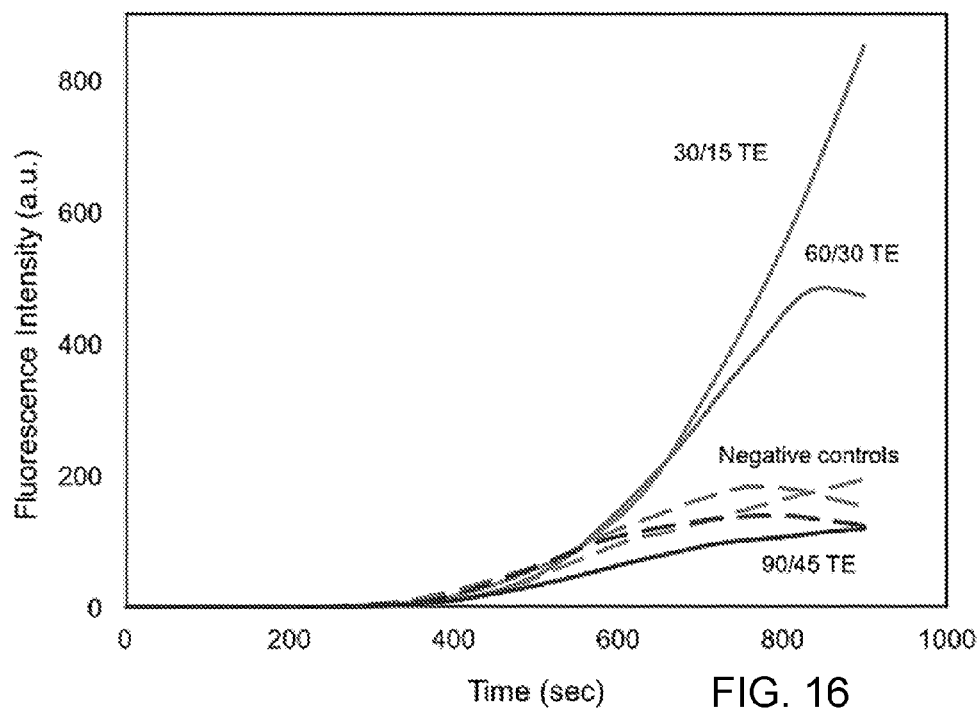
Figure 17:
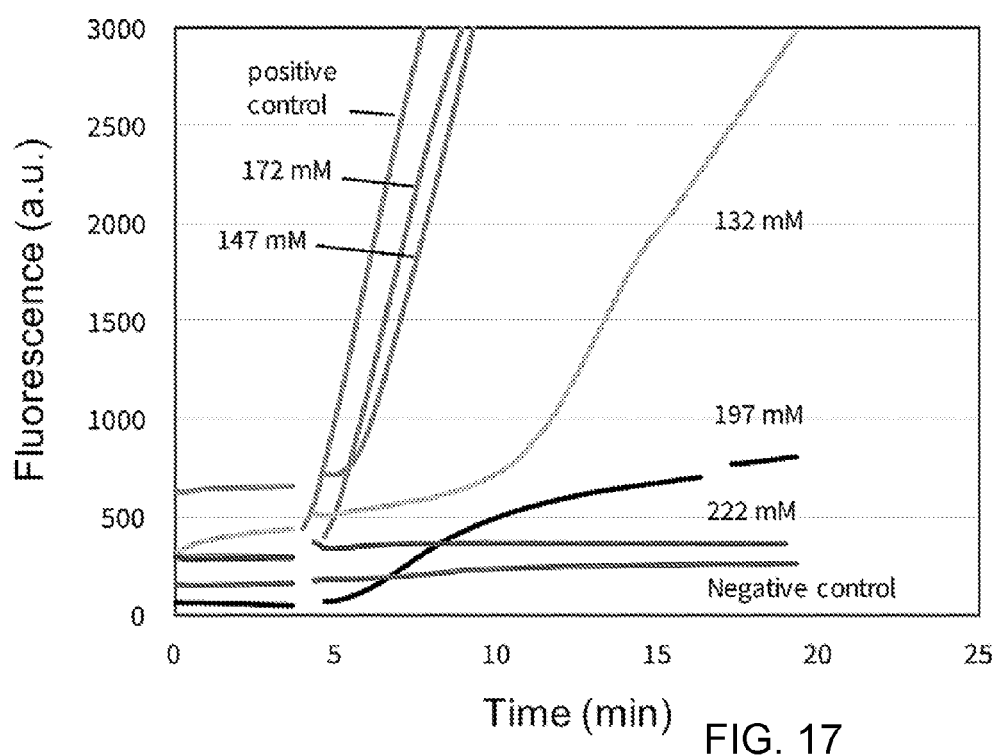
Figure 18:
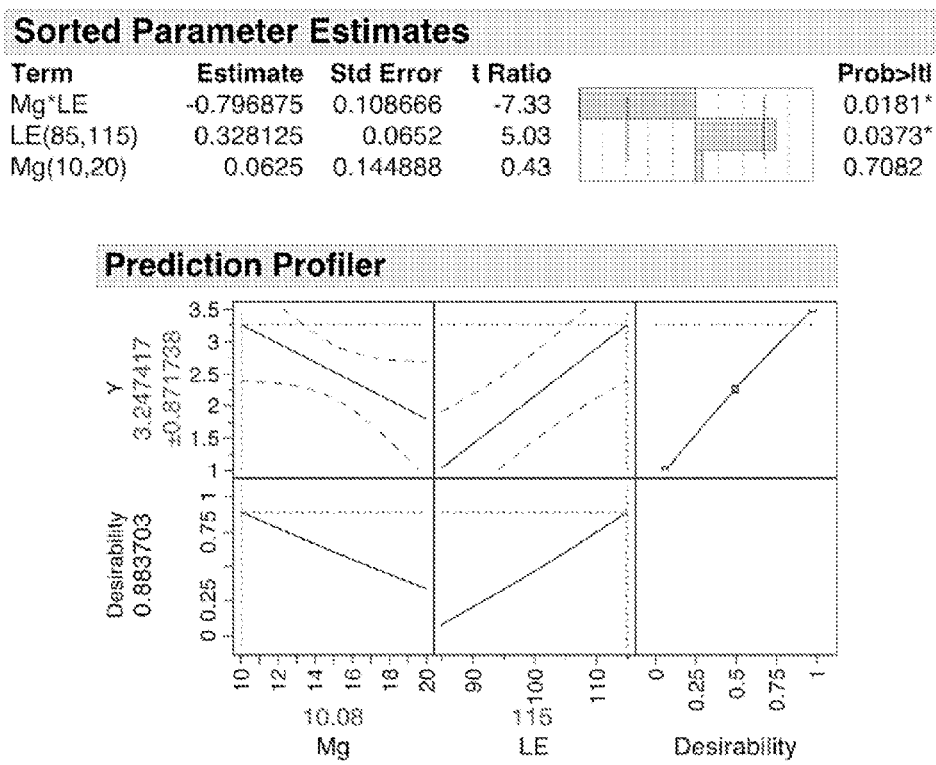
Figure 19:
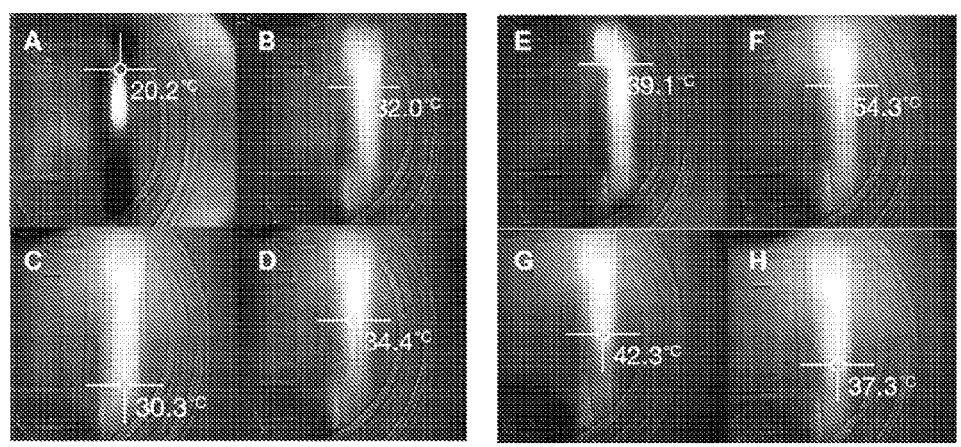
Figure 20:
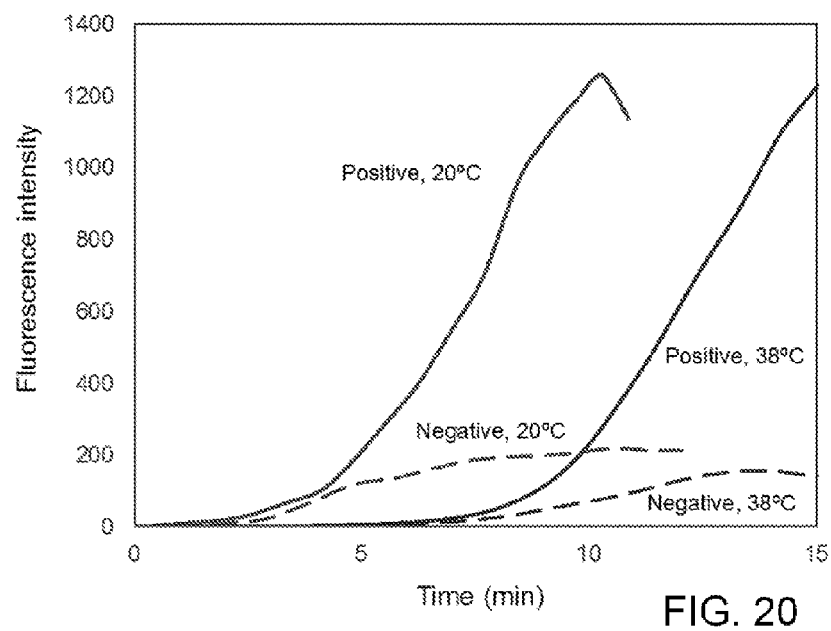
Figure 21:
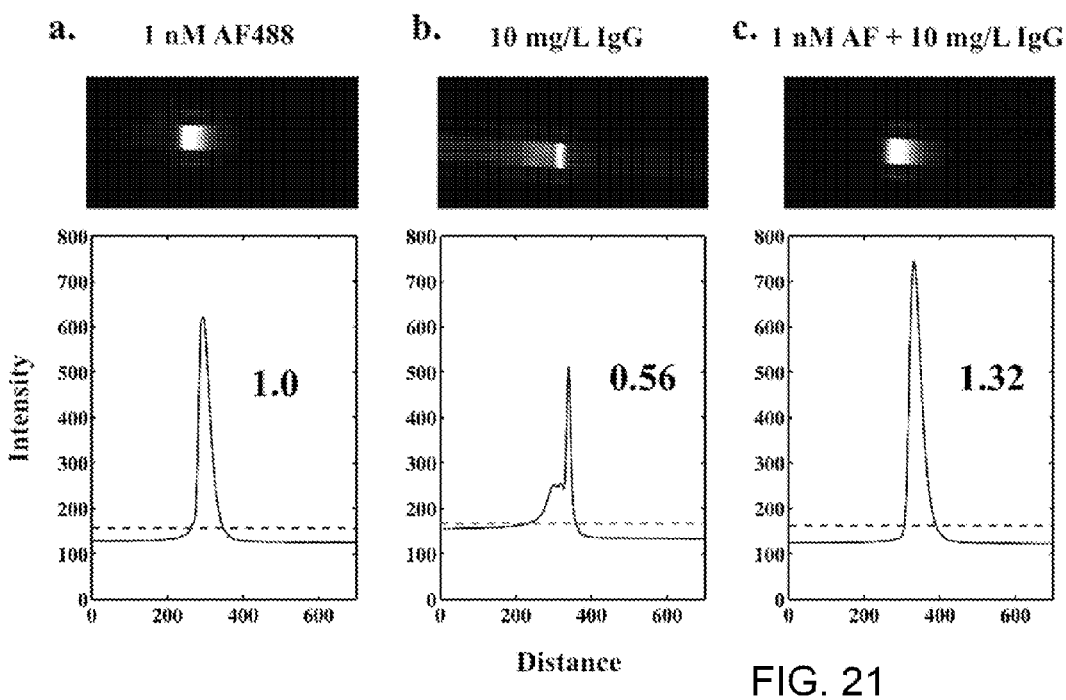
Figure 22:
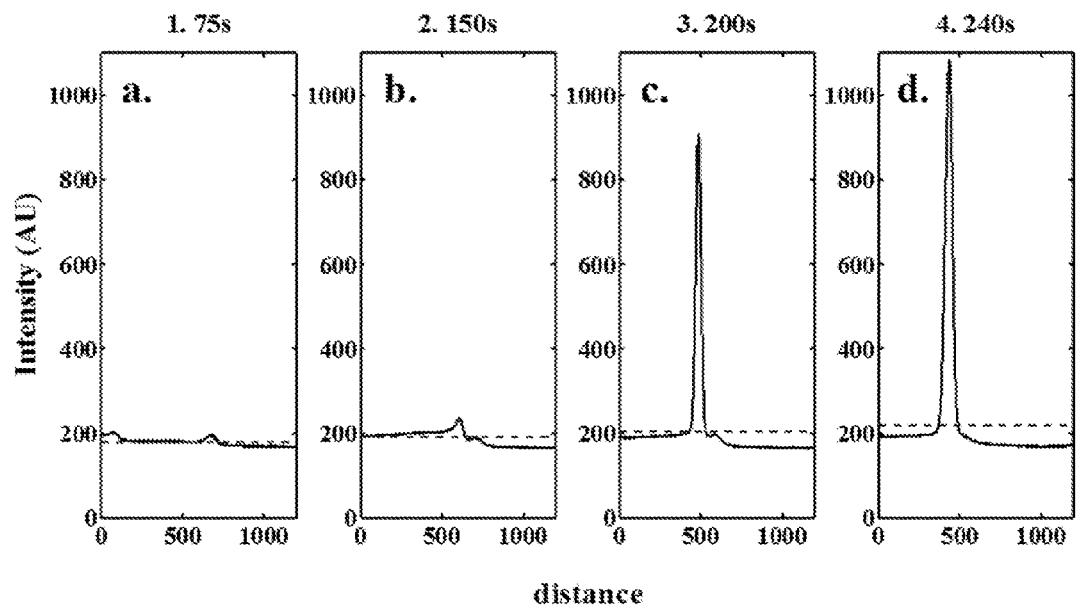
Figure 23:
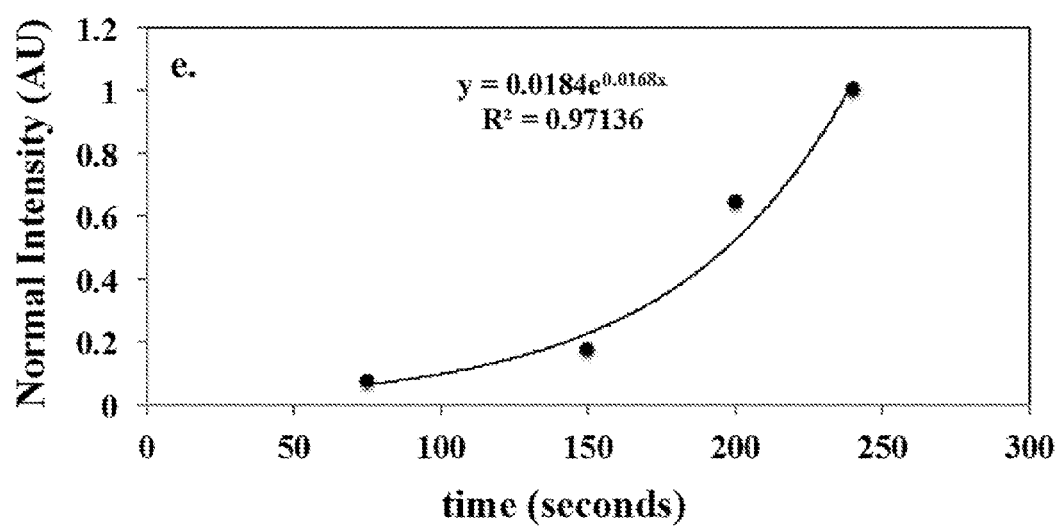
Figure 24:
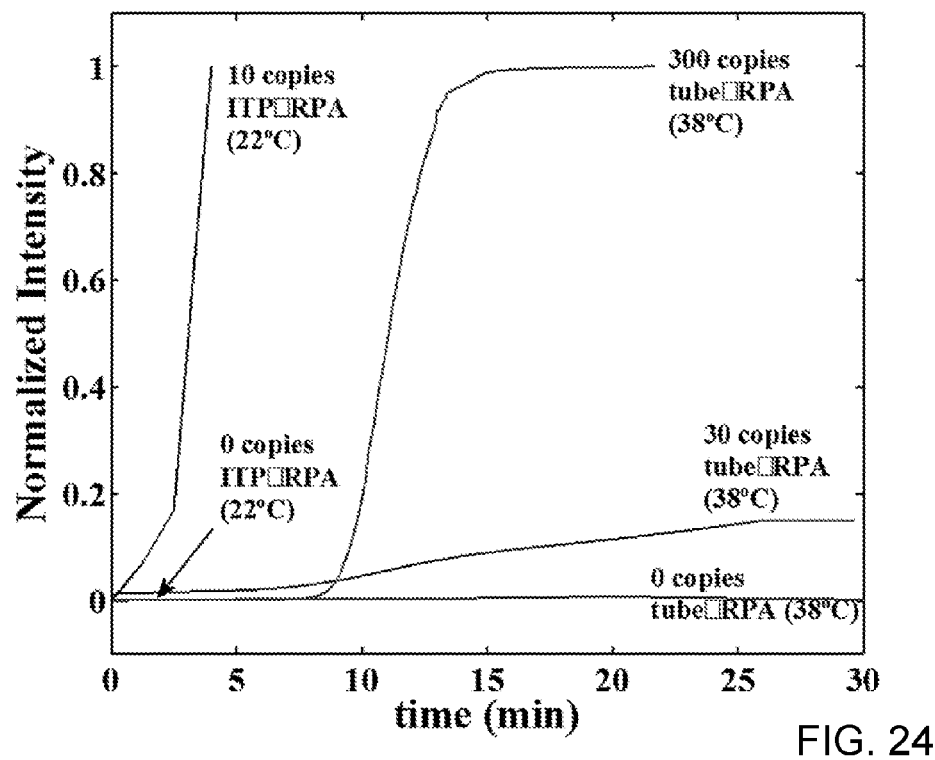
Figure 25:
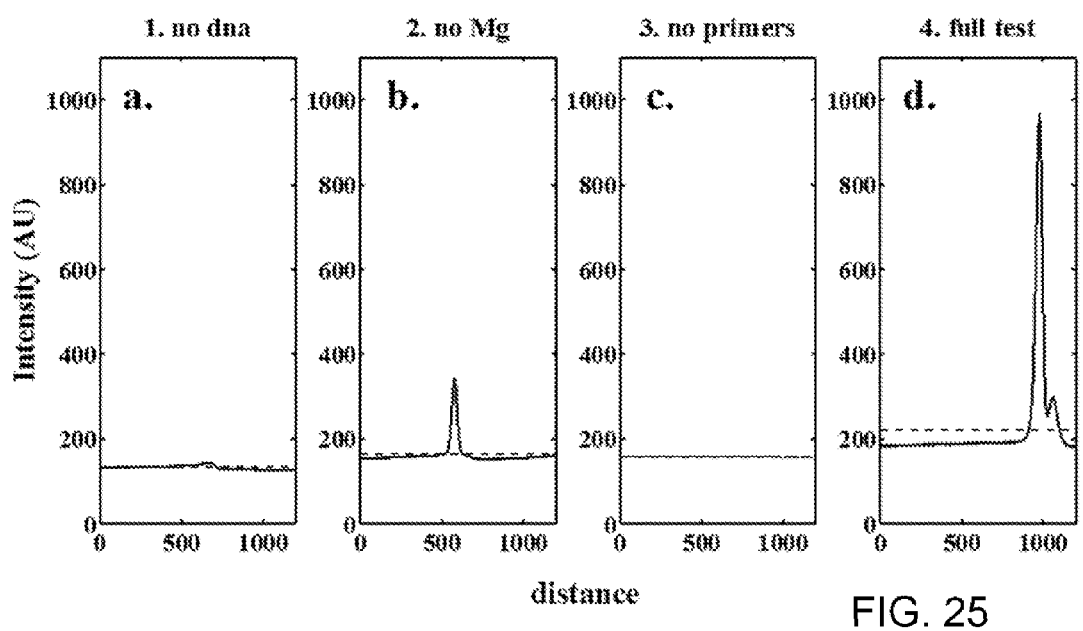
Figure 26:
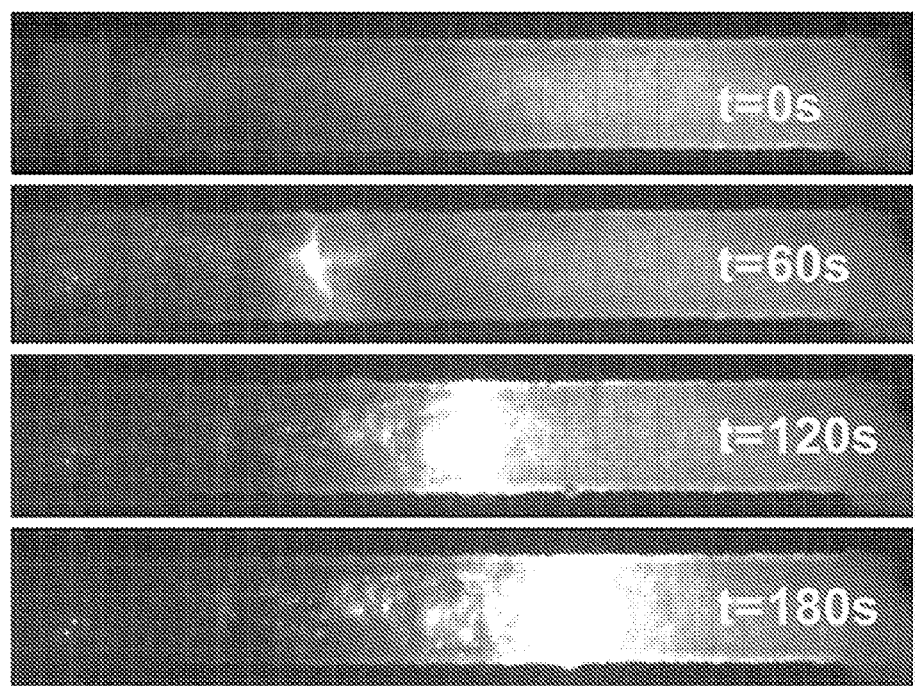
Figure 27:
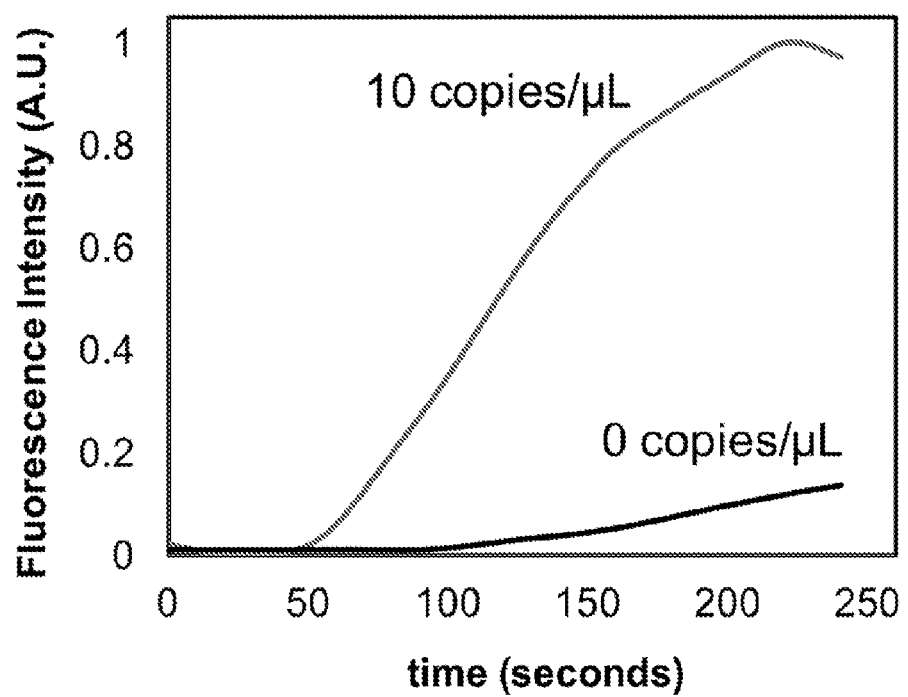
Figure 28:
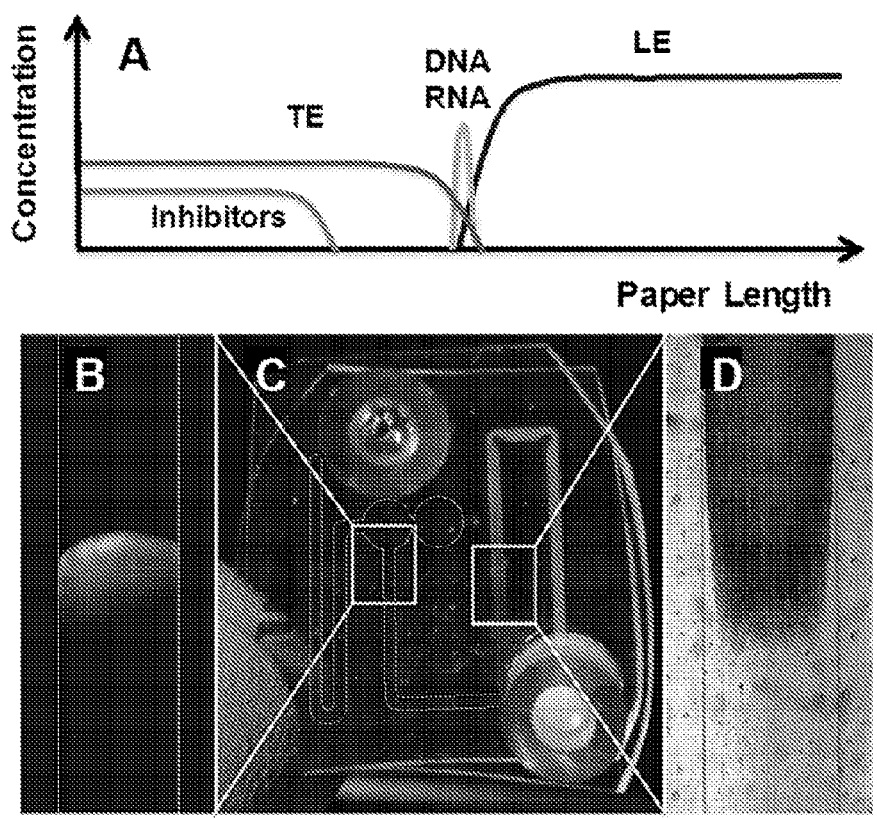
Figure 29:
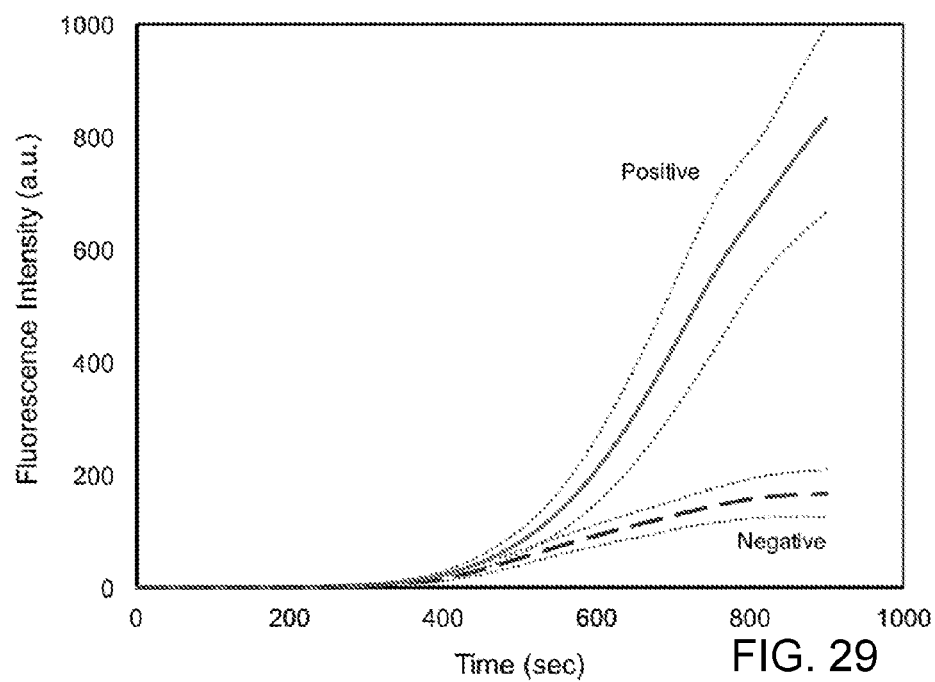
Figure 30:
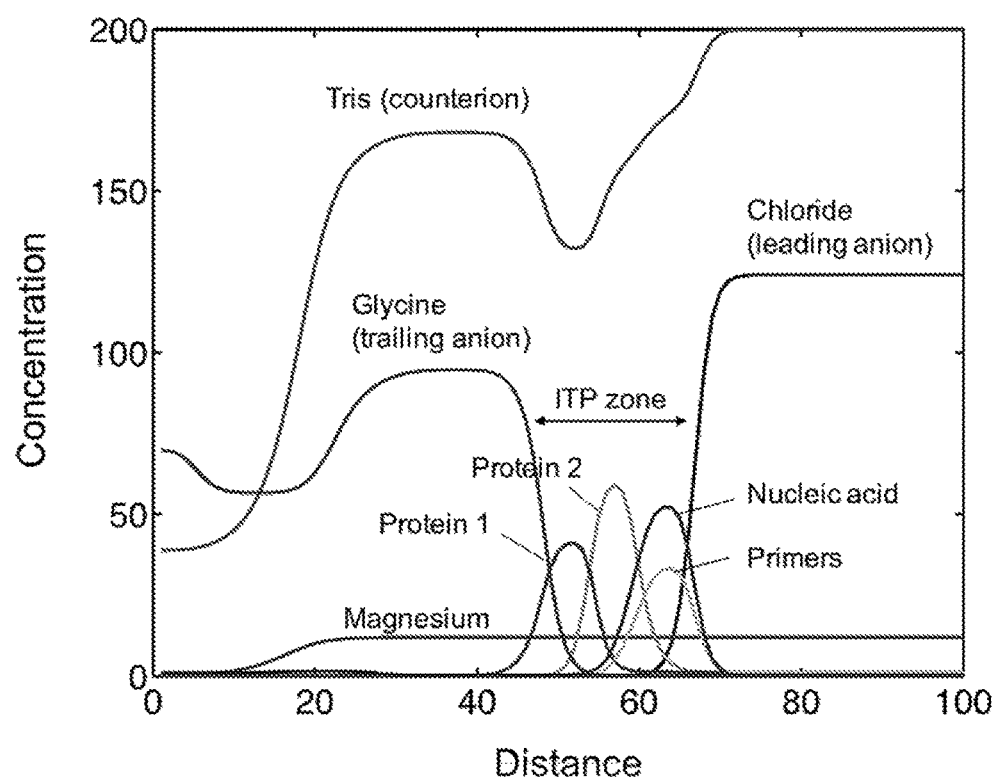
Figure 31:
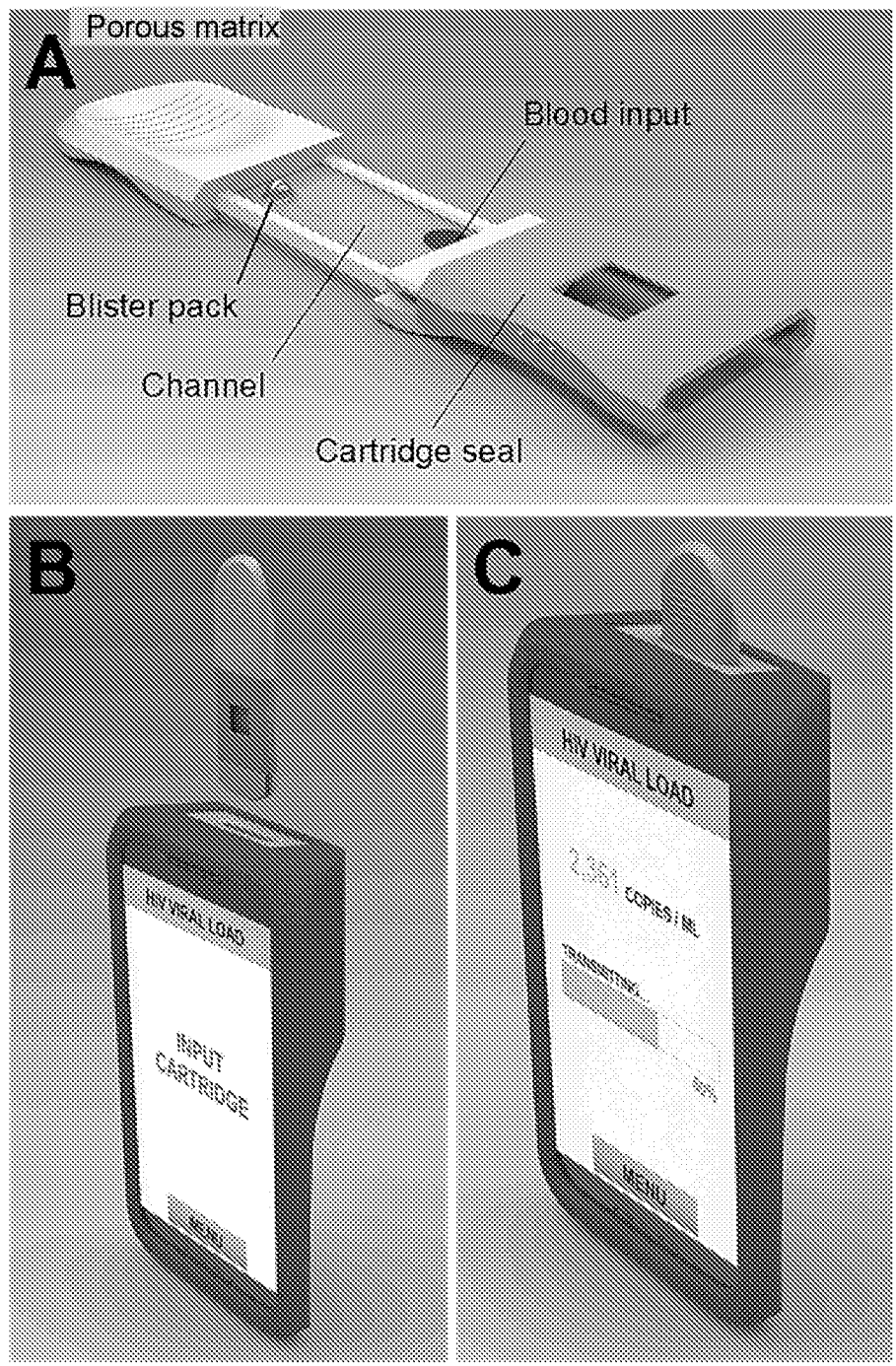
Figure 32:
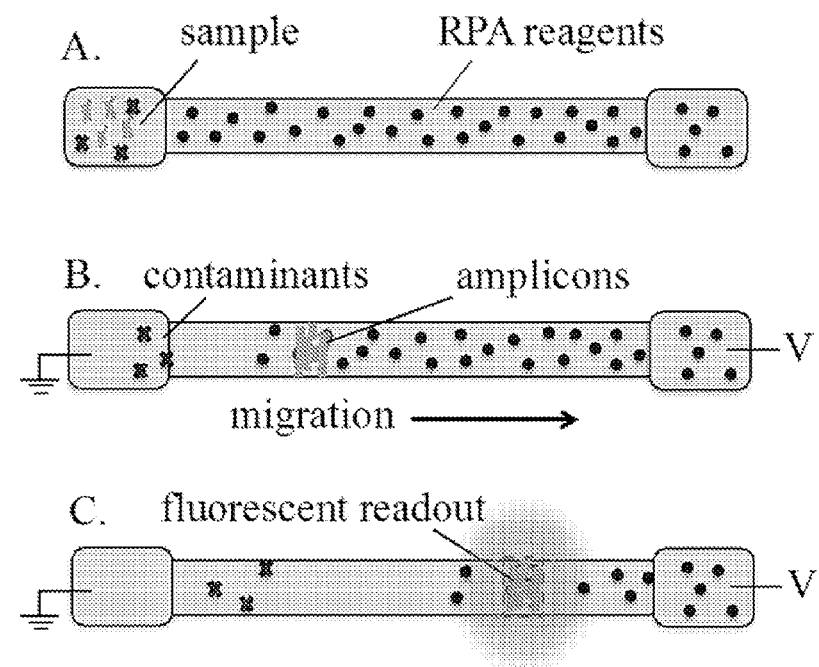
Figure 33:
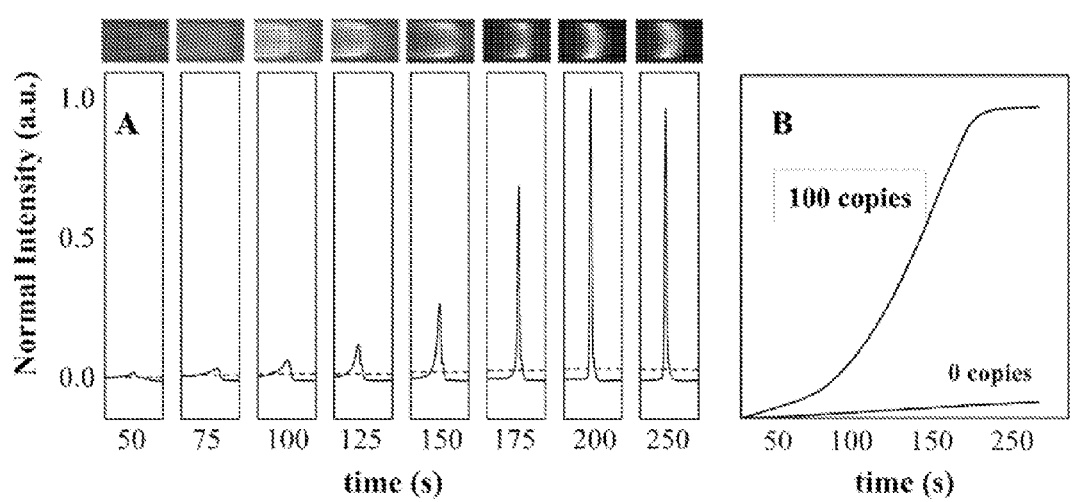
Figure 34:
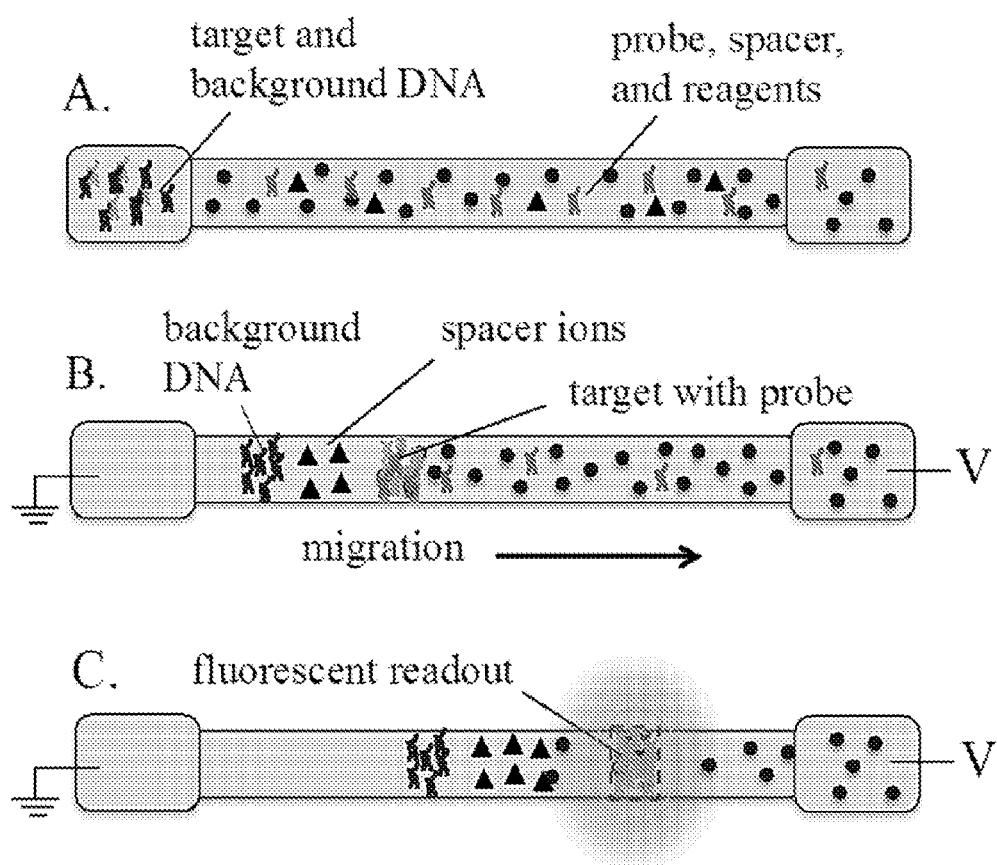
Figure 35:
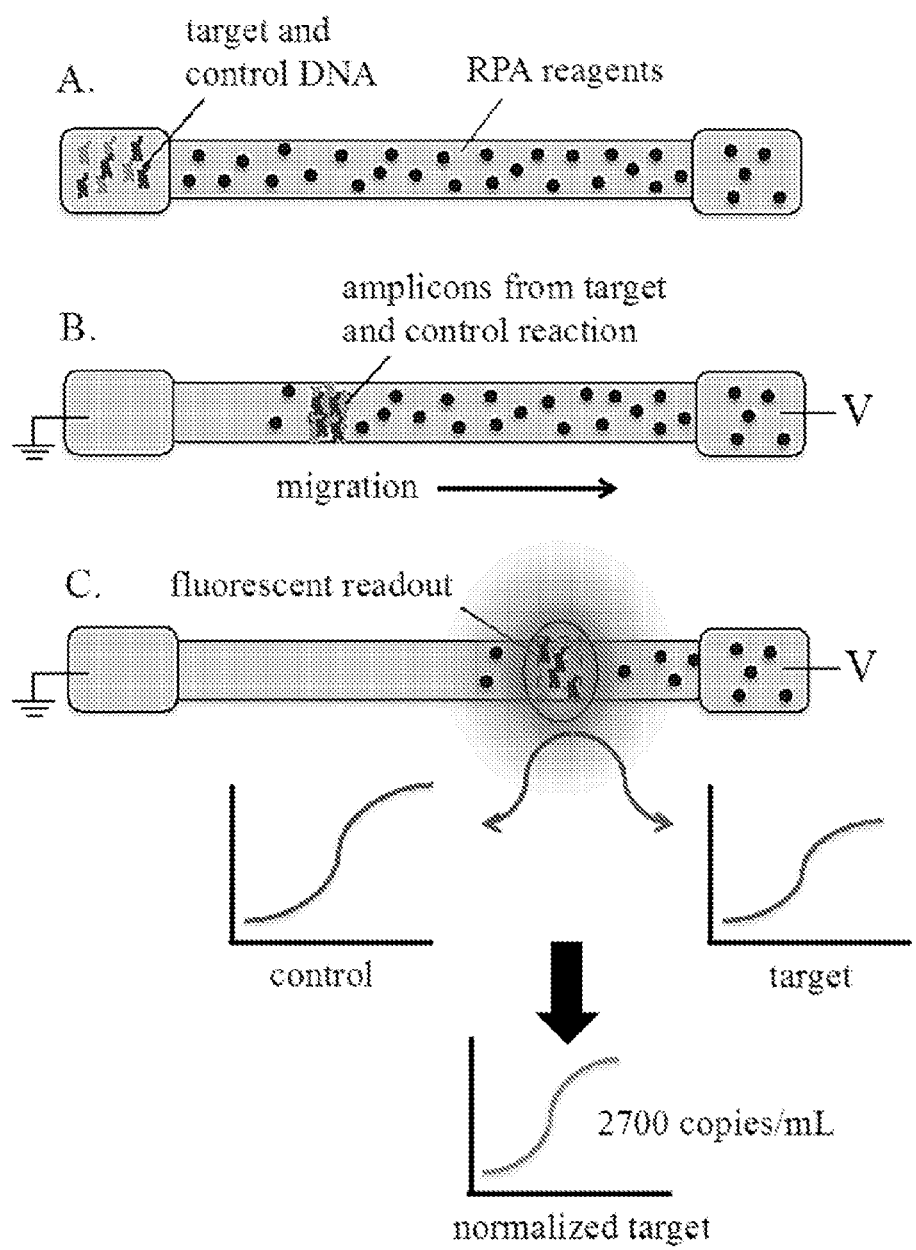

applying an electric field co-focuses the nucleic acid and RPA reaction reagents into an ITP plug and separates it from contaminants, (c) co-focusing and mixing of the nucleic acid and RPA reaction reagents results in rapid amplification of the nucleic acid, and (d) further amplification occurs, allowing for detection of the nucleic acid;

FIG. 3 shows a schematic view of an ITP enhanced RPA reaction method according to one embodiment of the disclosure, in which (A) a sample is obtained and mixed with the TE and a lysis agent in the first fluid, releasing the nucleic acid (spirals) into the first fluid, (B) the second fluid comprising the LE is added to dried RPA reaction reagents such as biotin- and FAM-labeled oligonucleotide primers (circles) and anti-FAM gold labels (half circles), (C) an anti-biotin detection zone is situated on the first fluid pathway between the first and second ends of the first fluid pathway, each of which is connected to a fluid reservoir, the first fluid is added to the reservoir attached to the first end of the first fluid pathway, and the second fluid is disposed onto the first fluid pathway along the first axis of the pathway and added to the reservoir attached to the second end of the first fluid pathway, to form (D) a complete ITP enhanced RPA device, to which (E) an electric field is applied, separating the nucleic acid from contaminants and contacting it with the RPA reagents, thus amplifying the nucleic acid in the ITP plug to provide dual-labeled FAM/biotin amplicons (green spirals attached to half circles), and (F) the dual-labeled amplicons are concentrated by ITP and captured by the anti-biotin detection zone as the ITP plug sweeps across the first fluid pathway, producing a colorimetric signal for identification of the target;

FIG. 4 shows (A) a schematic view of a fluorescent detection scheme of one embodiment of the disclosure, wherein a fluorescent signal is generated upon interaction with the nucleic acid amplification product of the ITP plug, which could be detected, for example, by the devices shown in (B), a model of a handheld fluorescent reader (DCN Diagnostics, Carlsbad, Calif.) which can read a fluorescent signal from an inserted ITP device, or (C), a mobile phone-based detection device, wherein the flash of a camera is sent through an excitation filter embedded in the lid of a dark box to a sample contained in the box, and wherein the dye emission is detected by the mobile phone;

FIG. 5 shows various views of a device for an ITP enhanced RPA reaction according to one embodiment of the disclosure, including (A) a model of a cartridge comprising a paper strip, a filter, electrodes, and an optional heater, wherein the paper strip can be filled with ITP enhanced RPA components and the sample can be added and filtered to remove large macromolecules to produce a serum comprising the nucleic acid, (B) a model of a mobile phone-based device comprising a camera-equipped mobile phone, a casing, optics, electronics and a cover, wherein the electronics, powered by the mobile phone battery, supply electrical current for ITP operation and the optics allow for imaging of fluorescent detection signals, wherein (C) a model of a mobile phone-based device in which the electronics comprise a microprocessor for voltage/current control and a voltage multiplier that allows higher output voltages than a standard cell phone battery, (D) a model of a mobile phone-based device in which insertion of a sealed cartridge initiates application of a voltage by the mobile phone-based device and detection of any subsequent fluorescent signal, and (E) a model of a mobile phone-based device providing an unambiguous readout of qualitative or quantitative results that indicate the presence/absence or amount of nucleic acid present in the sample;

FIG. 6 shows a schematic cross-sectional view of a porous matrix suitable for use in certain embodiments of the disclosure;

FIGS. 7A and 7B show perspective views of a device according to one embodiment of the disclosure, in an open state and a closed state, respectively;

FIG. 8 shows a schematic cross-sectional view of a device according to one embodiment of the disclosure;

FIG. 9 shows a schematic cross-sectional view of a device according to another embodiment of the disclosure;

FIG. 10 shows a schematic cross-sectional view of a device according to another embodiment of the disclosure;

FIGS. 11A and 11B show schematic cross-sectional and plan view of a device according to another embodiment of the disclosure;

FIGS. 12 and 13 show schematic plan views of two porous matrices suitable for use in various embodiments of the disclosure;

FIG. 14 shows a disposable petri dish setup for an ITP enhanced RPA reaction according to Example 1, comprising a reservoir for the first fluid (left) and a reservoir for the second fluid (right) attached to the first and second ends, respectively, of a glass fiber strip comprising the first fluid pathway, and a lid comprising embedded titanium electrodes that connect with the fluid reservoirs after the lid has been placed on the dish, in which (A) is the dish without the lid assembled thereon, and (B) is the dish with the lid assembled thereon;

FIG. 15 shows the effect of LE concentration on an ITP enhanced RPA reaction as described in Example 2;

FIG. 16 shows the effect of TE concentration on an ITP enhanced RPA reaction as described in Example 3;

FIG. 17 shows the effect of ionic strength on a tube format RPA reaction as described in Example 4;

FIG. 18 shows the dependence of an ITP enhanced RPA reaction on LE concentration, $Mg^{2+}$ concentration, and overall ionic strength as described in Example 4;

FIG. 19 shows the increase in temperature within an ITP enhanced RPA device due to Joule heating from applied electrical current as described in Example 5;

FIG. 20 shows the results of an ITP enhanced RPA reaction with and without external heating, as described in Example 5;

FIG. 21 shows the fluorescent bands (top) and the y-averaged fluorescence intensity (bottom) of the plug of ITP carried out on a sample of (a) ALEXAFLUOR® 488 (AF488) dye, (b) AF488-labeled IgG proteins, and (c) AF488 and AF488-labeled IgG proteins, as described in Example 6;

FIG. 22 shows the y-averaged fluorescence intensity over time of the plug of an ITP enhanced RPA reaction with the nucleic acid included in the first fluid comprising the TE and with fluorescent probes included in the second fluid comprising the LE, as described in Example 7;

FIG. 23 shows the integrated and normalized fluorescence intensities of each time point shown in FIG. 22 versus time as described in Example 7;

FIG. 24 shows the fluorescence intensity versus time for tube format RPA reactions at 38° C. and ITP enhanced RPA reactions at 22° C. with varying initial amounts of nucleic acid copies, as described in Example 8;

FIG. 25 shows the y-averaged fluorescence intensities of plugs of ITP enhanced RPA reactions carried out (a) without the nucleic acid, (b) without $Mg^{2+}$, (c) without oligonucleotide primers, or (d) with all necessary components, as described in Example 9;

FIG. 26 shows sequential fluorescence images over 180 seconds of an ITP enhanced RPA reaction with 10 copies/µL HIV-1 DNA included in the first fluid comprising the TE and with fluorescent probes included in the second fluid comprising the LE, as described in Example 10;

FIG. 27 shows the integrated and normalized fluorescence intensities of the plug of the ITP enhanced RPA reaction of Example 10 as a function of time compared to a similar reaction without any copies of HIV-1 DNA;

FIG. 28 shows a schematic plot of the ITP enhanced RPA component distribution (top) and experimental separation (bottom) of a nucleic acid from a complex sample (whole milk), as described in Example 11;

FIG. 29 shows the integrated and normalized fluorescence intensities of positive and negative control experiments demonstrating the detection of a nucleic acid from blood serum with ITP enhanced RPA, as described in Example 12;

FIG. 30 shows a SPRESSO simulation of the co-focusing of different RPA reaction reagents in the plug of an ITP enhanced RPA reaction, as described in Example 13;

FIG. 31 shows various views of a device for an ITP enhanced RPA reaction according to one embodiment of the disclosure, including (A) a model of a cartridge comprising a microfluidic chip with a single sample inlet and blister pack containing necessary ITP enhanced RPA components, inside a small plastic housing that has a sliding seal, wherein (B) a model demonstrating insertion of the sealed cartridge to an automated, handheld device initiates device operation, after which (C) results of the test are displayed and/or transmitted, as described in Example 14;

FIG. 32 shows one embodiment of an ITP enhanced RPA reaction that can proceed in a handheld ITP enhanced RPA cartridge and reader, wherein (A) the first fluid channel is filled with the necessary ITP enhanced RPA components and the sample reservoir is filled with the nucleic acid and contaminants from the sample, (B) application of a voltage across the first fluid channel separates the nucleic acid from the contaminants and concentrates the nucleic acid and the RPA reaction reagents into an ITP plug, in which (C) accelerated RPA reaction kinetics allow for a fast and unambiguous readout of the results, as described in Example 14;

FIG. 33 shows the increase in the detectible fluorescence of a plug of one embodiment of an ITP enhanced RPA reaction that might proceed in a handheld ITP enhanced RPA cartridge and reader, such as that described in Example 14;

FIG. 34 shows one embodiment of an ITP enhanced RPA reaction in which specific probes are used to alter the mobility of targets for ITP separation from background nucleic acids, wherein (A) the sample reservoir is filled with the nucleic acid and background nucleic acids, while the first fluid channel comprises the probe, spacer ions, and ITP enhanced RPA components, (B) application of a voltage across the first fluid channel starts the ITP, which initializes binding of probes to the nucleic acid, causing the target acid to migrate into a different ITP plug than the background nucleic acid, with spacer ions separating the two ITP plugs, and (C) an RPA reaction proceeds without inhibition of background nucleic acids, allowing for fluorescent detection of the target, as described in Example 15;

FIG. 35 shows one embodiment of an ITP enhanced RPA reaction in which detection of the nucleic acid is quantifiable, wherein (A) target and control nucleic acids are included on an ITP enhanced RPA device with RPA reaction reagents, (B) application of a voltage across the first fluid channel co-focuses the target and control nucleic acid into an ITP plug, in which both nucleic acids undergo RPA, and (C) the fluorescence readouts from the reactions of the two nucleic acids are completed at different wavelengths, the separate kinetic curves are run through an algorithm wherein the nucleic acid output undergoes normalization using the control output such that the initial concentration of the nucleic acid can be quantified, as described in Example 16.

Figure 36:
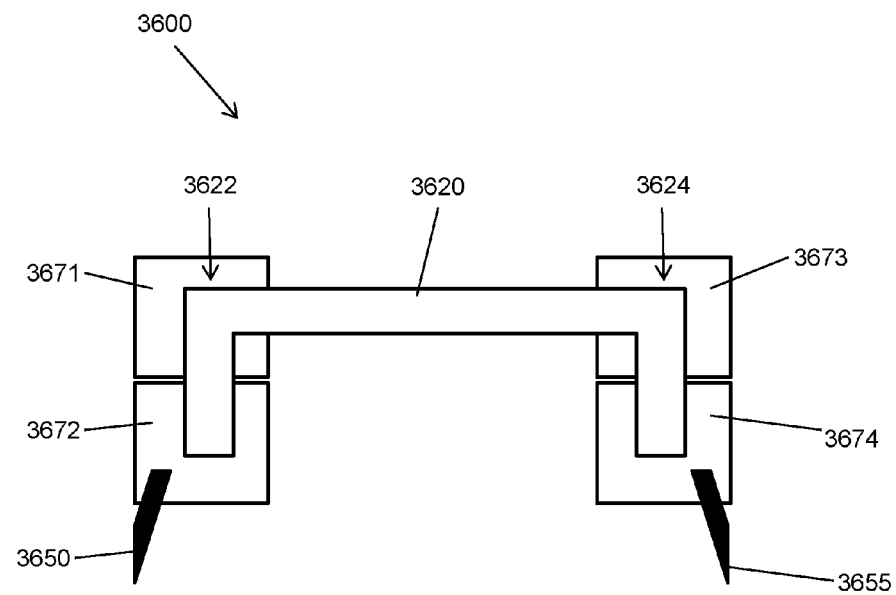

FIG. 36 is a schematic plan view of a device according to another embodiment of the disclosure.

Figure 37:
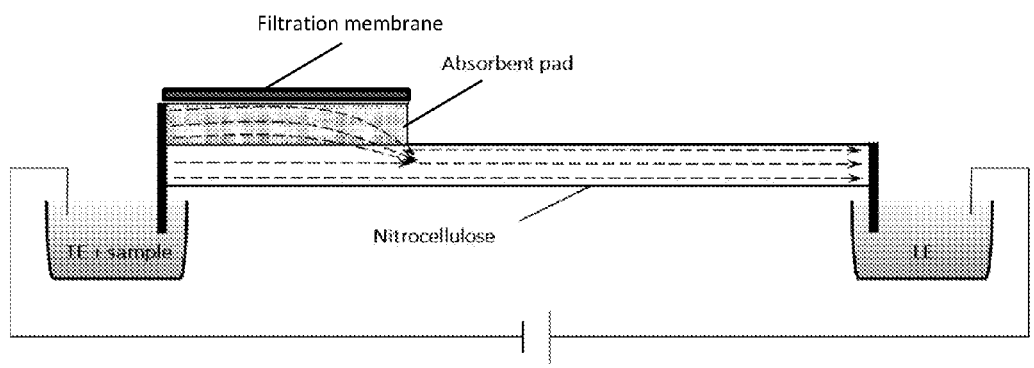
Figure 38:
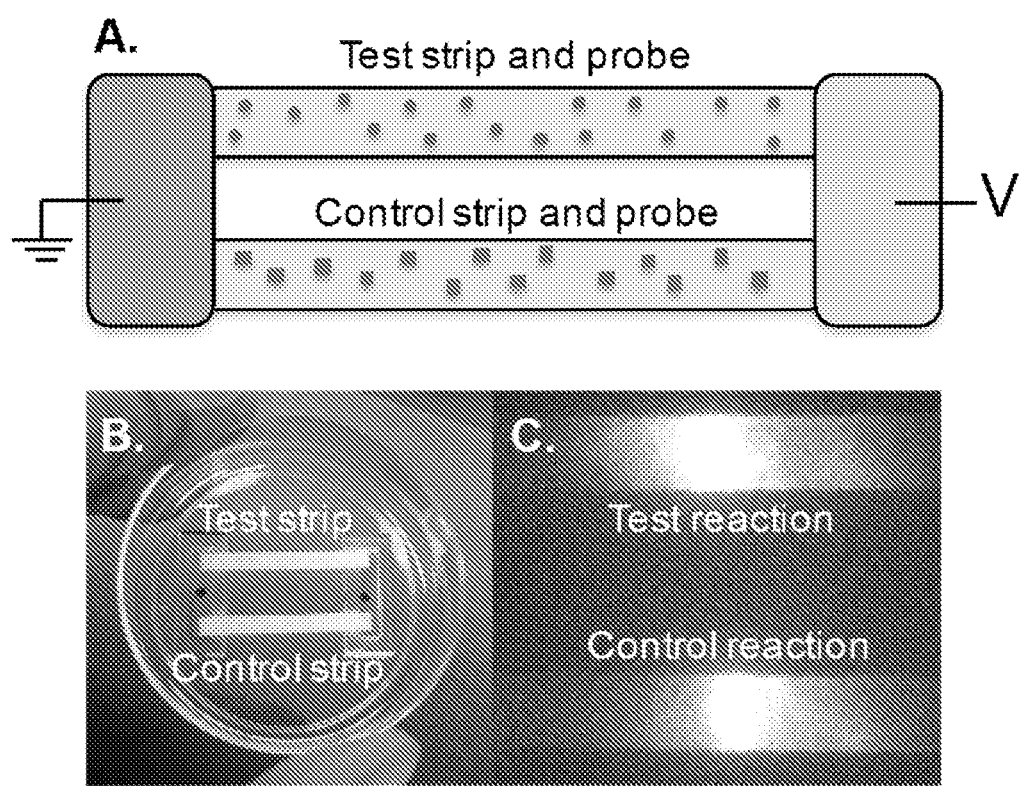

FIG. 37 shows a schematic cross-sectional view of a device according to another embodiment of the disclosure;

FIG. 38 shows (A) a schematic plan view and (B) a photographic top view of a device having two strips of porous matrix, each extending from a leading electrolyte reservoir to a trailing electrolyte reservoir; and (C) a photograph of fluorescence from both strips after an ITP-enhanced RPA experiment as described herein.

DETAILED DESCRIPTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

In various aspects and embodiments, the disclosure relates to the integration of isothermal amplification methods such as recombinase polymerase amplification (RPA), an isothermal nucleic acid amplification method, with isotachophoresis (ITP), an electrokinetic concentration and extraction method. The disclosure demonstrates ITP-enhanced RPA to be a rapid and portable technique to improve the extraction, purification, and detection of nucleic acids from background media by mixing focused nucleic acids with RPA reaction reagents. Such focusing and mixing results in rapid amplification of nucleic acids due to the high local concentration of RPA reactants, greatly improving target detectability.

Various aspects and embodiments of the disclosure are described specifically with respect to RPA. However, the person of ordinary skill in the art will appreciate that the methods described herein can be used with other isothermal amplification methods, such as loop-mediate isothermal amplification (LAMP), helicase dependent amplification reaction (HDA), nicking enzyme amplification reaction (NEAR), nucleic acid sequence based amplification (NASBA), strand displacement amplification (SDA) and cross-priming amplification (CPA). Thus, the person of ordinary skill in the art will adapt the procedures described herein with respect to RPA for any of these other amplification methodologies, i.e., by use of a particular set of reagents for that other amplification methodology. For example, the person of ordinary skill in the art will appreciate that a description herein made with respect to the RPA reaction in general (e.g., with respect to a set of reagents for an RPA reaction) will also apply to other isothermal nucleic acid amplification techniques (e.g., with respect to a set of reagents for an isothermal nucleic acid amplification reaction in general, or with respect to set of reagents for a LAMP reaction, a HDA reaction, a NEAR reaction, a NASBA reaction, an SDA reaction or a CPA reaction). Of course, the person of ordinary skill in the art will adapt particular process parameters, e.g., temperature, for the particular amplification reaction.

One embodiment of the disclosure is a device useful for performing concentration and amplification of a nucleic acid via ITP-enhanced RPA. The device comprises (i) a porous matrix having a first end and a second end opposing the first end, the first end and the second end defining a first axis, the porous matrix having a first fluid pathway having a first end and extending to a second end, (ii) a first electrode in conductive contact with the first end of the first pathway, and (iii) a second electrode in conductive contact with the second end of the first pathway. One example of such a device is shown in schematic view in FIG. 1. Device 100 includes a porous matrix 120 having a first end 122 and a second end 124 opposing the first end. The first end and the second end of the porous matrix define a first axis 123. The porous matrix includes a first fluid pathway 130 extending from a first end 132 to a second end 134. In this embodiment the first fluid pathway extends substantially along the direction of the first axis. The device also includes a first electrode 150 disposed adjacent the first end of the first pathway; and a second electrode 155 disposed adjacent the second end of the first pathway. For use in an ITP-enhanced RPA reaction, the device can also include (iv) a first fluid comprising a trailing electrolyte, disposed in the porous matrix within the first pathway, the trailing electrolyte comprising an ion and a counterion, (v) a second fluid comprising a leading electrolyte, disposed in the porous matrix within the first pathway, the leading electrolyte comprising an ion and a counterion, the ion of the leading electrolyte having a higher effective electrophoretic mobility than the ion of the trailing electrolyte, (vi) a set of RPA reaction reagents, disposed in the porous matrix within the first fluid pathway, and (vii) a nucleic acid, the nucleic acid having a higher effective electrophoretic mobility than the ion of the trailing electrolyte and a lower effective electrophoretic mobility than the ion of the leading electrolyte. The nucleic acid can initially be disposed, for example, adjacent the first end of the first fluid pathway between the electrodes, such that under isotachphoretic conditions it can migrate toward the second end of the first fluid pathway. For example, in the embodiment of FIG. 1, the device further includes a first fluid 140 and a second fluid 145. First and second electrodes 150 and 155, respectively, are positioned so that when the first and second liquids are disposed in the device as described below, the first electrode is in fluid communication with the first end of the first pathway, and the second electrode is in fluid communication with the second end of the first pathway.

Another embodiment of the disclosure is a method of concentrating and amplifying a nucleic acid via ITP-enhanced RPA (i.e., an ITP-enhanced RPA reaction). The method includes providing a device as described herein. The method also includes applying a voltage across the first electrode and the second electrode for a time sufficient to provide a first ITP plug comprising an amplification product. As the person of ordinary skill in the art will appreciate, the application of the voltage can substantially separate the nucleic acid from various other components of the matrix in which it is originally provided (e.g., blood, mucous, cell or urine components), focus (i.e., concentrate) the separated nucleic acids, and contact the nucleic acids with RPA reaction reagents, resulting in rapid amplification of the nucleic acid; the amplification product of the nucleic acid will be focused together with the nucleic acids from the original sample.

Figure 2:
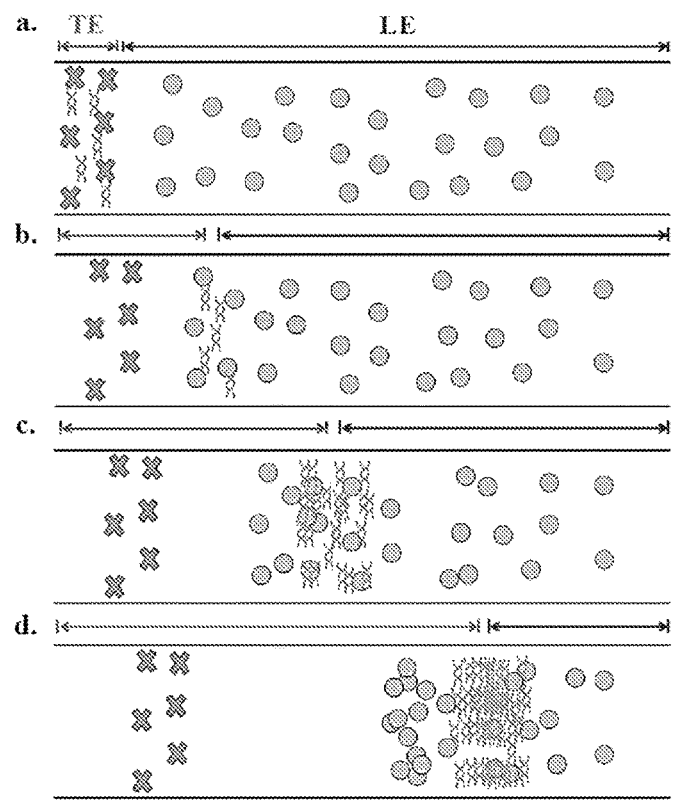
FIG. 2 shows a schematic view of an ITP enhanced RPA reaction according to one embodiment of the disclosure, in which (a) the nucleic acid (spirals) and contaminants (crosses) are initially mixed together in the first fluid comprising the trailing electrolyte (labeled TE) at one end of the first fluid channel and the RPA reaction reagents are included in the second fluid comprising the leading electrolyte (labeled LE), which fills the remainder of the channel, (b)

An example of a method for concentrating and amplifying a nucleic acid in a sample is shown in schematic cross-sectional view in FIG. 2. In the method of FIG. 2, a first fluid pathway of a provided device as described above is shown. The nucleic acid and contaminants are initially mixed together in the first fluid comprising the trailing electrolyte (labeled TE), which is disposed in the first fluid pathway adjacent its first end. The RPA reaction reagents are initially mixed with the second fluid comprising the leading electrolyte (labeled LE), which is disposed in the remainder of the first fluid channel. After the fluids are introduced, a voltage is applied across the first electrode and the second electrode, which serves to cause the nucleic acid to migrate toward the second end, contacting it with the RPA reagents to result in nucleic acid amplification, and focusing the nucleic acid along with its amplification products into an ITP plug. In certain desirable embodiments, one or more of the RPA reagents can be co-focused together with the nucleic acid in the ITP plug; this can allow for an even more rapid amplification of nucleic acid.

The person of ordinary skill in the art will appreciate that the first fluid, second fluid, RPA reaction reagents, and nucleic acid may be introduced to the provided device in different forms, combinations, and orders. In some embodiments, one or more reagents from the set of RPA reaction reagents are present in the second fluid. In some embodiments, one or more reagents from the set of RPA reaction reagents are present in the first fluid. In some embodiments, the nucleic acid is present in the first fluid. In some embodiments, the nucleic acid is included in the first fluid before the first fluid is introduced to the first fluid pathway. In other embodiments, the nucleic acid is introduced to the first fluid pathway separately from the first fluid, before, after, or simultaneously with the introduction of the first fluid to the first fluid pathway. In some embodiments, the second fluid is introduced to the first fluid pathway before the first fluid is introduced to the first fluid pathway.

In some embodiments, the second fluid is introduced to the first fluid pathway by contacting the second end of the first fluid pathway with the second fluid. This can be done, for example, by disposing an end of the device into a body of the second fluid, such that the second fluid is absorbed into the first fluid pathway at the second end thereof. In other embodiments, the second fluid is introduced to the first fluid pathway by dispensing the second fluid onto the first fluid pathway along the first axis (e.g., at the second end thereof). In other embodiments, the second fluid is introduced to the first fluid pathway via introduction of the second fluid to a reservoir in fluid communication with the second end of the first fluid pathway.

In some embodiments, the first fluid is introduced to the first fluid pathway by contacting the first end of the first fluid pathway with the first fluid. This can be done, for example, by disposing an end of the device into a body of the first fluid, such that the first fluid is absorbed into the first fluid pathway at the first end thereof. In other embodiments, the first fluid is introduced to the first fluid pathway by dispensing the first fluid onto the first fluid pathway along the first axis (e.g., at the first end thereof). In other embodiments, the first fluid is introduced to the first fluid pathway via introduction of the first fluid to a reservoir in fluid communication with the first end of the first fluid pathway.

Generally, at the beginning of the ITP process, the first fluid is disposed more toward the first end of the first fluid pathway than the second fluid.

In some embodiments, one or more of the reagents of the set of RPA reaction reagents are disposed within the porous matrix in a substantially dry form before the first fluid and the second fluid are introduced to the first fluid pathway. Accordingly, in certain embodiments, the methods described herein include dissolving or suspending the one or more dry form RPA reaction reagents in the first fluid and/or the second fluid. Similarly, in some embodiments, the leading electrolyte is disposed within the porous matrix in a substantially dry form in one or more zones of the first fluid pathway before the first fluid and the second fluid are introduced to the first fluid pathway. Accordingly, in certain embodiments, the methods described herein include dissolving the leading electrolyte to form the second fluid. And in some embodiments, the trailing electrolyte is disposed within the porous matrix in a substantially dry form in one or more zones of the first fluid pathway before the first fluid and the second fluid are introduced to the first fluid pathway. Accordingly, in certain embodiments, the methods described herein include dissolving the trailing electrolyte to form the first fluid.

The person of ordinary skill in the art will appreciate that the forms and order of addition of the RPA reaction reagents, nucleic acid, first electrolyte, and second electrolyte to the device described above may be combined in a number of ways. In one example, one or more of the reagents of the set of RPA reaction reagents are disposed within the porous matrix along the first fluid pathway in a substantially dry form, and the method includes dispensing the second fluid comprising the leading electrolyte onto the first fluid pathway and dissolving or suspending the one or more dry form RPA reaction reagents in the second fluid. The first end of the fluid pathway can be contacted with the first fluid comprising the trailing electrolyte and the nucleic acid, e.g., by disposing an end of the device into a body of the first fluid, such that the first fluid is absorbed into the first fluid pathway at the first end thereof. Alternatively, the method may include disposing an end of the device into a body of the second fluid comprising the leading electrolyte, such that the second fluid is absorbed into the first fluid pathway at the second end thereof, dissolving or suspending the one or more dry form RPA reaction reagents in the second fluid, and disposing an end of the device into a body of the first fluid comprising the trailing electrolyte and the nucleic acid, such that the first fluid is absorbed into the first fluid pathway at the first end thereof. Alternatively, the nucleic acid of either preceding embodiment may be introduced to the first fluid pathway separately from the first fluid, before, after, or simultaneously with the introduction of the first fluid to the first fluid pathway.

In another example, one or more of the reagents of the set of RPA reaction reagents are disposed in one or more zones of the first fluid pathway in substantially dry form, and the method includes contacting the second end of the second fluid pathway with the second fluid. This can be done, for example, by disposing an end of the device into a body of the second fluid comprising the leading electrolyte, such that the second fluid is absorbed into the first fluid pathway at the second end thereof, dissolving or suspending the one or more dry form RPA reaction reagents in the second fluid, and contacting the first end of the first fluid pathway with the first fluid comprising the trailing electrolyte and the nucleic acid, e.g., by disposing an end of the device into a body of the first fluid, such that the first fluid is absorbed into the first fluid pathway at the first end thereof. Alternatively, the nucleic acid may be introduced to the first fluid pathway separately from the first fluid, before, after, or simultaneously with the introduction of the first fluid to the first fluid pathway.

In another example, the leading electrolyte is disposed within the porous matrix along the first fluid pathway in a substantially dry form, wherein the method includes dispensing a solution comprising one or more of the reagents of the set of RPA reaction reagents onto the first fluid pathway, dissolving the leading electrolyte to form the second fluid, and contacting the first end of the first fluid pathway with the first fluid comprising the trailing electrolyte and the nucleic acid, e.g., by disposing an end of the device into a body of the first fluid, such that the first fluid is absorbed into the first fluid pathway at the first end thereof. Alternatively, the method may include contacting the second end of the first fluid pathway with a body of a fluid comprising one or more of the reagents of the set of RPA reaction reagents, e.g., by disposing an end of the device into the body of the fluid such that the fluid is absorbed into the first fluid pathway at the second end thereof, dissolving the leading electrolyte to form the second fluid, and contacting the first end of the first fluid pathway with the first fluid comprising the trailing electrolyte and the nucleic acid, e.g., by disposing an end of the device into a body of the first fluid comprising the trailing electrolyte and the nucleic acid, such that the first fluid is absorbed into the first fluid pathway at the first end thereof. Alternatively, the nucleic acid of either preceding embodiment may be introduced to the first fluid pathway separately from the first fluid, before, after, or simultaneously with the introduction of the first fluid to the first fluid pathway.

In another example, the leading electrolyte is disposed in one or more zones of the first fluid pathway in substantially dry form, wherein the method includes contacting the second end of the first fluid pathway with a fluid comprising one or more of the reagents of the set of RPA reaction reagents, e.g., by disposing an end of the device into a body of a fluid comprising one or more of the reagents of the set of RPA reaction reagents, such that the fluid is absorbed into the first fluid pathway at the second end thereof, dissolving the leading electrolyte to form the second fluid, and contacting the first end of the first fluid pathway with the first fluid comprising the trailing electrolyte and the nucleic acid, e.g., by disposing an end of the device into a body of the first fluid comprising the trailing electrolyte and the nucleic acid, such that the first fluid is absorbed into the first fluid pathway at the first end thereof. Alternatively, the nucleic acid may be introduced to the first fluid pathway separately from the first fluid, before, after, or simultaneously with the introduction of the first fluid to the first fluid pathway.

In another example, the trailing electrolyte is disposed in one or more zones of the first fluid pathway in substantially dry form, wherein the method includes contacting the first end of the first fluid pathway with a fluid comprising the nucleic acid, e.g., by disposing an end of the device into a body of a fluid comprising the nucleic acid, such that the fluid is absorbed into the first fluid pathway at the first end thereof, dissolving the trailing electrolyte to form the first fluid, and dispensing the second fluid comprising the leading electrolyte and one or more reagents of the set of RPA reaction reagents onto the first fluid pathway. Alternatively, the method may include contacting the first end of the first fluid pathway with a fluid comprising the nucleic acid, e.g., by disposing an end of the device into a body of a fluid comprising the nucleic acid, such that the fluid is absorbed into the first fluid pathway at the first end thereof, dissolving the trailing electrolyte to form the first fluid, and contacting the second end of the first fluid pathway with the second fluid comprising the leading electrolyte and one or more reagents of the set of RPA reaction reagents, e.g., by disposing an end of the device into a body of the second fluid, such that the second fluid is absorbed into the first fluid pathway at the second end thereof. Alternatively, the nucleic acid of either preceding embodiment may be introduced to the first fluid pathway separately from the first fluid, before, after, or simultaneously with the introduction of the first fluid to the first fluid pathway.

In another example, the leading electrolyte and one or more reagents of the set of RPA reaction reagents are disposed within the porous matrix along the first axis in a substantially dry form, wherein the method includes dispensing a solution onto the first fluid pathway along the first axis, dissolving the leading electrolyte and the one or more dry form RPA reaction reagents to form the second fluid, and contacting the first end of the first fluid pathway with the first fluid comprising the trailing electrolyte and the nucleic acid, e.g., by disposing an end of the device into a body of the first fluid, such that the first fluid is absorbed into the first fluid pathway at the first end thereof. Alternatively, the method may include contacting the second end of the first fluid pathway with a fluid, e.g., by disposing an end of the device into a body of a fluid, such that the fluid is absorbed into the first fluid pathway at the second end thereof, dissolving the leading electrolyte and the one or more dry form RPA reaction reagents to form the second fluid, and contacting the first end of the first fluid pathway with the first fluid comprising the trailing electrolyte and the nucleic acid, e.g., by disposing an end of the device into a body of the first fluid, such that the first fluid is absorbed into the first fluid pathway at the first end thereof. Alternatively, the nucleic acid of either preceding embodiment may be introduced to the first fluid pathway separately from the first fluid, before, after, or simultaneously with the introduction of the first fluid to the first fluid pathway.

In another example, the leading electrolyte and one or more reagents of the set of RPA reaction reagents are disposed in one or more zones of the first fluid pathway in substantially dry form, wherein the method includes contacting the second end of the first fluid pathway with the a fluid, e.g., by disposing an end of the device into a body of a fluid, such that the fluid is absorbed into the first fluid pathway at the second end thereof, dissolving the leading electrolyte and the one or more dry form RPA reaction reagents to form the second fluid, and contacting the first end of the first fluid pathway with the first fluid comprising the trailing electrolyte and the nucleic acid, e.g., by disposing an end of the device into a body of the first fluid, such that the first fluid is absorbed into the first fluid pathway at the first end thereof. Alternatively, the nucleic acid may be introduced to the first fluid pathway separately from the first fluid, before, after, or simultaneously with the introduction of the first fluid to the first fluid pathway.

In another example, the leading electrolyte and one or more reagents of the set of RPA reaction reagents are disposed within the porous matrix along the first axis in a substantially dry form and the trailing electrolyte is disposed in one or more zones of the first fluid pathway in substantially dry form, wherein the method includes dispensing a solution onto the first fluid pathway along the first axis, dissolving the leading electrolyte and the one or more dry form RPA reaction reagents to form the second fluid, and contacting the first end of the first fluid pathway with a fluid comprising the nucleic acid, e.g., by disposing an end of the device into a body of a fluid comprising the nucleic acid, such that the fluid is absorbed into the first fluid pathway at the first end thereof, dissolving the trailing electrolyte to form the first fluid. Alternatively, the method may include contacting the second end of the first fluid pathway with a fluid, e.g., by disposing an end of the device into a body of a fluid, such that the fluid is absorbed into the first fluid pathway at the second end thereof, dissolving the leading electrolyte and the one or more dry form RPA reaction reagents to form the second fluid, and contacting the first end of the first fluid pathway with a fluid comprising the nucleic acid, e.g., by disposing an end of the device into a body of the fluid comprising the nucleic acid, such that the fluid is absorbed into the first fluid pathway at the first end thereof, dissolving the trailing electrolyte to form the first fluid. Alternatively, the nucleic acid of either preceding embodiment may be introduced to the first fluid pathway separately from the first fluid, before, after, or simultaneously with the introduction of the first fluid to the first fluid pathway.

In another example, the leading electrolyte and one or more reagents of the set of RPA reaction reagents are disposed in a first set of one or more zones of the first fluid pathway in substantially dry form, and the trailing electrolyte is disposed in a second set of one or more zones of the first fluid pathway in substantially dry form, wherein the method includes contacting the second end of the first fluid pathway with a fluid, e.g., by disposing an end of the device into a body of a fluid, such that the fluid is absorbed into the first fluid pathway at the second end thereof, dissolving the leading electrolyte and the one or more dry form RPA reaction reagents to form the second fluid, and contacting the first end of the first fluid pathway with a fluid comprising the nucleic acid, e.g., by disposing an end of the device into a body of the first fluid comprising the nucleic acid, such that the fluid is absorbed into the first fluid pathway at the first end thereof, dissolving the trailing electrolyte to form the first fluid. Alternatively, the nucleic acid may be introduced to the first fluid pathway separately from the first fluid, before, after, or simultaneously with the introduction of the first fluid to the first fluid pathway.

The person of ordinary skill in the art will appreciate that various liquids can be dispensed in a variety of ways. In certain embodiments, a liquid (e.g., an electrolyte, a reagent solution, or a solvent therefor) can be disposed on the device in a sealed body, and dispensing the fluid (e.g., to provide the fluid to the porous matrix or to dissolve a dry or concentrated material already disposed in the porous matrix) can include opening the sealed body to allow the fluid to contact the porous matrix. The sealed body can be, for example, a pouch or "blister" of fluid as shown in FIG. 31; the body can be broken by puncturing, e.g., upon closing of a cover of the device. Accordingly, one embodiment of the disclosure is a device as described herein wherein the porous membrane lacks at least one of the leading electrolyte, the trailing electrolyte, and the set of isothermal nucleic acid amplification reagents at the dilution desired for the ITP-enhanced amplification process, and wherein the device further includes one or more sealed bodies bearing the desired fluids. For example, a sealed body bearing the leading electrolyte can be disposed adjacent the second end of the fluid pathway, such that when the sealed body is opened (e.g., by puncturing), the leading electrolyte flows into the porous matrix at the second end thereof. Similarly, a sealed body bearing the trailing electrolyte can be disposed adjacent the first end of the fluid pathway, such that when the sealed body is opened (e.g., by puncturing), the trailing electrolyte flows into the porous matrix at the first end thereof. One or more of the reagents of the set of isothermal nucleic acid amplification reagents can be disposed in a sealed body adjacent the fluid pathway, either together with one or both of the electrolytes or in a separate body. And in the cases where one or more of the electrolytes or reagents is in solid or concentrated form in the porous matrix, one or more sealed bodies of solvent can be provided. In use, the sealed bodies can be broken or punctured to start the flow of fluids and allow the ITP-enhanced amplification to proceed.

Various embodiments are described with respect to various materials provided in substantially dry form. The person of ordinary skill in the art will appreciate that in alternative embodiments, the corresponding materials can be provided in a liquid form, e.g., in a concentrated solution or suspension in porous matrix, which can be diluted with fluid to form the first fluid or the second fluid.

The nucleic acid can be provided to the first fluid pathway in a variety of methods. For example, as described above, it can be provided in the first fluid. In other embodiments of the methods and devices as described herein, the nucleic acid can be provided to the first fluid pathway at a location between the first and second ends thereof, for example, at a sample zone (which can be, e.g., defined by a window in a final packaged device). Notably, the nucleic acid can be provided from a solution or suspension having a relatively low concentration, e.g., as in a biological sample or a semi-purified version thereof; the devices and methods described herein can substantially concentrate and amplify the nucleic acid to provide for improved limits of detection in an assay. For example, in some embodiments of the methods and devices as described herein, the nucleic acid has a concentration that is at least about three, at least about four, or even at least about five orders of magnitude smaller than the concentration of the leading electrolyte in the second fluid, and a concentration at least about three, at least about four, or even at least about five orders of magnitude smaller than the concentration of the trailing electrolyte in the first fluid (e.g., each on the order of about three to about seven, about three to about six, about three to about five, about four to about seven, about four to about six, or about five to about seven orders of magnitude (e.g., when it is disposed in the porous matrix, or when it is disposed in the first fluid or the second fluid before being introduced to the porous matrix)). In certain embodiments, the concentration of the nucleic acid is at least one, at least two, or even at least three orders of magnitude larger in the ITP plug (e.g., when contacting a detection zone) than it is in the device before the ITP process. In certain embodiments, the concentration of the nucleic acid is at least one, at least two, or even at least three orders of magnitude larger in the ITP plug (e.g., when contacting a detection zone) than it is in a biological sample from which the nucleic acid is introduced to the device. Additionally, the nucleic acid can be provided as part of a complex matrix, and/or can be generated from an insufficiently mobile species by techniques such as complexation or reaction.

In the methods and devices as described herein, a variety of porous matrices can be used by the person of ordinary skill in the art. The porous matrix can have, for example, an average pore size in the range of about 0.5 to about 10 μm, e.g., in the range of about 0.5 to about 7 μm, about 0.5 to about 5 μm, about 0.5 to about 3 μm, about 1 to about 10 μm, about 1 to about 7 μm, about 1 to about 5 μm, about 1 to about 3 μm, about 3 to about 10 μm, about 3 to about 7 μm, about 3 to about 5 μm, or about 5 to about 10 μm, or about 0.1 μm to about 100 μm, or about 0.1 μm to about 10 μm, or about 1 μm to about 100 μm, or about 10 μm to about 100 μm. The porous matrix as described herein is desirably highly porous (e.g., at least about 65% porous, at least 70% porous, at least 75% porous, at least 80% porous, at least 85% porous, or even at least 90% porous, e.g., about 65% to about 90% porous, about 65% to about 95% porous, about 65% to about 98% porous, about 70% to about 90% porous, about 70% to about 95% porous, about 70% to about 98% porous, about 75% to about 90% porous, about 75% to about 95% porous, about 75% to about 98% porous, about 80% to about 90% porous, about 80% to about 95% porous, about 80% to about 98% porous, about 85% to about 90% porous, about 85% to about 95% porous, at about 85% to about 98% porous, about 90% to about 95% porous, or about 90% to about 98% porous). In some embodiments, the internal surface area ratio (i.e., the internal pore surface area per external apparent area) is in the range of about 50 to about 200, e.g., in the range of about 50 to about 150, about 50 to about 125, about 50 to about 100, about 75 to about 200, about 75 to about 150, about 75 to about 125, about 75 to about 100, about 100 to about 200, about 100 to about 150, or about 100 to about 125. The porous matrix for example, can be a paper or membrane material. For example, in some embodiments, the porous matrix is formed from nitrocellulose. In other embodiments, the porous matrix is formed from glass (e.g., glass fiber), nylon (e.g., nylon fiber), polyester, polyvinylidine fluoride, polycarbonate, polyethersulfone or cellulose acetate. In some embodiments, the porous matrix is a porous material (e.g., as described above, or filled with particulate matter or porous particulate matter) disposed within a microchannel or capillary; in such embodiments, the porous matrix can have the pore size, internal surface area ratio and/or porosity as described above.

The porous matrix can generally be formed to be relatively thin, e.g., in the range of about 100 μm to about 5 mm in thickness, e.g., about 500 μm to about 5 mm, about 1 mm to about 5 mm, about 100 μm to about 3 mm, about 500 μm to about 3 mm or about 1 mm to about 3 mm. In some embodiments, the length of the porous matrix from its first end to its second end (e.g., along its first axis) is in the range of about 5 mm to about 200 mm, e.g., in the range of about 5 mm to about 100 mm, about 5 mm to about 75 mm, about 5 mm to about 50 mm, about 5 mm to about 40 mm, about 5 mm to about 30 mm, about 10 mm to about 200 mm, about 10 mm to about 100 mm, about 10 mm to about 75 mm, about 10 mm to about 50 mm, about 10 mm to about 40 mm, about 10 mm to about 30 mm, about 20 mm to about 200 mm, about 20 mm to about 100 mm, about 20 mm to about 75 mm, about 20 mm to about 50 mm, about 20 mm to about 40 mm, or about 20 mm to about 30 mm. In some embodiments, the width of the porous matrix (e.g., in a direction perpendicular to the first axis or in a direction perpendicular to the direction of the first fluid pathway, for example, at the position of the detection zone as described below) is in the range of about 0.5 mm to about 30 mm, e.g., in the range of about 0.5 mm to about 25 mm, or about 0.5 mm to about 20 mm, or about 0.5 mm to about 15 mm, or about 0.5 mm to about 10 mm, or about 0.5 mm to about 5 mm, or about 1 mm to about 30 mm, or about 1 mm to about 25 mm, or about 1 mm to about 20 mm, or about 1 mm to about 15 mm, or about 1 mm to about 10 mm, or about 1 mm to about 5 mm. The porous matrix can, for example, be provided in a generally rectangular form.

In some embodiments, the length of the first fluid pathway from its first end to its second end is in the range of about 5 mm to about 200 mm, e.g., in the range of about 5 mm to about 100 mm, about 5 mm to about 75 mm, about 5 mm to about 50 mm, about 5 mm to about 40 mm, about 5 mm to about 30 mm, about 10 mm to about 200 mm, about 10 mm to about 100 mm, about 10 mm to about 75 mm, about 10 mm to about 50 mm, about 10 mm to about 40 mm, about 10 mm to about 30 mm, about 20 mm to about 200 mm, about 20 mm to about 100 mm, about 20 mm to about 75 mm, about 20 mm to about 50 mm, about 20 mm to about 40 mm, or about 20 mm to about 30 mm. In some embodiments, the width of the first fluid pathway (in a direction perpendicular to the direction of the first fluid pathway, for example, at the position of the detection zone as described below) is in the range of about 0.5 mm to about 30 mm, e.g., in the range of about 0.5 mm to about 25 mm, or about 0.5 mm to about 20 mm, or about 0.5 mm to about 15 mm, or about 0.5 mm to about 10 mm, or about 0.5 mm to about 5 mm, or about 1 mm to about 30 mm, or about 1 mm to about 25 mm, or about 1 mm to about 20 mm, or about 1 mm to about 15 mm, or about 1 mm to about 10 mm, or about 1 mm to about 5 mm.

Figure 1:
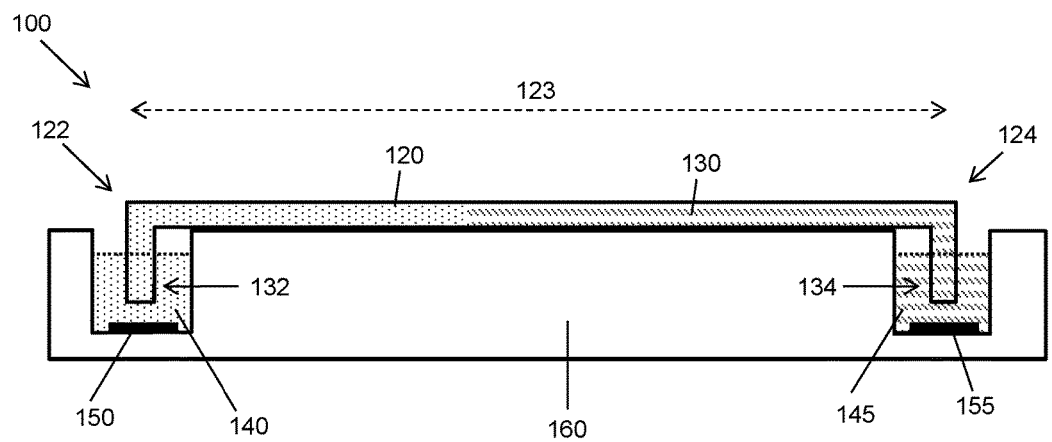
FIG. 1 shows a schematic cross-sectional view of a device according to one embodiment of the disclosure.

As described above, the first fluid pathway extends from a first end to a second end within the porous matrix. The first fluid pathway need not be particularly defined within the matrix, i.e., it need not be set off from the remainder of the matrix by any particular structures. In the device of FIG. 1, the first end 132 of the fluid pathway is disposed at the first end 122 of the porous matrix, and the second end 134 of the fluid pathway is disposed at the second end 124 of the porous matrix. In other embodiments, one or both of the first end and the second end of the fluid pathway is offset from the corresponding first or second end of the porous matrix. In certain embodiments, the first fluid pathway extends in substantially the same direction as the first axis (e.g., within 30 degrees, within 20 degrees, or even within 10 degrees of the first axis). In certain embodiments, the first fluid pathway follows a circuitous path, e.g., through a microchannel or capillary; such a configuration can allow for a longer first fluid pathway in an overall smaller device size.

The device of FIG. 1 further includes a substrate 160. The substrate 160 includes reservoirs 162 and 164, holding the first and second fluids, respectfully. The ends of the porous matrix are dipped in the reservoirs, allowing the first and second fluids to wick into the porous matrix along the first fluid pathway. Of course, the person of ordinary skill in the art will appreciate that the first and second fluids can be introduced to the first fluid pathway via a variety of structural arrangements and methods. Moreover, the person of ordinary skill in the art will appreciate that in some embodiments, no substrate is necessary; all necessary structures can be integrated onto the porous membrane or otherwise provided. For example, first and second reservoirs for the first and second fluids can be provided as separate structures, or the first and second fluids can be introduced to the first fluid pathway manually or via some other structure(s). For example, the fluid(s) and/or the nucleic acid can be introduced to the porous matrix through a top surface thereof. Reservoirs can be provided on the top surface of the porous matrix for this purpose, as shown in FIG. 7A. A reservoir can also be provided in the form of an absorbent material (e.g., sponge or an absorbent pad) configured to absorb liquid and contact it with the porous matrix, e.g., as shown in FIG. 9. Such an absorbent material can, for example, have a recess formed therein to allow for placement of a relatively large quantity of fluid in the sponge reservoir. The absorbent material can be formed, for example, from cellulose membrane or glass fiber.

The person of ordinary skill in the art will appreciate that the first and second electrodes can be provided in a variety of fashions. In some embodiments, the electrodes are fabricated directly in contact with the first fluid pathway (e.g., by being formed directly thereon, for example, by metal evaporation, screen printing or electrochemical deposition), or are positioned in contact with the first fluid pathway (e.g., by being clamped against the first fluid pathway), or are positioned in contact with a conductive fluid (e.g., the first or second fluid) that is in contact with the first fluid pathway. For example, the electrodes can be positioned in the reservoirs with the electrolyte and sample, as shown in FIG. 1. In certain alternative embodiments, the device can include a plurality of reservoirs at the first end of the first fluid pathway, the second end of the first fluid pathway, or both. When there is a second reservoir at an end of the fluid pathway, the electrode can be disposed in a separate reservoir from, for example, the sample, or from other organic or biochemical components. Separating the electrode from the sample prevents possible degradation of targets due to electrolysis reactions at the electrode surface. The fluidic connection between all reservoirs can established by having the porous matrix be in contact with each reservoir. This is shown in the partial schematic plan view of FIG. 36. Device 3600 includes a first reservoir 3671 and a second reservoir 3672 at the first end 3622 of porous matrix 3620, and a first reservoir 3673 and a second reservoir 3674 at the second end 3624 of porous matrix 3620, with the second reservoirs being disposed outside their respective first reservoirs with respect to the fluid pathway. A first electrode 3650 is disposed in the second reservoir 3672 at the first end of the porous matrix, and a second electrode 3655 is disposed in the second reservoir 3674 at the second end of the porous matrix. In use, first reservoir 3671 and second reservoir 3672 at the first end of the porous matrix can have trailing electrolyte disposed therein, with the sample (and, for example, any other electrolytically sensitive materials) disposed in the first reservoir 3671. Similarly, first reservoir 3673 and second reservoir 3674 at the second end of the porous matrix can have leading electrolyte disposed therein, with the any electrolytically sensitive materials disposed in the first reservoir 3673. This configuration can be u-shaped as shown in FIG. 36, or, for example, all reservoirs can be along the same horizontal line with a longer, straight strip of porous electrode. The porous electrode can, for example, be disposed on top of the reservoirs with tabs folded down to contact the reservoirs. As the person of ordinary skill in the art will appreciate, in some embodiments one of the ends of the device (e.g., an end where no sample or other electrolytically sensitive material is to be disposed in the reservoir) may only have a single reservoir.

As the person of ordinary skill in the art will appreciate, the electrodes need to be in conductive communication with either end of the first fluid pathway at the time that the separation and amplification via application of voltage is performed.

Each of the leading and trailing electrolytes includes an ion and a counterion. The leading and trailing electrolyte ions are anions. The leading and trailing electrolytes are selected such that the nucleic acid has a higher effective electrophoretic mobility than the ion of the trailing electrolyte and a lower effective electrophoretic mobility than the ion of the leading electrolyte. Thus, in the ITP process, the nucleic acid will concentrate at the boundary between the faster-moving leading electrolyte ions and the slower-moving trailing electrolyte ions. As the person of ordinary skill in the art will appreciate, effective mobility is a function of degree of dissociation of analytes which is typically a function of their dissociation constants (e.g., $K_a$), local pH and local ionic strength. The person of ordinary skill in the art will select first and second fluids and leading and trailing electrolytes such that the pH and ionic strength of the first and second fluids render them sufficiently conductive for ITP (for example, on the order of 5 µS/cm to about 50 mS/cm, e.g., about 10 µS/cm to about 1 mS/cm for trailing electrolytes, and about 1 to about 50 mS/cm for leading electrolytes) and that the nucleic acid is in a desired form (e.g., a desired ionic form). A detailed discussion on choice of an electrolyte system for ITP is provided, for example, in Everaerts, F. et al., Isotachophoresis: Theory, Instrumentation and applications; Elsevier, 1976, and Bagha, S. S. et al., *Electrophoresis* 2010, 31, 910-919, each of which is hereby incorporated herein by reference in its entirety.

In some embodiments, the pH of the first and/or second fluids is in the range of about 6.5 and about 9.5, e.g., about 7 to about 9, or about 7.5 to about 8.5, or the pH is about 7, or about 7.5, or about 8, or about 8.5, or about 9. In some embodiments, the ionic strength of the first and/or second fluids is in the range of about 1 to about 500 mM, e.g., about 5 to about 400 mM, or about 10 to about 350 mM, or about 25 to about 300 mM, or about 40 to about 250 mM, or about 50 to about 200 mM, or about 25 mM, or about 50 mM, or about 75 mM, or about 100 mM, or about 125 mM, or about 150 mM, or about 175 mM, or about 200 mM, or about 225 mM, or about 250 mM, or about 300 mM.

In some embodiments of the methods and devices as described herein, the difference between the effective mobilities of the ion of the leading electrolyte and the ion of the trailing electrolyte is at least about $5 \times 10^{-9}$ m$^2$V$^{-1}$s$^{-1}$, e.g., at least about $7.5 \times 10^{-9}$ m$^2$V$^{-1}$s$^{-1}$, or at least about $1 \times 10^{-8}$ m$^2$V$^{-1}$s$^{-1}$, or at least about $1.5 \times 10^{-8}$ m$^2$V$^{-1}$s$^{-1}$, or at least about $2 \times 10^{-8}$ m$^2$V$^{-1}$s$^{-1}$, or at least about $2.5 \times 10^{-8}$ m$^2$V$^{-1}$s$^{-1}$, or at least about $3.0 \times 10^{-8}$ m$^2$V$^{-1}$s$^{-1}$, or at least about $3.5 \times 10^{-8}$ m$^2$V$^{-1}$s$^{-1}$, or at least about $4.0 \times 10^{-8}$ m$^2$V$^{-1}$s$^{-1}$. For example, in some embodiments, the leading electrolyte is a strong acid, e.g., hydrochloric acid, nitric acid, phosphoric acid, or carbonic acid. In some embodiments, the trailing electrolyte is a weak acid, e.g., HEPES, serine, glycine, tricine, TAPS, MOPS, BES, ACES, MES, or MOPSO. Especially desirable trailing electrolytes include serine, glycine or tricine. In some embodiments, the trailing electrolyte is a weak base, e.g., Tris, Bis-Tris, imidazole, creatinine, pyridine, EACA, ammediol, ethanolamine. In some embodiments of the methods and devices as described herein, the counterion of the trailing electrolyte is the same as the counterion of the leading electrolyte. The leading and trailing electrolytes can be at any desired concentration in the first and second fluids, respectively. For example, in some embodiments, the concentration of the trailing electrolyte in the first fluid is in the range of about 1 µM to about 500 mM, e.g., about 100 µM to about 500 mM, or about 500 µM to about 500 mM, or about 1 mM to about 250 mM, or about 1 mM to about 100 mM, or about 5 mM to about 75 mM, or about 10 mM to about 50 mM, or about 1 mM, or about 5 mM, or about 10 mM, or about 20 mM, or about 30 mM, or about 40 mM, or about 50 mM, or about 60 mM, or about 75 mM, or about 100 mM. In some embodiments of the methods and devices as described herein, concentration of the leading electrolyte in the second fluid is in the range of about 1 mM to about 1 M, e.g., about 1 mM to about 750 mM, or about 1 mM to about 500 mM, or about 5 mM to about 400 mM, or about 10 mM to about 300 mM, or about 10 mM to about 200 mM, or about 25 mM to about 200 mM, or about 50 mM to about 200 mM, or the concentration is about 10 mM, or about 25 mM, or about 50 mM, or about 75 mM, or about 100 mM, or about 125 mM, or about 150 mM, or about 175 mM, or about 200 mM, or about 250 mM, or about 300 mM, or about 400 mM, or about 500 mM.

One example of a preferred set of electrolytes/buffers is 60 mM glycine/30 mM Tris in the first liquid, and 100 mM HCl and 200 mM Tris in the second liquid. A similar example uses 60 mM glycine as the trailing electrolyte, titrated with 5 mM Ba(OH)$_2$ or 10 mM NaOH. In certain embodiments, these concentrations can vary, e.g., 15-90 mM glycine, 5-50 mM Tris for the first liquid and 50-150 mM HCl and 100-300 mM Tris for the second liquid. The glycine as the trailing electrolyte can be replaced with serine or tricine at similar concentrations.

As various amplification reactions require magnesium ions, a magnesium source can be included in one or both of the first liquid or the second liquid, e.g., at concentrations of 2 mM-20 mM, with 10-15 mM (e.g., 12 mM) in the second liquid being especially desirable.

In certain embodiments of the methods and devices as described herein, other materials can be present in the first pathway (e.g., by being provided as part of the first and/or second fluids). Such materials can, for example, reduce the effects of electroosmotic flow, and can, for example, provide more rapid analysis, improved reproducibility, and resolution, for example, by coating the pore surface of the porous matrix. The additive can be, for example, a non-ionic surfactant or a non-ionic polymer, e.g., a polyvinyl alcohol) polymer, a poly(alkylene glycol) polymer, a polyethylene glycol (PEG), polyvinylpyrrolidone (PVP), TWEEN®20, TRITON™ X-100, polylactams, substituted polyacrylamide derivatives, and water-soluble methylhydroxyethyl derivatives of cellulose. The additive can be present in the device in a dry state (e.g., before the electrolytes and/or the fluids are added); or can be added with fluid when performing the assay (e.g., with one or more of the electrolytes and/or the first or second fluids). In some aspects, the concentration of the additive in the first and/or second fluid is in the range of about 0.01% to about 10% (w/v), e.g., about 0.01% to about 9%, or about 0.01% to about 8%, or about 0.02% to about 7.5%, or about 0.03% to about 7%, or about 0.04% to about 6%, or about 0.05% to about 5%, or about 0.06% to about 4.5%, or about 0.07% to about 4%, or the concentration is about 0.05%, or about 0.06%, or about 0.07%, or about 0.08%, or about 0.09%, or about 0.1%, or about 0.11%, or about 0.12%, or about 0.13%, or about 0.14%, or about 0.15%, or about 0.175%, or about 0.2%, or about 0.25%.

Other additives useful in nucleic acid polymerization reactions can be present in the first pathway (e.g., by being provided as part of the first and/or second fluids). Such additives include, for example, tetramethylammonium salts such as tetramethylammonium chloride and tetramethyl ammonium oxalate (e.g., 15-100 mM, to help reduce non-specific binding); dimethyl sulfoxide (e.g., 2-10%, to reduce secondary structure, especially in GC-rich structures); bovine serum albumin (e.g., 0.01-0.1 mg/mL, especially with samples containing amplification inhibitors such as melanin); betaine (0.1-3.5 M, preferably not in the form of an acid salt thereof, to reduce Tm and facilitate GC-rich region amplification, and to reduce duplex stability); and formamide (e.g., 1-5%, to reduce secondary structure, especially in GC-rich structures).

As used herein, the term "RPA reaction reagent" describes any protein, enzyme, oligonucleotide, biomolecule, small molecule, salt, or buffer that is required in an RPA reaction, or can be optionally included in an RPA reaction. In some embodiments, the RPA reaction reagents comprise core proteins, oligonucleotide primers, deoxynucleotides (dNTPs), dideoxynucleotides (ddNTPs), adenosine triphosphate (ATP), a magnesium source, crowding agents, buffer, and/or a reducing agent. In some embodiments, the RPA reaction reagents further comprise detection probes, additional proteins, creatine, and/or phosphocreatine.

In some embodiments, the core proteins of the RPA reaction reagents comprise a recombinase, a single-stranded DNA-binding protein (SSB), and a strand-displacing polymerase. In some embodiments, the recombinase is a uvsX recombinase and/or a uvsY recombinase. In some embodiments, the recombinase is a RecA recombinase. In some aspects, the concentration of the recombinase in the first and/or second fluid is in the range of about 100 µg/µL to about 3.5 µg/µL, e.g., about 250 µg/µL to about 3 µg/µL, or about 500 µg/µL to about 2 µg/µL, or about 750 µg/µL to about 1.5 µg/µL, or about 1 ng/µL to about 1 µg/µL, or about 1 ng/µL to about 900 ng/µL, or about 1 ng/µL to about 800 ng/µL, or about 5 ng/µL to about 700 ng/µL, or about 10 ng/µL to about 600 ng/µL, or about 20 ng/µL to about 500 ng/µL, or about 30 ng/µL to about 400 ng/µL, or about 40 ng/µL to about 400 ng/µL, or about 50 ng/µL to about 350 ng/µL, or about 50 ng/µL to about 300 ng/µL, or about 50 ng/µL to about 250 ng/µL, or about 50 ng/µL to about 200 ng/µL, or about 75 ng/µL to about 350 ng/µL, or about 10 ng/µL, or the concentration is about 50 ng/µL, or about 75 ng/µL, or about 100 ng/µL, or about 125 ng/µL, or about 150 ng/µL, or about 200 ng/µL, or about 250 ng/µL, or about 300 ng/µL, or about 350 ng/µL.

In some embodiments, the SSB is a gp32 protein. In some aspects, the concentration of the SSB in the first and/or second fluid is in the range of about 1 ng/µL to about 5 µg/µL, e.g., about 1 ng/µL to about 4 µg/µL, or about 1 ng/µL to about 3 µg/µL, or about 1 ng/µL to about 2 µg/µL, or about 1 ng/µL to about 1.5 µg/µL, or about 5 ng/µL to about 1.25 µg/µL, or about 10 ng/µL to about 1 µg/µL, or about 25 ng/µL to about µg/µL, or about 50 ng/µL to about 1 µg/µL, or about 75 ng/µL to about 1 µg/µL, or about 100 ng/µL to about 900 ng/µL, or about 125 ng/µL to about 900 ng/µL, or about 150 ng/µL to about 800 ng/µL, or the concentration is about 50 ng/µL, or about 100 ng/µL or about 150 ng/µL, or about 200 ng/µL, or about 300 ng/µL, or about 400 ng/µL, or about 500 ng/µL, or about 600 ng/µL, or about 700 ng/µL, or about 800 ng/µL, or about 900 ng/µL, or about 1 µg/µL.

In some embodiments, the strand-displacing polymerase is a Bsu polymerase and/or a Sau polymerse. In some aspects, the concentration of the strand-displacing polymerase is in the range of about 300 µg/µL to about 3 µg/µL, or about 400 µg/µL to about 2.5 µg/µL, or about 500 µg/µL to about 2 µg/µL, or about 500 µg/µL to about 1.5 µg/µL, or about 600 µg/µL to about 1 µg/µL, or about 700 µg/µL to about 900 ng/µL or about 750 µg/µL to about 750 ng/µL, or about 1 ng/µL to about 500 ng/µL, or about 5 ng/µL to about 400 ng/µL, or about 5 ng/µL to about 300 ng/µL, or about 10 ng/µL to about 250 ng/µL, or about 20 ng/µL to about 250 ng/µL, or about 25 ng/µL to about 200 ng/µL, or about 30 ng/µL to about 150 ng/µL, or the concentration is about 10 ng/µL, or about 20 ng/µL, or about 30 ng/µL, or about 40 ng/µL, or about 50 ng/µL, or about 75 ng/µL, or about 100 ng/µL, or about 125 ng/µL, or about 150 ng/µL, or about 175 ng/µL, or about 200 ng/µL.

In some embodiments, the oligonucleotide primers of the RPA reaction reagents comprise a forward and reverse primer for nucleic acid amplification. In some embodiments, the primers are about 30-35 nucleotides long. In some embodiments, long tracks of guanines at the 5' end of the primer (i.e., the first 3-5 nucleotides) are avoided in the primer sequence. In some embodiments, long tracks of pyrimidines at the 5' end of the primer are beneficial to amplification. In some embodiments, long tracks of cytidines at the 5' end of the primer are beneficial to amplification. In some embodiments, guanines at the 3' end of the primer (i.e., the last 3 nucleotides), are beneficial to amplification. In some embodiments, cytidines at the 3' end of the primer are beneficial to amplification. In some embodiments, a content of guanine and cytidine (i.e., GC content) above 70% is avoided in the primer sequence. In some embodiments, a GC content below 30% is avoided in the primer sequence. In some embodiments, the primer sequences are selected via screening of multiple primer sequence candidates. In some aspects, the concentration of the first and/or second oligonucleotide primer in the first and/or second fluid is in the range of about 5 nM to about 20 µM, e.g., about 10 nM to about 15 µM, or about 25 nm to about 10 µM, or about 50 nM to about 5 µM, or about 75 nM to about 4 µM, or about 100 nM to about 3 µM, or about 150 nM to about 2.5 µM, or about 200 nM to about 2 µM, or about 250 nM to about 1.5 µM, or about 300 nM to about 1 µM, or the concentration is about 100 nM, or about 150 nM, or about 200 nM, or about 250 nM, or about 300 nM, or about 350 nM, or about 400 nM, or about 450 nM, or about 500 nM, or about 550 nM, or about 600 nM, or about 750 nM, or about 1 µM, or about 1.5 µM.

In some aspects, the concentration of dNTPs and/or ddNTPS in the first and/or second fluid is in the range of about 1 µM to about 5 mM, e.g., about 5 µM to about 4 mM, or about 10 µM to about 3 mM, or about 20 µM to about 2 mM, or about 30 µM to about 1 mM, or about 40 µM to about 900 µM, or about 50 µM to about 800 µM, or about 75 µM to about 700 µM, or about 100 µM to about 600 µM, or about 125 µM to about 500 µM, or about 150 to about 400 µM, or the concentration is about 25 µM, or about 50 µM, or about 75 µM, or about 100 µM, or about 125 µM, or about 150 µM, or about 175 µM, or about 200 µM, or about 250 µM, or about 300 µM, or about 350 µM, or about 400 µM, or about 500 µM, or about 750 µM, or about 1 mM.

In some aspects, the concentration of ATP in the first and/or second fluid is in the range of about 10 µM to about 50 mM, e.g., about 50 µM to about 10 mM, or about 100 µM to about 10 mM, or about 250 µM to about 10 mM, or about 500 µM to about 10 mM, or about 500 µM to about 7.5 mM, or about 500 µM to about 5 mM, or about 750 µM to about 4.5 mM, or about 1 mM to about 4 mM, or about 1.5 mM to about 3.5 mM, or the concentration is about 500 µM, or about 750 µM, or about 1 mM, or about 1.25 mM, or about 1 mM, or about 1.5 mM, or about 2 mM, or about 2.5 mM, or about 3 mM, or about 3.5 mM, or about 4 mM, or about 4.5 mM, or about 5 mM. The person of ordinary skill in the art will appreciate that any ATP analog hydrolysable by a core protein of the RPA reaction reagents (e.g., a recombinase) may be used in addition to, or in place of ATP in the RPA reaction reagents.

In some embodiments, the magnesium source of the RPA reaction reagents comprises $MgCl_2$. In some embodiments, the magnesium comprises magnesium acetate (MgAc). In some aspects, the concentration of magnesium in the first and/or second fluid is in the range of about 100 µM to about 750 mM, e.g., about 250 µM to about 700 mM, or about 500 µM to about 600 mM, or about 750 µM to about 500 mM, or about 1 mM to about 400 mM, or about 5 mM to about 350 mM, or about 10 mM to about 350 mM, or about 25 mM to about 350 mM, or about 50 mM to about 350 mM, or about 75 mM to about 350 mM, or about 100 mM to about 350 mM, or about 125 mM to about 350 mM, or about 150 mM to about 350 mM, or about 1 mM to about 100 mM, or about 1 mM to about 75 mM, or about 1 mM to about 50 mM, or about 5 mM to about 25 mM, or the concentration is about 5 mM, or about 10 mM, or about 15 mM, or about 20 mM, or about 25 mM, or about 50 mM, or about 75 mM, or about 100 mM, or about 150 mM, or about 200 mM, or about 250 mM, or about 300 mM, or about 350 mM, or about 400 mM.

In some embodiments, the crowding agent of the RPA reaction reagents is one or more macromolecules. In some embodiments, the crowding agent is polyethylene glycol (PEG). In some aspects, the PEG has a molecular weight (MW) greater than 1 kDa, e.g., PEG 1450 or PEG 8000. In some aspects, the PEG has a MW greater than 10 kDa, e.g., PEG 15000, PEG 20000, or PEG 35000. In some embodiments, the crowding agent is Dextran. In some aspects, the Dextran has a molecular weight higher than 5 kDa, e.g., Dextran T5, Dextran T10, Dextran T20, Dextran T40, Dextran T70, Dextran T150, Dextran T250, or Dextran T500. In some embodiments, the crowding agent is trehalose. In some aspects, macromolecular clusters comprising more than one trehalose molecule can act as a crowding agent. In some embodiments, the crowding agent is FICOLL®, e.g., FICOLL® 70 or FICOLL® 400. In some embodiments, the crowding agent is bovine serum albumin (BSA). In some embodiments, the crowding agent is polyvinylpyrrolidone (PVP). In some aspects, the PVP has a MW greater than 100 kDa, e.g., 360 kDa. In some embodiments, the concentration of the crowding agent is in a range of about 0.1% to about 10% (w/v), or about 0.5% to about 9%, or about 1.0% to about 8%, or about 1.5% to about 7.5%, or about 1.5% to about 5%, or about 2.5% to about 7.5%, or the concentration is about 0.1%, or about 0.5%, or about 1%, or about 1.5%, or about 2%, or about 2.5%, or about 3%, or about 4%, or about 5%, or about 6%, or about 7%.

In some embodiments, the buffer of the RPA reaction reagents is Tris buffer. In some aspects, the concentration of the buffer in the first and/or second fluid is in the range of about 100 µM to about 200 mM, e.g., about 500 µM to about 175 mM, or about 1 mM to about 150 mM, or about 5 mM to about 150 mM, or about 10 mM to about 150 mM, or about 15 mM to about 150 mM, or about 25 mM to about 150 mM, or about 50 mM to about 150 mM, or about 75 mM to about 125 mM, or about 5 mM to about 100 mM, or about 5 mM to about 75 mM, or the concentration is about 5 mM, or about 10 mM, or about 15 mM, or about 20 mM, or about 30 mM, or about 40 mM, or about 50 mM, or about 60 mM, or about 70 mM, or about 80 mM, or about 90 mM, or about 100 mM, or about 110 mM, or about 120 mM, or about 130 mM. In some embodiments, the buffer of the RPA reaction reagents further comprises acetate, e.g., potassium acetate. In some aspects, the concentration of acetate in the first and/or second fluid is in the range of about 500 µM to about 1 M, e.g., about 750 µM to about 750 mM, or about 1 mM to about 500 mM, or about 10 mM to about 400 mM, or about 20 mM to about 300 mM, or about 30 mM to about 250 mM, or about 40 mM to about 200 mM, or about 50 mM to about 150 mM, or the concentration is about 30 mM, or about 40 mM, or about 50 mM, or about 60 mM, or about 70 mM, or about 80 mM, or about 90 mM, or about 100 mM, or about 110 mM, or about 120 mM, or about 130 mM, or about 140 mM, or about 150 mM, or about 175 mM, or about 200 mM.

In some embodiments, the reducing agent of the RPA reaction reagents is dithiothreitol (DTT). In some aspects, the concentration of the reducing agent in the first and/or second fluid is in a range of about 10 µM to about 100 mM, e.g., about 25 µM to about 100 mM, or about 50 µM to about 100 mM, or about 75 µM to about 100 mM, or about 100 µM to about 75 mM, or about 250 µM to about 50 mM, or about 500 µM to about 25 mM, or about 1 mM to about 10 mM, or the concentration is about 500 µM, or about 750 µM, or about 1 mM, or about 2 mM, or about 3 mM, or about 4 mM, or about 5 mM, or about 6 mM, or about 7 mM, or about 8 mM, or about 9 mM, or about 10 mM, or about 15 mM, or about 25 mM. The person of ordinary skill in the art will appreciate the reducing agent may be any compound capable of enabling the activity of a core protein of the RPA reaction reagents (e.g., a SSB).

In some embodiments, the RPA reaction reagents may further comprise a reverse transcriptase. In some aspects, inclusion of a reverse transcriptase allows for the amplification of a ribonucleic acid by the core proteins of the RPA reaction reagents in an ITP enhanced RPA reaction. In some aspects, the amount of reverse transcriptase included in the first and/or second fluid is in the range of about 0.1 U to about 10 U, e.g., 0.1 U to about 9 U, or about 0.25 to about 8 U, or about 0.5 to about 7 U, or about 0.75 to about 6 U, or about 1 to about 5 U, or about 1 to about 4 U, or about 1 to about 3 U, or the amount is about 0.5 U, or about 0.75 U, or about 1 U, or about 1.25 U, or about 1.5 U, or about 1.75 U, or about 2 U, or about 2.25 U, or about 2.5 U, or about 3 U.

In some embodiments, the RPA reaction reagents may further comprise an endonuclease. In some embodiments, the endonuclease is an nfo endonuclease IV. In some embodiments, the RPA reaction reagents may further comprise a DNA glycosylase. In some embodiments, the DNA glycosylase is an fpg 8-oxoguanine DNA glycosylase. In some embodiments, the RPA reaction reagents may further comprise an exonuclease. In some embodiments, the exonuclease is an exoIII exonuclease. In some embodiments, the RPA reaction reagents may further comprise a creatine kinase. In some aspects, the concentration of the endonuclease, DNA glycosylase, and/or exonuclease in the first and/or second fluid is in the range of about 600 µg/µL to about 2 µg/µL, e.g., about 1 ng/µL to about 1 µg/µL, or about 5 ng/µL to about 750 ng/µL, or about 10 ng/µL to about 500 ng/µL, or about 20 ng/µL to about 400 ng/µL, or about 30 ng/µL to about 300 ng/µL, or about 40 ng/µL to about 250 ng/µL, or about 50 ng/µL to about 200 ng/µL, or about 60 ng/µL to about ng/µL to about 150 ng/µL, or the concentration is about 10 ng/µL, or about 20 ng/µL, or about 30 ng/µL, or about 40 ng/µL, or about 50 ng/µL, or about 60 ng/µL, or about 80 ng/µL, or about 90 ng/µL, or about 100 ng/µL, or about 110 ng/µL, or about 120 ng/µL, or about 130 ng/µL, or about 140 ng/μL, or about 150 ng/μL, or about 175 ng/μL, or about 200 ng/μL, or about 250 ng/μL.

In some embodiments, the RPA reaction reagents may further comprise one or more detection probes, for example, a fluorescence detection probe or a lateral flow sandwich assay detection probe. The person of ordinary skill in the art will appreciate that the detection probe may be any protein, oligo- or polynucleotide, calorimetric reagent, nanoparticle, or small molecule capable of providing a detectable signal upon exposure to a nucleic acid amplification product.

In some embodiments, the fluorescence detection probe comprises an oligonucleotide with homology to the target amplicon that contains an abasic nucleotide analogue (e.g., a tetrahydrofuran residue) which replaces a nucleotide in the target sequence flanked by a fluorophore and a corresponding quencher group, wherein any fluorescent signal generated by the fluorophore will normally be quenched by the quencher located 2-4 bases 3' to the fluorophore. In some aspects, pairing of the detection probe oligonucleotide to the target amplicon presents a substrate for an exonuclease, e.g., an exoIII exonuclease, which can cleave the probe at the abasic nucleotide analogue position, separating the fluorophore and quencher and generating a fluorescent signal.

In other embodiments, the fluorescence detection probe comprises an oligonucleotide homologue to the target amplicon that is modified at the 5'-end with a quencher group and that contains a fluorophore label coupled to an abasic nucleotide analogue 4 to 5 nucleotides downstream of the quencher (i.e., at position 5 or 6). In some aspects, pairing of the detection probe oligonucleotide to the target amplicon presents a substrate for a DNA glycosylase, e.g., an fpg 8-oxoguanine DNA glycosylase, which can cleave the probe at the abasic nucleotide analogue position, separating the fluorophore and quencher and generating a fluorescent signal.

In some aspects, the concentration of the oligonucleotide fluorescence detection probe in the first and/or second fluid is in the range of about 1 nM to about 5 μM, e.g., about 5 nM to about 1 μM, or about 10 nM to about 900 nM, or about 20 nM to about 800 nM, or about 30 nM to about 700 nM, or about 40 nM to about 600 nM, or about 50 nM to about 500 nM, or about 60 nM to about 400 nM, or about 70 nM to about 300 nM, or about 75 nM to about 200 nM, or about 75 nM to about 150 nM, or the concentration is about 30 nM, or about 40 nM, or about 50 nM, or about 60 nM, or about 70 nM, or about 80 nM, or about 90 nM, or about 100 nM, or about 110 nM, or about 120 nM, or about 130 nM, or about 140 nM, or about 150 nM, or about 175 nM, or about 200 nM, or about 250 nM.

In other embodiments, the fluorescence detection probe comprises an intercalating dye, e.g., SYBR®, SYTO®, POPO™, TOTO®, DAPI, PICOGREEN®, RIBOGREEN®, OLIGREEN®, cyanine, and ethidium bromide. In some aspects, the concentration of the oligonucleotide fluorescence detection probe in the first and/or second fluid is in the range of about 10 nM to about 50 μM, e.g., about 50 nM to about 40 μM, or about 100 nM to about 30 μM, or about 200 nM to about 20 μM, or about 300 nM to about 15 μM, or about 400 nM to about 10 μM, or about 500 nM to about 9 μM, or about 600 nM to about 8 μM, or about 700 nM to about 7 μM, or about 800 nM to about 6 μM, or about 900 nM to about 5 μM, or about 1 μM to about 4 μM, or about 1 μM to about 3 μM, or about 1 μM to about 2 μM, or the concentration is about 500 nM, or about 600 nM, or about 700 nM, or about 800 nM, or about 900 nM, or about 1 μM, or about 1.1 μM, or about 1.2 μM, or about 1.3 μM, or about 1.4 μM, or about 1.5 μM, or about 1.6 μM, or about 1.7 μM, or about 1.8 μM, or about 1.9 μM, or about 2 μM, or about 2.1 μM, or about 2.25 μM, or about 2.5 μM, or about 3 μM, or about 3.5 μM, or about 4 μM, or about 5 μM.

In other embodiments, the lateral flow sandwich assay detection probe comprises an oligonucleotide homologous to the target sequence which incorporates a 5'-antigenic label (e.g., a carboxyfluorescein group (FAM)), and an internal abasic nucleotide analogue. In one example, the oligonucleotide is used in a configuration in which the opposing amplification primer is labelled at its 5' end with another antigenic label (e.g., a biotin). Pairing of the detection probe oligonucleotide to the target amplicon presents a substrate for an endonuclease, e.g., an nfo endonuclease IV, generating a new 3'-hydroxyl group that can act as a priming site for polymerase extension. In some aspects, the amplicon produced by the processed probe and the 5'-labeled amplification primer will effectively co-join the two antigenic residues in one DNA molecule. In some aspects, the concentration of the oligonucleotide lateral flow sandwich assay detection probe in the first and/or second fluid is in the range of about 1 nM to about 5 μM, e.g., about 5 nM to about 1 μM, or about 10 nM to about 900 nM, or about 20 nM to about 800 nM, or about 30 nM to about 700 nM, or about 40 nM to about 600 nM, or about 50 nM to about 500 nM, or about 60 nM to about 400 nM, or about 70 nM to about 300 nM, or about 75 nM to about 200 nM, or about 75 nM to about 150 nM, or the concentration is about 30 nM, or about 40 nM, or about 50 nM, or about 60 nM, or about 70 nM, or about 80 nM, or about 90 nM, or about 100 nM, or about 110 nM, or about 120 nM, or about 130 nM, or about 140 nM, or about 150 nM, or about 175 nM, or about 200 nM, or about 250 nM.

In some embodiments, the RPA reaction reagents may further comprise creatine and/or phosphocreatine. In some aspects, the concentration of creatine and/or phosphocreatine in the first and/or second fluid is in the range of about 500 μM to about 500 mM, e.g., about 750 μM to about 300 mM, or about 1 mM to about 250 mM, or about 5 mM to about 200 mM, or about 10 mM to about 150 mM, or about 15 mM to about 100 mM, or about 20 mM to about 75 mM, or the concentration is about 1 mM, or about 5 mM, or about 10 mM, or about 15 mM, or about 20 mM, or about 25 mM, or about 30 mM, or about 40 mM, or about 50 mM, or about 60 mM, or about 70 mM, or about 80 mM, or about 90 mM, or about 100 mM, or about 125 mM.

A variety of RPA reagent systems are known in the art and are commercially available. The person of ordinary skill in the art will select a suitable set of RPA reagents for the methods and devices described herein.

In some embodiments, the porous matrix of the provided device includes in the first fluid pathway a detection zone. The detection zone can be configured to provide a variety of types of measurements. For example, the detection zone can include a detection substance that will interact (e.g., via reaction, binding, or coordination) with the nucleic acid and/or detection probe to provide some detectable change, e.g., a color change, chemi- or bioluminscence or a darkening, or a change that is detectable using any of a variety of instrumental techniques, e.g., colorimetric, spectrophotometric, fluorescence or electrochemical detection). The detection substance can be, for example, anchored to the material of the porous matrix (e.g., through chemical bonding), as would be apparent to the person of ordinary skill in the art. Of course, in other embodiments, the detection substance is not anchored to the material of the porous matrix. The detection substance can be, for example, a small molecule, a colorimetric reagent, a nanoparticle, an oligo- or polypeptide (e.g., a protein), or an oligo- or polynucleotide. The detection zone can thus be configured from an assay such as an immunoassay, an ELISA, a sandwich assay or a nucleotide binding assay. In other embodiments, no particular detection substance need be present; in some embodiments, a variety of techniques can be used to detect the nucleic acid (e.g., colorimetric, spectrophotometric, fluorescence or electrochemical detection). The methods described herein can thus include contacting the first ITP plug with the detection zone. The person of ordinary skill in the art will appreciate that virtually any detection scheme useful in lateral flow assays or microfluidic-based assays can be applied to the present devices.

Thus, the methods described herein can include transmitting the first ITP plug to the detection zone, and detecting the nucleic acid and/or detection probe in the detection zone. (See, e.g., FIG. 3 and FIG. 4, in which the dashed lines indicate the first fluid pathway). In certain embodiments, the device can include an optical readout system configured to perform an optical measurement on the detection zone; and the method can include performing an optical measurement on the detection zone after contacting the first ITP plug therewith. In some aspects, the optical readout system comprises an image sensor, e.g., a CCD sensor or a CMOS sensor, such as that of a camera-equipped mobile phone (See, e.g., "C" of FIG. 4 and "B" of FIG. 5). In some aspects, the optical readout system comprises an LED-based excitation source.

For example, assay techniques such as immunoassays, sandwich assays, and competitive binding assays can be used to identify the presence and amount of a nucleic acid biomolecule. In one such embodiment, a species that binds the nucleic acid or detection probe (e.g., a complimentary or anti-biomolecule) is deposited on porous matrix in the detection zone. The nucleic acid biomolecule binds to an indicator that has a binding species (e.g., a complimentary or anti-biomolecule) on one side and an indicator species on the other side (e.g., metal or polymer nanoparticle, fluorescence label, enzyme that induces chemiluminesence). The indicator could be mixed with the nucleic acid or one of the electrolytes so these are already bound when they are being concentrated by ITP. The concentrated nucleic acid biomolecule that is bound to the indicator reacts with the binding species in the detection zone, and in this way forms a "sandwich" on the membrane (see, e.g., FIG. 3). In certain embodiments, the indicator species is visible; in such cases, a visible line or spot formed in the detection zone indicates presence of nucleic acid. In other embodiments, the indicator species is not visible as a colorimetric line, but instead can be detected via fluorescence or chemiluminesence. The person of ordinary skill in the art will adapt other detection schemes for use with ITP-concentrated material. In one example, a nucleic acid can be detected using DNA hybridization assays, with an immobilized oligonucleotide in the detection zone. Other methods of detection can be used, such as electrochemical or capacitive detection (e.g. field effect). For example, the detection zone can include one or more electrodes that are functionalized with specific biomolecules; or one or more electrodes for the performance of cyclic voltammetry to detect the presence of the nucleic acid through some IV curve signature.

As the person of ordinary skill in the art will appreciate, the detection zone can also include a control substance, configured to provide a detectable change when the assay is performed even in the absence of the nucleic acid and/or detection probe, and thus provide a control to the assay. Thus, in certain embodiments, the control substance and the detection substance can be provided adjacent to one another in the detection zone, with a detectable change at the site of the control substance being indicative of the assay working correctly. As an alternative, two different fluorescent tags can be used to provide a control. A control fluorescent tag can be used to detect a known, control amplification reaction (e.g., amplification of a separate known control nucleic acid substrate, provided, for example, as part of the set of amplification reagents), and a test fluorescent tag can be used to detect the target nucleic acid. If the two different fluorescent tags fluoresce at different wavelengths, a comparison of fluorescence intensities can be used to provide the desired external control, and/or to normalize the fluorescence intensity measured for the test fluorescent tag.

In some embodiments, the difference between the effective mobilities of the ion of the leading electrolyte and the ion of the trailing electrolyte is at least about $5\times10^{-9}$ $m^2V^{-1}s^{-1}$, e.g., at least about $7.5\times10^{-9}$ $m^2V^{-1}s^{-1}$, or at least about $1\times10^{-8}$ $m^2V^{-1}s^{-1}$, or at least about $1.5\times10^{-8}$ $m^2V^{-1}s^{-1}$, or at least about $2\times10^{-8}$ $m^2V^{-1}s^{-1}$, or at least about $2.5\times10^{-8}$ $m^2V^{-1}s^{-1}$, or at least about $3.0\times10^{-8}$ $m^2V^{-1}s^{-1}$, or at least about $3.5\times10^{-8}$ $m^2V^{-1}s^{-1}$, or at least about $4.0\times10^{-8}$ $m^2V^{-1}s^{-1}$. In some aspects, the effective mobility of the ion of the leading electrolyte is at least about $1\times10^{-8}$ $m^2V^{-1}s^{-1}$, e.g., at least about $2\times10^{-8}$ $m^2V^{-1}s^{-1}$, or at least about $3\times10^{-8}$ $m^2V^{-1}s^{-1}$, at least about $4\times10^{-8}$ $m^2V^{-1}s^{-1}$, or at least about $5\times10^{-8}$ $m^2V^{-1}s^{-1}$, or at least about $6\times10^{-8}$ $m^2V^{-1}s^{-1}$, or at least about $7\times10^{-8}$ $m^2V^{-1}s^{-1}$, or at least about $8\times10^{-8}$ $m^2V^{-1}s^{-1}$. In some aspects, the effective mobility of the trailing electrolyte is at most about $8\times10^{-8}$ $m^2V^{-1}s^{-1}$, e.g., at most $7\times10^{-8}$ $m^2V^{-1}s^{-1}$, or at most $6\times10^{-8}$ $m^2V^{-1}s^{-1}$, or at most $5\times10^{-8}$ $m^2V^{-1}s^{-1}$, or at most $4\times10^{-8}$ $m^2V^{-1}s^{-1}$, or at most $3\times10^{-8}$ $m^2V^{-1}s^{-1}$, or at most $2\times10^{-8}$ $m^2V^{-1}s^{-1}$, or at most $1\times10^{-8}$ $m^2V^{-1}s^{-1}$.

In some embodiments, the difference between the effective mobilities of the ion of the leading electrolyte and the nucleic acid is at least about $1\times10^{-9}$ $m^2V^{-1}s^{-1}$, e.g., at least about $2\times10^{-9}$ $m^2V^{-1}s^{-1}$, or at least about $3\times10^{-9}$ $m^2V^{-1}s^{-1}$, or at least about $4\times10^{-9}$ $m^2V^{-1}s^{-1}$, or at least about $5\times10^{-9}$ $m^2V^{-1}s^{-1}$. In some embodiments, the difference between the effective mobilities of the ion of the trailing electrolyte and the nucleic acid is at least about $1\times10^{-9}$ $m^2V^{-1}s^{-1}$, e.g., at least about $2\times10^{-9}$ $m^2V^{-1}s^{-1}$, or at least about $3\times10^{-9}$ $m^2V^{-1}s^{-1}$, or at least about $4\times10^{-9}$ $m^2V^{-1}s^{-1}$, or at least about $5\times10^{-9}$ $m^2V^{-1}s^{-1}$.

In some embodiments, the effective mobility of one or more reagents of the set of RPA reaction reagents is less than the effective mobility of the ion of the trailing electrolyte. In some aspects, one or more reagents of the set of RPA reaction reagents with an effective mobility less than that of the ion of the trailing electrolyte are included in the first fluid, wherein a first ITP plug comprising a nucleic acid with an effective mobility greater than that of the ion of the trailing electrolyte will migrate in the opposite direction of the one or more reagents of the set of RPA reaction reagents, thereby contacting the nucleic acid with the RPA reagents (e.g., by introducing the one or more reagents of the set of RPA reaction reagents into the first ITP plug) in order to allow amplification to proceed.

In some embodiments, the effective mobility of one or more reagents of the set of RPA reaction reagents is greater than the effective mobility of the ion of the trailing electrolyte and lower than the effective mobility of the nucleic acid. In some aspects, one or more reagents of the set of RPA reaction reagents with an effective mobility less than that of the nucleic acid are included in the first fluid, wherein the nucleic acid (e.g., in the form of a first ITP plug) will overcome one or more reagents of the set of RPA reaction reagents (e.g., in the form of a plug of RPA reagent) migrating in the same direction, thereby contacting the one or more reagents of the set of RPA reaction reagents with the nucleic acid and allowing amplification to proceed.

In some embodiments, the effective mobility of one or more reagents of the set of RPA reaction reagents is greater than the effective mobility of the nucleic acid and lower than the effective mobility of the leading electrolyte. In some aspects, one or more reagents of the set of RPA reaction reagents with an effective mobility greater than that of the nucleic acid are included in the second fluid, such that the nucleic acid (e.g., as a first ITP plug comprising the nucleic acid) will be overcome by one or more reagents of the set of RPA reaction reagents (e.g., in the form of a plug of RPA reagents) migrating in the same direction, thereby contacting the one or more reagents with the nucleic acid (e.g., in a first ITP plug) and allowing amplification to proceed. Alternatively, the one or more reagents of the set of RPA reaction reagents with an effective mobility greater than that of the nucleic acid are included in the first fluid, such that the nucleic acid (e.g., as a first ITP plug comprising the nucleic acid) will be overcome by the one or more reagents of the set of RPA reaction reagents (e.g., in the form of a plug of RPA reagents) migrating in the same direction, thereby contacting the one or more reagents with the nucleic acid (e.g., in a first ITP plug) and allowing amplification to proceed.

The person of ordinary skill in the art will appreciate that the effective mobilities of the RPA reaction reagents and the location of the RPA reaction reagents in the provided device (e.g., the first or second fluid), may be different from each other, provided that the RPA reaction reagents required to allow amplification to proceed are simultaneously disposed in the same area as the nucleic acid for a period of time and at concentrations sufficient to allow amplification to proceed. In one example, the oligonucleotide primers and detection probe of the RPA reaction reagents are included in the first fluid further comprising the trailing electrolyte and the nucleic acid, while the remaining reagents of the set of RPA reaction reagents are included in the second fluid further comprising the leading electrolyte. The person of ordinary skill in the art will determine how best to distribute the RPA reagents based, for example, on their relative mobilities as compared to the relative mobilities of the nucleic acid, the leading electrolyte and the trailing electrolyte.

In order to practice the ITP step, the first and second electrodes can be coupled to an electrical voltage or power source. The electrical voltage or power source can be configured to provide sufficient voltage and current for the desired ITP process. The electric voltage or power source, the first electrode, and the second electrode can be, for example, configured so that current flows along the first fluid pathway in a direction that is substantially parallel to the direction of flow of the first fluid along the first fluid pathway (e.g., within 30 degrees, within 20 degrees, or even within 10 degrees). The voltage or power source can be, for example, a constant voltage or current source. The voltage can be applied, for example, such that a constant voltage is applied across the electrodes, or a constant current passes between the electrodes. Notably, the voltage or power source need not be a plug-in source like a laboratory source; it can advantageously be based on a battery. For example, in some embodiments, the voltage or power source includes a battery and a voltage multiplier circuit. The battery can be, for example, a portable battery like a button battery, a cylindrical battery like a AA, AAA, C or D battery, a lantern battery, or a 9V battery. In some embodiments, the voltage or power source includes a mobile device, e.g., a mobile phone (See, e.g., "B" and "C" of FIG. 5). Of course, other voltage or power sources can be used, e.g., a flexible battery, a capacitor, a small fuel cell, solar powered, liquid or solid pouch battery. The voltage or power source can be, for example, configured to apply between 1-2500 volts to the device and/or configured to provide a current flow between $10^{-6}$ to 50 milliamperes to the device.

In some embodiments, the voltage applied to the provided device is a voltage sufficient to provide a first ITP plug. In some aspects, the voltage is in the range of about 1-2500 Volts, for example, between about 1-2000 Volts, or between about 5-1500 Volts, or between about 10-1000 Volts, or between about 15-500 Volts, or between about 25-300 Volts, or between about 50-200 Volts, or the voltage is about 15 Volts, or about 25 Volts, or about 50 Volts, or about 75 Volts, or about 100 Volts, or about 125 Volts, or about 150 Volts, or about 175 Volts, or about 200 Volts, or about 500 Volts.

In some embodiments, the voltage applied provides a current flow in the range of about $10^{-6}$ to about 50 milliamperes to the provided device, e.g., about $10^{-5}$ to about 25 milliamperes, or between about $10^{-4}$ to about 10 milliamperes, or between about $10^{-3}$ to about 10 milliamperes, or between about $10^{-2}$ to about 10 milliamperes, or between about 0.1 to about 10 milliamperes, or between about 0.2 to about 9 milliamperes, or between about 0.3 to about 7.5 milliamperes, or between about 0.5 to about 5 milliamperes, or the current flow is about 0.1 milliamperes, or about 0.25 milliamperes, or about 0.5 milliamperes, or about 1 milliamperes, or about 2 milliamperes, or about 3 milliamperes, or about 4 milliamperes, or about 5 milliamperes, or about 6 milliamperes, or about 7 milliamperes, or about 8 milliamperes, or about 9 milliamperes, or about 10 milliamperes.

In some embodiments, the voltage applied provides a current flow sufficient to provide Joule heating of the first fluid pathway to a temperature of at least about 20° C. In some aspects, the temperature is at least about 25° C., or at least about 30° C., or at least about 35° C., or at least about 40° C., or the temperature is in the range of about 20° C. to about 75° C., of about 20° C. to about 65° C., or about 25° C. to about 50° C., or about 30° C. to about 45° C., or about 25° C. to about 45° C., or about 30° C. to about 75° C., or about 30° C. to about 65° C. The person of ordinary skill in the art will appreciate that RPA can proceed at a temperature as low as about 25° C. to about 30° C., e.g., in the range of about 25° C. to about 50° C., or about 30° C. to about 45° C., which can be maintained solely by Joule heating of the provided device. Other amplification techniques have different temperature requirements. For example, many isothermal amplification reactions are conveniently run at 55-65° C.; in certain embodiments, Joule heating can provide such heat. Of course, in other embodiments, separate heat control is used, e.g., a separate heater such as a heat tape can be laminated to or otherwise operatively coupled to the device. When higher temperatures are used, devices described with respect to FIGS. 6-13 can be especially useful in maintaining solvent in the liquids in the device.

In certain embodiments, the device includes a temperature sensor in thermal communication with the first fluid pathway; in such embodiments, the applied voltage can be adjusted to provide more or less Joule heating to arrive at a desirable temperature. In certain embodiments, a thermally-conductive sheet is disposed along and in thermal communication with the first fluid pathway, in order to distribute and dissipate heat; desirably, a non-electrically conductive layer separates the first fluid pathway from any electrically conductive layers of the thermally-conductive sheet.

In certain desirable embodiments, there is substantially no temperature cycling during the application of voltage necessary to provide the amplification product, i.e., once the device heats to a desired reaction temperature, the temperature remains within 5° C. of that temperature.

In some embodiments, the reaction of the RPA reaction reagents with the nucleic acid provides a nucleic acid amplification product wherein the concentration or nucleic acids is increased relative to the nucleic acid concentration in the device (e.g., in the first ITP plug) before contact of the RPA reaction reagents with the nucleic acid. In some aspects, the nucleic acid concentration is increased by a factor of at least about 100, or at least about 500, or at least about 1000, or at least about 2500, or at least about 5000, or at least about 7500, or at least about 10000, or at least about 25000, or at least about 50000, or at least about 75000, or at least about 100000, or at least about 250000, or at least about 500000, or is increased by a factor in the range of about 100 and about 1000000, or about 1000 and about 100000, or about 5000 and about 50000. The person of ordinary skill in the art will appreciate that the focusing of the nucleic acids and the amplification of the nucleic acids can occur sequentially or simultaneously, depending on the relative positioning of the materials in the device. For example, the nucleic acid can in some embodiments be substantially focused into an ITP plug before amplification. Alternatively, the focusing and the amplification can happen substantially simultaneously.

In certain embodiments, applying the voltage forms a second ITP plug comprising one or more reagents of the set of INAA reaction reagents in a higher concentration than the one or more reagents in the first and/or second fluids outside of the second ITP plug. Bu One problem with prior art isotachophoretic methods and devices is the drying out of the electrolyte fluids, especially in configurations in which the porous matrix is open to the atmosphere. Accordingly, in one embodiment of the methods and devices as described herein, the porous matrix includes a first portion disposed generally along the first fluid pathway (e.g., along the first axis), the first portion having a first lateral edge and a second lateral edge opposing the first lateral edge, and at least one tab extending from the first lateral edge of the first portion. An example of such a porous matrix is shown in schematic plan view in FIG. 6. Porous matrix 320 includes a first portion 322 having a first lateral edge 325 and a second lateral edge 326 opposing the first lateral edge. Porous matrix 320 also includes a tab 327 that extends from the first lateral edge 325 of the first portion. The porous matrix can further include at least one tab extending from the second lateral edge; in the embodiment of FIG. 6, a tab 328 extends from second lateral edge 326. The tabs in the embodiment of FIG. 6 are formed at generally right angles to the strip-shaped first portion, forming a generally cruciform shape. Of course, in other embodiments, the one or more tabs can be formed at some other angle with the first fluid pathway (or the first axis), e.g., an angle between about 45° and about 90° to the first fluid pathway (or the first axis). The one or more tabs can have a width that is, for example, in the range of about 20% to about 150% (e.g., about 50%) of the width of the first portion. In certain embodiments, the one or more tabs are positioned in the range of about ⅕ of the way to about ¼ the way (e.g., about ⅓) from the first end to the second end of the porous matrix. While in the embodiment of FIG. 6, the tabs are disposed toward the first end of the porous matrix, the person of ordinary skill in the art will understand that a tab can be placed anywhere along the porous matrix in fluid communication with the first fluid pathway.

Each tab can be operatively coupled to a source of a third fluid, e.g., by being dipped into or otherwise fed by a reservoir of the third fluid. In certain embodiments of the methods described herein, the fluid is introduced into the second pathway, then from the second pathway to the first pathway (e.g., through capillary action) as the first pathway evaporates liquid due to Joule heating. The one or more tabs can thus provide a third fluid to ensure that the first pathway remains sufficiently wet for the isotachophoretic method. In certain embodiments, the third fluid is desirably substantially free of the leading electrolyte or the trailing electrolyte. In other embodiments, the third fluid includes one or more of the leading electrolyte and the trailing electrolyte. In certain embodiments, the third fluid includes or consists of water (e.g., deionized water). The third fluid can be, for example, substantially pure water, or can include additives such as buffers and polymeric species as described above.

In certain embodiments of the devices and methods as described herein, the device includes a substantially water-impermeable cover disposed over the porous matrix. The water-impermeable cover can also modulate the effects of Joule heating by trapping water in the porous matrix. The impermeable cover can, for example, be formed in contact with the porous matrix, e.g., as a coating or layer disposed thereon. In such embodiments, the substantially water-impermeable cover can have a window formed therein to allow for the application of a sample including the nucleic acid into the first fluid pathway. In other embodiments, the substantially water-impermeable cover can be formed as part of a chamber in which the porous matrix is disposed. Such a chamber can, for example, be closed over the porous matrix at any time, e.g., either before or after the first fluid, the second fluid, and/or the nucleic acid is disposed in the first fluid pathway. As the person of ordinary skill in the art will appreciate, all fluids described herein are desirably substantially aqueous fluids (e.g., in which the solvent is at least 85%, at least 90%, at least 95%, or even at least 99% water).

In certain embodiments, the porous matrix is disposed in a casing. The casing can be, for example, closeable, such that a sample (and any of the first, second and third fluids that are not already contained within the casing) may be added then the casing closed. The casing can help to protect the reservoirs and the porous matrix from contamination and spilling, and can also protect the user from electric shock during operation. In certain embodiments, the casing is resiliently closed, so that it cannot in normal operation be reopened. The device can be configured such that the closing of the casing initiates the application of electric voltage and starts the isotachophoresis, e.g., by the closing of a switch or the contact of electrodes. In other embodiments, the isotachophoresis can be initiated by the application of one or more of the fluids to the device. For example, the device can be configured such that the application of the first liquid or the second liquid to the device can complete a circuit and thus initiate a sequence of commands by a control circuit, including the application of the electric field. The casing can also include reservoirs for any of the first second and third fluids (e.g., molded into the casing), and can include an aperture for the loading of a nucleic acid sample onto the porous matrix in the first fluid pathway thereof, as well as a window for viewing the results of the assay (e.g., as discussed in more detail below). One example of such a device, similar in appearance to existing pregnancy tests, is shown in FIGS. 7A and 7B, in an open and closed state, respectively.

Another embodiment of the devices as described herein can be configured as a substantially flexible device. For example, in one embodiment, the device includes a flexible battery, upon which a flexible porous matrix is disposed. The first and second electrode can be operatively coupled to the battery. The device can include a flexible section in which the battery and the porous matrix are not constrained from flexing. One example of a flexible device is shown in schematic cross-sectional view in FIG. 8. In this device, a porous matrix 520 (e.g., nitrocellulose or glass fiber membrane) is substrate-bonded or otherwise fabricated on a flexible battery 580, such that the device has a flexible zone 581. Any type of fuel battery or fuel cell can be used as the "battery" as described herein, e.g., a flexible battery, flow battery, microfluidic fuel cell, or capacitor. In the device of FIG. 8, the battery is operatively coupled to an electronic circuit 582 configured to provide the desired voltage and current flow to the isotachophoretic process. The electronic circuit can, for example, be controlled by the user, for example, by a button, or can be activated by application of the first or second liquid. At either end, the device can include any structure as described herein for application of the first or second liquid. For example, the device can have one or more reservoirs (e.g., cup shaped) formed in fluid communication with the porous matrix for application of the first and second liquids. Alternatively, the device can include an absorbent pad, optionally with a reservoir formed therein to serve as a location to hold a suspended drop of first or second liquid (i.e., as shown in FIG. 8 by reference numerals 583 and 584). In such devices, the electrodes might be embedded in the absorbent pads or be physically placed inside the punched reservoir in the absorbent pad. The nucleic acid can be added, for example, as part of the first liquid (i.e., with the trailing electrolyte), or through a separate spot on the porous matrix (not shown in FIG. 8). The device of FIG. 8 also includes a water-impermeable cover 585 disposed over the porous matrix. The cover can include a window or opening 586 formed therein for viewing the results of the assay (as described in more detail below).

Another example of a device is shown in cross-sectional view in FIG. 9. This embodiment is built on a flexible battery 690; amplifier and microcontroller 692 can be actuated by the user by flexible switch 694 (as is commonly used in electronic devices). The electronic components as described herein, can, for example, be fabricated on a flexible substrate. The porous matrix 620 is disposed on the flexible battery; absorbent pads 683 and 684 can be used to apply first and second fluids to the device. In this embodiment, the device includes a substantially water-impermeable layer 685 on top of the porous matrix to minimize water loss.

Real-world samples are often provided as exceedingly dilute solutions. Accordingly, in certain embodiments, it can be desirable to provide a relatively high amount of sample to the isotachophoresis device or method. Described herein are various methods and structures that can be used by the person of ordinary skill in the art to provide relatively large sample sizes (for example, in excess of about 100 µL, e.g., up to about 300 µL, up to about 500 µL, or even up to about 1 mL) to the isotachophoretic devices and methods described herein. For example, in one embodiment, an absorbent pad is disposed on the porous matrix at the first end of the fluid pathway, the absorbent pad being in fluid communication with the first pathway, as shown in cross-sectional schematic view in FIG. 10. Dashed lines with arrows represent the electric field lines. The high porosity and void volume of the absorbent pad can allow for addition of a large sample volume to the device. With respect to each of the fluids, a device can include, for example, only an absorbent pad (e.g., as shown in FIG. 9), only a reservoir, or both an absorbent pad and a reservoir. In another embodiment, a reservoir can be constructed (e.g., from a wax or a polymer) on the top surface of the porous matrix at the first end of the first fluid pathway, the reservoir being in fluid communication with the first pathway. The reservoir can have an opening (e.g., at the top thereof) to allow for addition of sample. Wax printing is widely used on paper-microfluidic devices to construct channels and barriers in a simple way and with low cost; such methods can be adapted for use here. Moreover, the wax reservoir can be easily sealed by the casing of the test kit and may allow addition of more sample compared to use of an absorbent pad. A device including a wax reservoir is shown in schematic cross-sectional view in FIG. 11A and in schematic plan view in FIG. 11B.

Another approach to increase the sample volume is to increase the surface area of the porous matrix at the first end of the first fluid pathway (e.g., at the first end of the porous matrix). Thus, the area in which nucleic acid is exposed to the electric field is larger, thereby allowing more nucleic acid to be concentrated in the first ITP plug. Accordingly, in certain embodiments, a first portion of porous matrix has a first zone and a second zone, the first zone being disposed more toward the first end of the porous matrix than the second zone, the first zone having a substantially greater average width than the second zone (i.e., excluding any tabs extending from the first portion thereof). For example, the width of the first zone can be in the range of about 1.5 to about 10 times the width of the second zone. Desirably, the first ITP plug is present in the second zone during operation of the device. FIGS. 12 and 13 are schematic plan views of two examples of porous matrices, in which dashed lines with arrows represent the electric field lines. The person of ordinary skill in the art will appreciate that the absorbent pad and reservoirs described with respect to FIGS. 10, 11A and 11B can advantageously be used in embodiments with increases surface area at the first end of the first fluid pathway. Moreover, as shown in FIG. 13, it can be desirable to include one or more tabs (e.g., as described above with respect to FIG. 6) in order to help mitigate evaporation. In other embodiments (e.g., when the nucleic acid is added on the leading electrolyte side of the device), the first zone is disposed more toward the second end of the porous matrix than the second zone; the device can otherwise be as described above.

It can also be desirable to provide for sample filtration in order to remove relatively large species (e.g., whole cells, large biomolecules) from the sample before it is provided to the porous matrix. This can be especially useful with respect to clinical samples such as whole blood. For example, when the sample is to be added to the device by providing it directly to the porous matrix (i.e., not via a reservoir, for example, through an absorbent pad as described above), a filtration membrane can be disposed on the porous matrix (e.g., on an absorbent pad). The sample can be dropped onto the filtration membrane, which filters large species (e.g. whole cells and large biomolecules) while allowing blood serum with the target nucleic acid to wick through to the porous matrix. Vivid™-brand plasma separation membranes and other polysulfone membranes can be especially useful as such a filtration membrane. An example of such a device is shown in cross-sectional view in FIG. 37.

Various devices described above are described with respect to the use of a single porous matrix. In other embodiments, multiple separate porous matrices can be used. For example, in the device shown in schematic plan view in FIG. 38A, and in the photographic top view of FIG. 38B, a test strip of porous matrix can be provided separately from a control strip of porous matrix, with both having ends dipped into electrolyte reservoirs as described above. The test strip can contains primers and probe to detect the target nucleic of interest, while the control strip contains primers and probe that will detect a control molecule that is added to the reaction in known quantities. The control output can be used to monitor the efficiency of the reaction and/or to normalize the test output for quantification. FIG. 38C is a photograph of fluorescence from both strips after an ITP-enhanced RPA experiment as described herein.

EXAMPLES

The Examples that follow are illustrative of specific embodiments of the invention, and various uses thereof. They are set forth for explanatory purposes only, and are not to be taken as limiting the invention. The person of ordinary skill in the art will appreciate that the experimental details described herein can be applied, as appropriate, to the methods and devices described more generally above.

Example 1. ITP Enhanced RPA Reaction Chemistry and Protocol

This example describes the reaction chemistry and protocol for one embodiment of ITP-enhanced RPA. The general protocol of this example is:
(1) Create TE solution
(2) Create LE solution
(3) Rehydrate dry form RPA reaction reagents with LE solution, primers, and probe
(4) Add rehydrated RPA reaction reagents to glass fiber strip near TE reservoir
(5) Add non-pellet LE solution to LE reservoir
(6) Add TE (with or without target) to TE reservoir
(7) Seal petri dish lid with electrodes inserted into TE and LE reservoirs (cathode in TE reservoir, anode in LE reservoir)
(8) Optionally set sealed dish on hot plate at 38° C.
(9) Apply 100 V across membrane and monitor reaction fluorescence
TE solution components:
30 mM Tris,
60 mM glycine
0.1% polyvinylpyrrolidone (PVP, 360,000 Da)
0.1% Triton-X 100
pH 8.9
Nucleic acid target (or no target for negative controls)
LE solution components:
200 mM Tris
100 mM HCl
12 mM of MgCl2
5% polyethylene glycol (PEG, 1450 Da)
0.1% PVP
0.1% Triton-X 100
pH 8.1
45 µL of the LE solution is combined with primers and probe that will amplify and detect the nucleic acid sequence. The LE/primers/probe solution is used to rehydrate dry form RPA reaction reagents (e.g., a TwistDx (Cambridge, UK) RPA pellet). The rehydrated RPA reaction reagents (50 µL total) consists of:
approximately 1× LE buffer
500 nM of forward and reverse oligonucleotide primers for nucleic acid amplification,
120 nM of sequence-specific fluorescence indicator probe, and
1× rehydrated RPA reaction reagents containing all of the enzymes, nucleotides, and other biomolecules required for amplification using RPA.

The rehydrated RPA reaction reagents are split in half (2×25 µL) so that two experiments (a positive and negative control) can be performed. (Of course, in other embodiments, the entire 50 µL pellet solution, or any other desirable amount, can be added to the strip for a single test.) 25 µL of the rehydrated RPA reaction reagents are added to the glass fiber strip (30 mm long×3.5 mm wide, Millipore) near the TE reservoir and wets approximately half of the glass fiber strip. The LE reservoir is then filled with 120 µL of standard LE solution (not containing primers, probes, nucleotides, or core proteins), a portion of which wets the remainder of the glass fiber that was not wet by the rehydrated pellet solution. 100 µL of TE (with or without the nucleic acid) is then added to the TE reservoir. At this point, the glass fiber strip is fully wetted, both TE and LE reservoirs are full, and the glass fiber strip has established a fluidic connection between the two reservoirs. The lid to the dish is then placed on top to seal the reaction, and embedded electrodes in the lid are inserted into the TE and LE reservoir, as shown in FIG. 14.

The sealed dish containing the glass fiber with LE, TE, and RPA reaction components is optionally set onto a hotplate (38° C.) and the portion of the electrodes sticking outside of the dish are connected to an external voltage supply (in this example, a Keithley 2410 1100V SOURCEMETER®). 100 V is applied to the paper strip with a current compliance of 1.5 mA, i.e., if the current goes above 1.5 mA, the applied voltage will drop lower than 100 V so that the max power of the system is P=(100V)(1.5 mA)=150 mW. As ITP operation proceeds, the current will drop as the TE solution begins to fill the paper due to its lower conductivity compared to the LE and the voltage will raise until 100V. As the nucleic acid migrates toward the second end of the substrate, it concentrates to form an ITP plug, and contacts the RPA reagents (i.e., target, enzymes, primers, etc.) such that the RPA reaction proceeds (i.e., when the nucleic acid is present in the TE). The RPA reagents can, in some cases, focus together with the nucleic acid. For example, FIGS. 26 and 27, described below, demonstrate co-focusing of the nucleic acid and the RPA reagents; such substantial fluorescence would not be detected in the absence of substantial co-focusing. FIG. 30, described below, demonstrates that it is possible to co-focus reagents such as proteins and primers with nucleic acids in an ITP plug. And FIG. 21, described below, demonstrates that the results of the simulation of FIG. 30 are replicable via experiment, as relatively faster nucleic acids and relatively slower proteins are co-focused into the same ITP plug. The reaction creates amplicons determined by the forward and reverse primers. These amplicons are detected via a sequence specific probe that creates a fluorescent signal upon binding to the amplicon.

In this example, this fluorescent signal is monitored using a microscope with excitation at ~480 nM and emission at ~515 nM. The generated fluorescence is integrated over time using Matlab code and used to create plots such as those shown in FIGS. 15-16, 21.

Example 2. ITP Enhanced LE Concentration

FIG. 15 shows positive and negative control experiments of ITP-enhanced RPA nucleic acid detection with varying amounts of HCl/Tris leading electrolyte (LE) concentrations. The tested HCl/Tris concentrations were 100/200 mM, 120/240 mM, and 140/280 mM, at pH 8.1. Other than the HCl/Tris content, the experiment was carried out according to Example 1. These results show that the 100/200 mM LE concentration of the Example 1 protocol gives the best amplification efficiency for the positive control reactions.

Example 3. ITP Enhanced TE Concentration

FIG. 16 shows positive and negative control experiments of ITP enhanced RPA nucleic acid detection with varying amounts of TE concentrations. The numbers shown in FIG. 16 correspond to various glycine/Tris concentrations (mM) in the TE. The tested concentrations were 30 mM glycine/15 mM Tris, 60/30 mM, and 90/45 mM, all at pH 8.9. Other than the glycine and Tris content in the TE, the experiment was carried out according to Example 1. The focusing of the ITP plug was highly dependent on TE concentration—focusing generally improved as TE concentration decreased. The amplification curves followed this trend—the amplification improved with decreasing TE concentration, indicating that ITP focusing efficiency is likely playing a role in amplification. The 90/45 mM TE showed no amplification, likely due to poor stacking, and had slightly less intensity than the negative controls.

Example 4. Composition of Electrolyte System and Reaction Chemistry

FIG. 17 shows RPA reactions conducted without ITP enhancement (i.e., "tube format" RPA) with various ionic strengths at pH 8. The "positive control" line shows a TwistDx (Cambridge, UK) reaction buffer mixed with the RPA reaction reagents and nucleic acids of Example 1, while the "negative control" line shows the TwistDx reaction buffer mixed with the RPA reaction reagents of Example 1, but without nucleic acids. The other lines show experiments containing various amount of ITP compatible HCl/Tris buffer (i.e., the LE/buffer) with the overall ionic strength of the solution denoted. These results show that ionic strengths in the range of 145-175 mM give the best amplification efficiency for the tube format RPA, while ionic strengths of <130 mM or >200 mM partially or entirely inhibited the reaction.

The dependence on ionic strength of the amplification reaction was further shown in the ITP enhanced RPA format. ITP enhanced RPA experiments, conducted according to Example 1, that varied the HCl/Tris and $Mg^{2+}$ concentrations in the LE/buffer and found that the reaction efficacy (the signal-to-noise ratio of positive versus negative experiments) was highly dependent upon both the HCl/Tris concentration, as well as the overall ionic strength contributed by both HCl/Tris and $Mg^{2+}$. FIG. 18 shows analysis of variance (ANOVA) results indicating the importance of HCl/Tris (referred to as LE in the figure) and overall ionic strength (referred to as Mg*LE in the figure). This data shows that higher HCl/Tris (LE/buffer) concentrations are better for detecting nucleic acids (higher SNR), which is likely due to better focusing during ITP operation. However, raising the LE/buffer concentration for better signal-to-noise ratio is also dependent on the $Mg^{2+}$ concentration due to ionic strength constraints, i.e., raising LE/buffer concentration requires lowering $Mg^{2+}$ concentrations to stay within the limit of ionic strength shown previously.

Example 5. Joule Heating from Applied Electrical Current

While the ideal temperature range for tube format RPA reactions is 37-42° C., it may be run as low as 25° C., although the reaction kinetics are much slower at this temperature. ITP-enhanced RPA may be run without an external heater at room temperature (20° C.) with comparable or faster reaction kinetics than a standard assay at 37-42° C. This faster reaction rate is likely due to a combination of enhanced reaction kinetics due to the high reactant concentrations inside of the ITP plug, as well as the reaction experiencing internal Joule heating due to the flow of electrical current through the substrate and liquid. Joule heating is the heat generated by electric power in units of power per unit volume, $w = E \cdot I/S = I^2/\sigma \cdot S$, where E is the electric field, I is the electrical current, S is the cross sectional area of channel, and $\sigma$ is the solution conductivity. Dissipation of this generated heat is dependent on factors including substrate thermal conductivity, substrate area and thickness, and the thermal conductivity of the solution. High Joule heating and poor heat dissipation may lead to internal temperature rise inside of the channel.

The internal temperature rise of the provided device of Example 1 was studied using infrared (IR) thermal imaging, and it was found that the electrical current provides significant heating. FIG. 19 shows the approximate temperature of the ITP plug where the amplification reaction was occurring, which was tracked using a colorimetric dye, for ITP operation at 100 V (A-D) and 200V (E-H) and a standard LE/TE electrolyte composition. Under these conditions, the average temperature of the ITP plug as it migrates across the paper strip is approximately 30-34° C. for 100 V and 39-54° C. for 200 V. Different temperature ranges can be achieved depending on the applied electric field strength, the composition of the ITP electrolytes, and the dimensions of the glass fiber strip. This internal heating can be used as the heating source for an amplification reaction, removing the need for external heating.

These results demonstrate the ability to amplify a nucleic acid sequence without any external heating using ITP enhanced RPA. FIG. 20 shows experimental results of an ITP enhanced RPA reaction run according to Example 1 at 20° C., without any external heat, and at 38° C., with external heat supplied by a hotplate. The positive and negative reactions for each case showed no significant differences in reaction rate, overall intensity, or signal-to-noise ratio. The most notable difference between the experimental conditions is the time required for amplification. Without external heating, the ITP enhanced RPA reaction can be run at higher electric fields than ITP enhanced RPA with external heat because there is less risk of an internal temperature above the upper limit of 42° C. for RPA reactions. This tolerance for higher electric fields with no external heating allows for faster concentrating and migration of reagents within the ITP plug, and as a result, faster amplification. The ability to adjust electric field, solution conditions, and substrate geometry to control for heating allows reactions to be run at a wide variety of operating temperatures using only applied electrical power.

Example 6. ITP Model Experiments

ITP was carried out using conditions similar to those of Example 1 (e.g., 100/200 mM HCl/Tris and 60/30 mM glycine/Tris electrolytes) on a sample of (a) ALEX-AFLUOR® 488 dye (AF488), (b) a sample of AF488-labeled IgG proteins, and (c) a sample of both AF488 and AF488-labeled IgG proteins. In this example, AF488 simulated a nucleic acid, while the AF488-labeled IgG proteins simulated the RPA mixture. The area under the curve of the y-averaged intensity profile of the AF488 fluorescence was integrated and normalized to the total fluorescence intensity of the AF488 curve. The results, provided in FIG. 21, showed that the integrated fluorescence intensity of the ITP plug of sample (c) was higher than that of the ITP plug of sample (a) or sample (b), indicating that both AF488 and AF488-labeled IgG proteins were present in the ITP plug. These results demonstrated that, despite the low mobility of the IgG protein, AF488 and IgG proteins can be focused together into an ITP plug, meaning nucleic acids and RPA reagents can also similarly be co-focused.

Example 7. ITP Enhanced RPA with Fluorescent Probes

ITP enhanced RPA was carried out according to Example 1, without external heat, with ~10 initial copies of a nucleic acid included in the TE, and with fluorescent probes included in the LE. The y-averaged fluorescence intensity at time points of (a) 75 s, (b) 150 s, (c) 200 s, and (d) 240 s are shown in FIG. 22. The integrated fluorescence intensities of each time point (a)-(d) versus time are shown in FIG. 23. These results demonstrated that the nucleic acid increased approximately exponentially with time, and that ITP enhanced RPA achieved significant amplification within four minutes.

Example 8. ITP Enhanced RPA vs Tube RPA

The integrated and normalized fluorescence intensities versus time for tube format RPA reactions carried out in the presence of fluorescent probes at 38° C. (external heat provided) with (a) 0 copies, (b) 30 copies, and (c) 300 copies of nucleic acid were compared to the fluorescence intensities of ITP enhanced RPA carried out according to Example 1, with (d) 0 copies and (e) 10 copies of nucleic acid included in the TE, fluorescent probes included in the LE, and without external heat provided (22° C.). These results, shown in FIG. 24, demonstrate that ITP enhanced RPA is able to achieve exponential amplification within 3 or 4 minutes, without external heat, with only 10 initial copies of a nucleic acid, in contrast with tube format RPA, which was unable to provide exponential amplification of even 30 copies at an optimal, externally heated temperature of 38° C.

Example 9. ITP Enhanced RPA with Components Removed

ITP enhanced RPA was carried out according to Example 1, with nucleic acid included in the TE and fluorescence probes included in the LE, without external heat, and also without either (a) nucleic acid, (b) $Mg^{2+}$, (c) oligonucleotide primers. The fluorescence of runs (a)-(c) were validated against an ITP enhanced RPA reaction including nucleic acid, $Mg^{2+}$, and oligonucleotide primers. The results, given in FIG. 25, show that negligible fluorescence in runs without nucleic acid or oligonucleotide primers, which are essential components of the amplification reaction, and significantly decreased fluorescence in runs without $Mg^{2+}$, which serves to enhance the RPA reaction rate.

Example 10. ITP Enhanced RPA with HIV-1 DNA

ITP enhanced RPA was carried out according to Example 1, with 10 copies/μL HIV-1 DNA nucleic acid included in the TE and fluorescence probes included in the LE, without external heat. Sequential fluorescence images were collected over 180 seconds (see, FIG. 26), show both migration of the ITP plug and a significant increase in fluorescence intensity, a result of the amplification of the nucleic acid. FIG. 27 shows the integrated fluorescence intensities at each time point shown in FIG. 26 (and additional time points) compared to a similar reaction carried out without the nucleic acid.

Example 11. ITP of Whole Milk

ITP of was carried out according to Example 1, with a complex nucleic acid sample (whole milk) included in the TE and fluorescent probes included in the LE, without external heat. As shown in FIG. 28, the nucleic acids of the complex sample focused selectively at the LE/TE interface, while the inhibiting substances of the complex sample (e.g., macromolecules, cations, etc.) trailed behind the ITP plug. This technique can be used in conjunction with an isothermal amplification technique as described herein to provide for actual amplification of the nucleic acid.

Example 12. ITP Enhanced RPA with Blood Serum

ITP enhanced RPA was carried out according to Example 1, with a complex sample of nucleic acid spiked into blood serum included in the TE at a concentration of 20% and fluorescent probes included in the LE, without external heat. FIG. 29 shows the integrated and normalized fluorescence intensity of the ITP plug of seven repeated reactions as a function of time, compared with a set of seven repeated ITP enhanced RPA reactions carried out on blood serum without the nucleic acid, with 95% confidence intervals. This example may be representative of blood-borne pathogen detection, such as HIV or HCV from whole blood. In order to create blood serum from whole blood, simple paper-based blood fractionation filters, such as the VIVID™ membrane filter, can be used remove red blood cells and create a plasma+pathogen solution that can be detected similarly to FIG. 29. These results demonstrate that nucleic acids from a complex mixture such as blood serum can be repeatedly detected.

Example 13. Simulation of Co-Focusing of RPA Reaction Reagents

The co-focusing of different RPA reaction reagents in an ITP enhanced RPA device was modeled in SPRESSO, a nonlinear electrophoresis solver. The result, shown in FIG. 30, shows that as the plug migrates, low-mobility proteins and high-mobility primers located in the LE will begin to co-focus with the nucleic acids inside of the ITP zone. The highly concentrated, well-mixed ITP reaction volume allows for efficient amplification of nucleic acids. $Mg^{2+}$, present in the LE initially, migrates in the opposite direction of the anion targets and creates a constant concentration of $Mg^{2+}$ throughout the ITP zone for RPA reaction catalysis.

Example 14. Automated and Handheld ITP Enhanced RPA Cartridge and Reader

In this example, ITP enhanced RPA is utilized to detect nucleic acids from complex matrices, such as clinical samples, using an automated, portable, and handheld device. The handheld device, shown in FIG. 31, consists of (1) a sealed, disposable cartridge with pre-stored dried reagents and liquid blister packs, and (2) a handheld reader that uses microelectronics and a mobile phone, or alternatively dedicated electronic and optical components, for power, imaging, analysis, and data transmission.

The device offers three key performance benefits: (1) single-step, instantaneous nucleic acid extraction and concentration from a clinical matrix with no moving parts; (2) amplification of nucleic acid sequence in less than 5 minutes with minimal or no external heating, and (3) unambiguous quantitative or qualitative read-out of results to diagnose disease status. These characteristics allow the device to require minimal user interaction and training, the ability to run in settings without significant infrastructure, reduce failure and upkeep of mechanical parts, and offer time-to-results of less than 10 minutes from any liquid clinical sample, including whole blood.

For device operation, sample is added to a single inlet on the cartridge, and the cartridge is sealed by sliding shut the containment lid. The sealed cartridge is then inserted into the reader, which causes rupture of blister packs to release liquid reagents for automated filling of channels or macro-porous membranes and rehydration of dried reagents. Integrated electrodes on the bottom of the cartridge snap into electrical contacts inside the reader during insertion to provide a small electrical current for device operation, during which RPA enhanced ITP proceeds according to FIG. 32. Rapid amplification of the nucleic acid in the presence of fluorescent probes provides a detectable fluorescence signal, as shown in FIG. 33.

The mobile phone, or other specifically designed electronic and optical components, will provide a user interface for device operation where the users can follow unambiguous commands to operate the diagnostic test. The test power, control, and imaging of results will all be completed automatically by the mobile phone or other dedicated components. The electrical and optical components will also capture images of fluorescent, chemi/bioluminescent, or colorimetric indicators during testing to provide quantitation of nucleic acids, as well as location for geotagging, and transmission of data for statistical and geographic analysis.

Example 15. Altering Target Mobility to Reduce Background Nucleic Acid Inhibition of ITP Enhanced RPA One issue with tube format RPA is that high concentrations of background nucleic acid, such as those found in whole blood, can inhibit the amplification reactions (Rohrman and Richards-Kortum, *Analytical Chemistry*, vol. 87, 2015). It is thus desirable to separate or remove background nucleic acid from the reaction between target nucleic acids and RPA amplification reagents. This example leverages the use of separating target nucleic acids from background nucleic acids based on electrophoretic mobility in an ITP based system or by specifically capturing confounding nucleic acid prior to or during ITP operation.

ITP separates ions into different zones based on their electrophoretic mobilities, the velocity of ions under an applied electric field (units $m^2V^{-1}s^{-1}$). However, the relatively constant charge to mass ratio of nucleic acids means that the electrophoretic mobility of all native nucleic acids is essentially constant, with small deviations at very low molecular weight of less than <400 base pairs (Stellwagen et al., *Biopolymers*, vol. 42, 1997). This example utilizes a sequence specific probe that can bind to the target nucleic acid so that the mobility of the target is altered, allowing it to be focused in a different reaction zone from the background nucleic acid, as shown in FIG. 34.

The two zones, one containing modified target nucleic acid and one containing background nucleic acid, are separated due to mobility differences between the modified and background nucleic acid during ITP operation. The separation may be enhanced by using a spacer ion, which has a mobility between that of the modified target and native background nucleic acid (see, e.g., U.S. Pat. No. 7,951,278 and Eid et al., *Analyst*, vol. 138, 2013). In one example, the target nucleic acid is modified to be faster than background nucleic acid so the mobility of each species i, $\mu_i$, orders as: $\mu_{modified\_target} > \mu_{background\_nucleic\_acid}$ or $\mu_{modified\_target} > \mu_{spacer\_ion} > \mu_{background\_nucleic\_acid}$ if a spacer ion is included. In another example, the target nucleic acid is modified to be slower than background nucleic acid so the mobility of each species orders as: $\mu_{background\_nucleic\_acid} > \mu_{modified\_target}$ or $\mu_{background\_nucleic\_acid} > \mu_{spacer\_ion} > \mu_{modified\_target}$ if a spacer ion is included. A vast library of oligonucleotide modifications exist that may be used to create sequence specific probes with linker chemistries to modify the mobility of the target, including, but not limited to: Acrydites, Azides, NHS Esters, Amino modifiers, Alkines, Biotinylation, Thiol, Fluorophore, modified bases, and phosphorylation modification chemistries.

If the sequence of confounding nucleic acid is known, sequence specific probes can be used to capture the confounding nucleic acid so that it is unable to enter the ITP plug containing target nucleic acid. The capture probes can be immobilized on the substrate surface in the sample reservoir or in the channel path near the sample reservoir so that confounding nucleic acid cannot electromigrate with the target nucleic acid as it moves through the channel or macro-porous substrate. The sequence-specific probes can be oligonucleotides that contain complementary base-pair sequences that bind to the confounding nucleic acid through a hybridization reaction. For single-stranded nucleic acids, the sequence-specific modifications and capture can be done without additional steps. For double-stranded DNA, denaturing of the strands is likely required prior to using the sequence specific probes, which may be done using an initial heating step at 95° C., using chemical denaturing agents such as urea or organic solvents, or by other known methods such as high solution pH or low solution salt concentration.

Example 16. Quantitative Detection of Initial Target Concentration Using ITP Enhanced RPA Qualitative detection of targets is sufficient for many diagnostic applications, but in situations such as viral load monitoring before, during, and after treatment, quantitative information about the number of pathogens present in a clinical sample is required. This invention monitors the progress and endpoints of ITP-enhanced reactions and compares them to a control reaction in order to provide quantitative information about the initial target pathogen concentration in the tested sample.

The quantitative information can be obtained using a number of different methods that may vary the location of the target and control reactions, use kinetic and/or endpoint measurements, use a certain time and/or location for measurement, and/or using specific capture zones of reaction products. A few examples of these different methods include but are not limited to: (1) monitoring the target and control reaction in the same ITP reaction zone using different wavelengths of fluorescence emission, (2) monitoring the target and control reactions in different ITP reaction zones using the same or different wavelengths of fluorescence emission, (3) having the control and target reaction in different channels, while making measurements on each, (4) reading out the intensity of colorimetric capture line(s), where the optical intensity and/or number of capture lines is used to determine pathogen loads, and (5) measuring fluorescence endpoint at a given time or at a specific location (test line). FIG. 35 shows an example of monitoring target and control reactions in the same ITP plug with different fluorescence wavelengths. Some examples of existing quantitative analysis of nucleic acid amplification reactions include real-time kinetic PCR reactions (Heid, *Genome Research*, vol. 6, 1996), quantitative immunochromatographic assays (U.S. Pat. Nos. 5,753,517 and 7,659,086), and quantitative standard RPA reaction (Crannel et al, *Analytical Chemistry*, vol. 86, 2014).

In any of these given methods, the input and output from the control reaction is known a priori and serves as a calibration or normalization factor for the test reaction. An algorithm to relate the test reaction to the control is determined by running multiple replicates of known quantity assays and performing various statistical analyses on the reaction outputs. The algorithm is validated using a separate test set of reactions that differ from the training set used to develop the algorithm. Using the test in the same manner as the validation assays allows for the validated algorithm to determine target quantities for unknown samples.

We claim:

1. A method for concentrating and amplifying a nucleic acid, the method comprising
    providing an isotachophoresis device, the isotachophoresis device including
        a porous matrix having a first end and a second end opposing the first end, the first end and the second end defining a first axis, the porous matrix having a first fluid pathway having a first end and extending to a second end,
        a first electrode, and
        a second electrode;
        a first fluid comprising a trailing electrolyte, disposed in the porous matrix within the first fluid pathway, the trailing electrolyte comprising an ion and a counterion, the first fluid being disposed such that the first electrode is in conductive contact with the first end of the first fluid pathway,
        a second fluid comprising a leading electrolyte, disposed in the porous matrix within the first fluid pathway, the leading electrolyte comprising an ion and a counterion, the ion of the trailing electrolyte having a lower effective electrophoretic mobility than the ion of the leading electrolyte,
        a set of isothermal nucleic acid amplification (INAA) reaction reagents, disposed in the porous matrix within the first fluid pathway and
        the nucleic acid disposed in the porous matrix within the first fluid pathway, the nucleic acid having a higher effective electrophoretic mobility than the ion of the trailing electrolyte and a lower effective electrophoretic mobility than the ion of the leading electrolyte; and
    applying a voltage across the first electrode and the second electrode for a time sufficient to provide a first isotachophoresis (ITP) plug comprising an amplification product of the nucleic acid, wherein the concentration of the nucleic acid is substantially higher in the first ITP plug than in the first and/or second fluids outside of the first ITP plug.

2. The method according to claim 1, wherein one or more reagents of the set of INAA reaction reagents are present in the second fluid, and/or wherein one or more of the reagents of the set of INAA reaction reagents are disposed within the porous matrix in the first fluid pathway before the first fluid and the second fluid are introduced to the first fluid pathway.

3. The method according to claim 1, wherein providing the device comprises providing a dry device, the dry device comprising at least the porous matrix, the dry device further comprising one or more reagents of the set of INAA reaction reagents disposed in dry form in one or more zones of the first fluid pathway, the method comprising dissolving or suspending the one or more dry form INAA reaction reagents in the first fluid and/or the second fluid; or
    providing a dry device, the dry device comprising at least the porous matrix, the dry device further comprising the leading electrolyte disposed in dry form in one or more zones of the first fluid pathway, the method comprising dissolving the leading electrolyte to form the second fluid; or
    providing a dry device, the dry device comprising at least the porous matrix, the dry device further comprising the trailing electrolyte disposed in dry form in one or more zones of the first fluid pathway, the method comprising dissolving the trailing electrolyte to form the first fluid.

4. The method according to claim 1, wherein the leading electrolyte is disposed closer to the second end of the first fluid pathway than is the trailing electrolyte.

5. The method according to claim 1, wherein the nucleic acid is present in the first fluid.

6. The method according to claim 1, wherein the second fluid is introduced to the first fluid pathway before the first fluid is introduced to the first fluid pathway, and/or wherein the first fluid is introduced to the first fluid pathway by disposing an end of the device into a body of the first fluid, such that the first fluid is absorbed into the first fluid pathway at the first end thereof.

7. The method according to claim 1, wherein the second fluid is introduced to the first fluid pathway by disposing an end of the device into a body of the second fluid, such that the second fluid is absorbed into the first fluid pathway at the second end thereof, or wherein the second fluid is introduced to the first fluid pathway by dispensing the second fluid onto the first fluid pathway along the first axis.

8. The method according to claim 1, wherein the concentration of the trailing electrolyte in the first fluid is between about 1 μM-500 mM, and/or wherein the concentration of the leading electrolyte in the second fluid is between about 1 mM-1 M.

9. The method according to claim 1, wherein the effective mobility of the ion of the leading electrolyte is greater than about $4.0 \times 10^{-8}$ $m^2V^{-1}s^{-1}$, and/or wherein the effective mobility of the ion of the trailing electrolyte is less than about $4.0 \times 10^{-8}$ $m^2V^{-1}s^{-1}$ and/or wherein the difference between the effective mobilities of the ion of the leading electrolyte and the ion of the trailing electrolyte is at least about $3 \times 10^{-8}$ $m^2V^{-1}s^{-1}$.

10. The method according to claim 1, wherein one or more of the reagents of the set of INAA reagents have an effective mobility between the effective mobility of the ion of the leading electrolyte and the ion of the trailing electrolyte; and/or wherein the one or more INAA reagents are recombinase polymerase amplification (RPA) reagents, and/ or wherein the one or more INAA reagents are loop-mediated isothermal amplification (LAMP) reagents, helicase dependent amplifier reaction HDA), nicking enzyme amplification reaction (NEAR) reagents, nucleic acid sequence based amplification (NASBA) reagents, strand displacement amplification (SDA) reagents, or cross-priming amplification (CPA) reagents.

11. The method according to claim 1, wherein the porous matrix has an average pore size in the range of about 0.1 µm to about 100 µm, and/or wherein the porous matrix has a porosity of at least 80%, and/or wherein the porous matrix has an internal surface area ratio in the range of about 50 to about 200, and/or wherein the porous matrix is formed from a glass, plastic, paper, polymer, or membrane material, and/or wherein the porous matrix is disposed in a closeable casing.

12. The method according to claim 1, wherein the voltage applied to the provided device is between 1-2500 Volts, and/or wherein applying the voltage provides a current flow between $10^{-6}$-50 milliamperes to the provided device, and/or wherein applying the voltage provides a current flow sufficient to provide Joule heating of the first fluid pathway to a temperature of at least 25° C.

13. The method according to claim 1, wherein the leading electrolyte comprises a chloride ion, a bicarbonate ion, a sulfate ion, an acetate ion, a bromide ion, a bromate ion, a chlorate ion, an iodate ion, a tris counterion, an imidazole counterion, a bis-tris counterion, a bis-tris propane counterion, or an ammediol counterion, or a nitrate ion, and/or wherein the trailing electrolyte comprises a HEPES ion, a glycine ion, a serine ion, a tricine ion, a bicine ion, a TAPS ion, a MOPS ion, a tris counterion, an imidazole counterion, a bis-tris counterion, a bis-tris propane counterion, or an ammediol counterion, a beta-alanine ion, a valine ion, a leucine ion, or an isoleucine ion.

14. The method according to claim 1, wherein the first and/or second fluid further comprise at least one water-soluble material selected from the group comprising polymeric surfactants, charged polymers, polyol compounds, poly(vinyl alcohol), poly(alkylene glycol) polymers, polyethylene glycol (PEG), polyvinylpyrrolidone (PVP), TWEEN® 20, TRITON™ X, polylactams, substituted polyacrylamide derivatives, and water soluble methylhydroxyethyl derivatives of cellulose.

15. The method according to claim 1, wherein applying the voltage provides a first ITP plug comprising nucleic acids in at least a 10-fold higher concentration than the nucleic acid concentration in the first and/or second fluids outside of the first ITP plug.

16. The method according to claim 15, wherein a reaction of the INAA reagents with the nucleic acids provides a nucleic acid amplification product wherein the concentration of nucleic acids in the first ITP plug is increased relative to the nucleic acid concentration in the first and/or second fluids outside of the first ITP plug by a factor of at least 100.

17. The method according to claim 1, wherein the ITP plug contacts a detection zone of the porous matrix to provide a detectable change, such as colorimetric, voltammetric, chemical, bioluminescence, chemiluminescence, fluorescence, turbidity, or thermodynamic change.

18. The method according to claim 17, wherein the detection zone includes a detection substance capable of interacting with the analyte to provide a detectable change.

19. The method according to claim 18, wherein the detection substance is an oligo- or polypeptide such as a protein, an oligo- or polynucleotide, a colorimetric reagent, a nanoparticle, or a small molecule, and/or wherein the detection zone is configured for an assay selected from an immunoassay, an ELISA, a sandwich assay, and a nucleotide binding assay.

20. The method according to claim 18, wherein the provided device comprises an optical readout system configured to perform an optical measurement on the detection zone, such as wherein the optical readout system comprises a camera-equipped mobile phone.

* * * * *